(12) United States Patent
Steiger et al.

(10) Patent No.: US 6,723,720 B2
(45) Date of Patent: Apr. 20, 2004

(54) PESTICIDAL TRIAZINE-DERIVATIVES

(75) Inventors: Arthur Steiger, Arlesheim (CH);
Werner Zambach, Bättwil (CH);
André Jeanguenat, Basel (CH);
Martin Eberle, Bottmingen (CH);
Stephan Trah, Freiburg im Breisgau (DE); Saleem Farooq, Arisdorf (CH)

(73) Assignee: Novartis Animal Health US, Inc., Greensboro, NC (US)

( * ) Notice: Subject to any disclaimer, the term of this patent is extended or adjusted under 35 U.S.C. 154(b) by 0 days.

(21) Appl. No.: 10/006,954

(22) Filed: Nov. 5, 2001

(65) Prior Publication Data

US 2003/0036544 A1 Feb. 20, 2003

Related U.S. Application Data

(63) Continuation of application No. PCT/EP00/03921, filed on May 2, 2000.

(30) Foreign Application Priority Data

Apr. 5, 1999 (CH) ................................................. 832/99

(51) Int. Cl.[7] ................. C07D 253/065; C07D 253/07; A01N 43/707
(52) U.S. Cl. ....................................... 514/242; 544/182
(58) Field of Search ........................... 544/182; 514/242

(56) References Cited

U.S. PATENT DOCUMENTS 4,931,487 A  6/1990  Priester, Jr. et al. ......... 521/163

FOREIGN PATENT DOCUMENTS

| EP | 0 314 615 | 10/1988 |
|---|---|---|
| EP | 0 495 709 | 1/1992 |
| GB | 2 293 380 | 9/1995 |
| WO | WO 97/28154 | 1/1997 |
| WO | WO 99/54311 | 4/1998 |
| WO | WO 98/42686 | 10/1998 |

OTHER PUBLICATIONS

English Abstract of Chemical Abstract 78:84376y, (Nalepa et al., J. fur Praktische Chemie), no year.
English Abstract of Chemical Abstract 96:68854u, (Pochat, Terahedron Lett.), no year.
English Abstract of Chemical Abstract 87:152140e, (Zaschke et al., J. Prakt. Chem.), no year.
English Abstract of Chemical Abstract 84:59404x. (Reimlinger et al., Chem. Ber.), no year.
Taylor et al., J. Org. Chem. 1989, vol. 54, 1245–1249.
Nalepa et al., J. fur praktische Chemie, vol. 314 (1972), p. 851–856.
Konno et al., J. Abr. Food. Chem., vol. 43, p. 838–842 (1995).
Pochat, Tetrahedron Lett., vol. 22, (1981), p. 3595–3596.
Zaschke et al., J. Prakt. Chem., vol. 319, (1977), p. 475–484.
Reimlinger et al., Chem. Ber., vol. 108, 3799–3806 (1975).
Magirius et al., Helv. Chim. A., vol. 76, pp. 1980–1981, 1989.
Kamitori et al., Heterocycles, vol. 39 (1994), p. 155–162.

Primary Examiner—John M. Ford
(74) Attorney, Agent, or Firm—John W. Kung

(57) ABSTRACT

A compound of formula

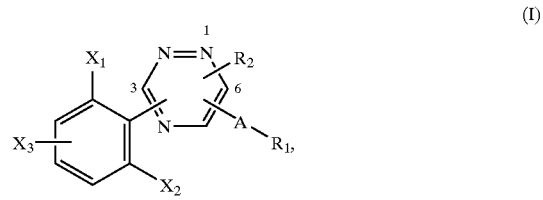

(I)

wherein
$R_1$ is unsubstituted or substituted aryl or heteroaryl, the substituents of the aryl and heteroaryl rings being selected, for example, from the group consisting of OH, halogen, CN, $NO_2$, $C_1$–$C_6$alkyl, $C_3$–$C_8$cycloalkyl, $C_1$–$C_6$alkyl-$C_3$–$C_8$cycloalkyl, $C_3$–$C_8$cycloalkyl-$C_1$–$C_6$alkyl, $C_1$–$C_6$haloalkyl, $C_3$–$C_8$halocycloalkyl, $C_1$–$C_6$alkoxy and phenyl; phenoxy; phenylthio; phenylamino; and phenyl-($C_1$–$C_6$alkyl)-amino;
the substituents of the phenoxy, phenylthio, phenylamino and phenyl-($C_1$–$C_6$alkyl)-amino groups being selected from the group consisting of halogen, CN, $NO_2$, $C_1$–$C_6$alkyl, $C_3$–$C_8$cycloalkyl, $C_1$–$C_6$haloalkyl, $C_3$–$C_8$halocycloalkyl, $C_1$–$C_6$alkoxy, $C_3$–$C_8$cycloalkoxy, $C_1$–$C_6$alkylthio, $C_3$–$C_8$cycloalkylthio, $C_1$–$C_6$haloalkylthio and $C_3$–$C_8$halocycloalkylthio;
$R_2$ is, for example, H, OH, halogen, CN, $NO_2$, $C_1$–$C_6$alkyl or $C_1$–$C_6$alkoxy;
A is, for example, a single bond, $C_1$–$C_{12}$alkylene, O or $O(C_1$–$C_{12}$alkylene);
$R_4$ is H, $C_1$–$C_6$alkyl, $C_3$–$C_8$cycloalkyl, $C_1$–$C_6$haloalkyl, $C_1$–$C_6$alkoxy, $N(R_5)_2$ or $C_1$–$C_6$alkoxy-$C_2$–$C_6$alkyl;
$R_5$ is H, $C_1$–$C_6$alkyl, $C_3$–$C_8$cycloalkyl, $C_1$–$C_6$haloalkyl or aryl-$C_1$–$C_6$alkyl;
$X_1$ is $R_{10}$; $X_2$ and $X_3$ are each independently of the other H or $R_{10}$;
$R_{10}$ is, for example, halogen, CN, $NO_2$, $C_1$–$C_6$alkyl or $C_3$–$C_8$cycloalkyl; and n is 0, 1 or 2,
and to their physiologically tolerable and agrochemically acceptable addition compounds, and where appropriate to E/Z isomers, to mixtures of E/Z isomers and/or to tautomers, in each case in free form or in salt form.

The compounds, in free form or in agrochemically acceptable salt form, exhibit advantageous pesticidal properties. They are suitable especially in the control of pests in agriculture and stored goods and also in the keeping of domestic animals.

6 Claims, No Drawings

PESTICIDAL TRIAZINE-DERIVATIVES

This application is a continuation of International Application No. PCT/EP00/03921, filed May 2, 2000, the contents of which are incorporated herein by reference.

The present invention relates to a compound of formula

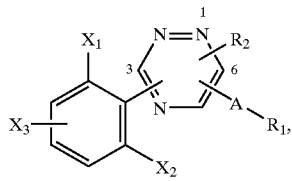

(I)

wherein $R_1$ is unsubstituted or mono- to penta-substituted aryl or heteroaryl, the substituents of the aryl and heteroaryl rings being selected from the group consisting of OH, halogen, CN, $NO_2$, $C_1$–$C_6$alkyl, $C_3$–$C_8$cycloalkyl, optionally substituted $C_3$–$C_8$cycloalkenyl, $C_1$–$C_6$alkyl-$C_3$–$C_8$cycloalkyl, $C_3$–$C_8$cycloalkyl-$C_1$–$C_6$alkyl, $C_1$–$C_6$haloalkyl, $C_3$–$C_8$halocycloalkyl, $C_1$–$C_6$alkoxy, $C_3$–$C_8$cycloalkoxy, $C_1$–$C_6$haloalkoxy, $C_3$–$C_8$halocycloalkoxy, $C_1$–$C_6$alkylthio, $C_3$–$C_8$cycloalkylthio, $C_1$–$C_6$haloalkylthio, $C_3$–$C_8$halocycloalkylthio, $C_1$–$C_6$alkylsulfinyl, $C_3$–$C_8$cycloalkylsulfinyl, $C_1$–$C_6$haloalkylsulfinyl, $C_3$–$C_8$halocycloalkylsulfinyl, $C_1$–$C_6$alkylsulfonyl, $C_3$–$C_8$cycloalkylsulfonyl, $C_1$–$C_6$haloalkylsulfonyl, $C_3$–$C_8$halocycloalkylsulfonyl, optionally substituted $C_2$–$C_8$alkenyl, optionally substituted $C_2$–$C_8$alkynyl, $C_1$–$C_6$alkylcarbonyl, $C_1$–$C_6$alkyl-C(=$NOR_6$), —P(=O)(O$C_1$–$C_6$alkyl)$_2$, R7, unsubstituted or mono- to penta-substituted phenyl, unsubstituted or mono- to penta-substituted heteroaryl; wherein the substituents of the said phenyl and heteroaryl radicals are selected from the group consisting of OH, halogen, CN, $NO_2$, $C_1$–$C_6$alkyl, optionally substituted $C_2$–$C_8$alkenyl, optionally substituted $C_2$–$C_8$alkynyl, $C_3$–$C_8$cycloalkyl, optionally substituted $C_3$–$C_8$cycloalkenyl, $C_1$–$C_6$haloalkyl, $C_3$–$C_8$halocycloalkyl, $C_1$–$C_6$alkoxy, $C_3$–$C_8$cycloalkoxy, $C_1$–$C_6$haloalkoxy, $C_3$–$C_8$halocycloalkoxy, $C_1$–$C_6$alkylthio, $C_3$–$C_8$cycloalkylthio, $C_1$–$C_6$haloalkylthio, $C_3$–$C_8$halocycloalkylthio, $C_1$–$C_6$alkylsulfinyl, $C_3$–$C_8$cycloalkylsulfinyl, $C_1$–$C_6$haloalkylsulfinyl, $C_3$–$C_8$halocycloalkylsulfinyl, $C_1$–$C_6$alkylsulfonyl, $C_3$–$C_8$cycloalkylsulfonyl, $C_1$–$C_6$haloalkylsulfonyl, $C_3$–$C_8$halocycloalkylsulfonyl, $C_2$–$C_8$alkenyl, which is unsubstituted or substituted, $C_2$–$C_8$alkynyl, which is unsubstituted or substituted, $C_1$–$C_6$alkylcarbonyl, —CH(=$NOR_6$), —C($C_1$–$C_6$alkyl)(=$NOR_6$), $C_1$–$C_6$alkyl-C(=$NOR_6$), —CHO, —C(=O)—$C_1$–$C_6$alkyl and R7;

unsubstituted or mono- to penta-substituted phenoxy;
unsubstituted or mono- to penta-substituted phenylthio;
unsubstituted or mono- to penta-substituted phenylamino; and
unsubstituted or mono- to penta-substituted phenyl-($C_1$–$C_6$alkyl)-amino;
the substituents of the phenoxy, phenylthio, phenylamino and phenyl-($C_1$–$C_6$alkyl)-amino groups being selected from the group consisting of halogen, CN, $NO_2$, $C_1$–$C_6$alkyl, $C_3$–$C_8$-cycloalkyl, $C_1$–$C_6$haloalkyl, $C_3$–$C_8$halocycloalkyl, $C_1$–$C_6$alkoxy, $C_1$–$C_6$haloalkoxy, $C_3$–$C_8$cycloalkoxy, $C_1$–$C_6$alkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, $C_3$–$C_8$cycloalkylthio, $C_1$–$C_6$haloalkylthio and $C_3$–$C_8$halocycloalkylthio;

$R_2$ is H, OH, halogen, CN, $NO_2$, optionally substituted $C_1$–$C_6$alkyl, $C_1$–$C_6$alkoxy, $C_1$–$C_6$alkoxy-$C_1$–$C_6$alkyl, $C_1$–$C_6$alkylthio, $C_1$–$C_6$alkylthio-$C_1$–$C_6$alkyl, $C_3$–$C_8$cycloalkyl, $C_1$–$C_6$haloalkyl, $C_3$–$C_8$halocycloalkyl, —NH—$C_1$–$C_6$-alkyl, SH or $CH_2$—$NO_2$;

A is a single bond, $C_1$–$C_{12}$alkylene, O, O($C_1$–$C_{12}$alkylene), $S(O)_n$, $S(O)_n$($C_1$–$C_{12}$alkylene), $C_2$–$C_8$alkenylene, $C_2$–$C_8$alkynylene; $NR_3$ or $NR_3$($C_1$–$C_{12}$alkylene);

$R_3$ is H, $C_1$–$C_6$alkyl, $C_3$–$C_8$cycloalkyl, $C_1$–$C_6$haloalkyl, $C_2$–$C_8$alkenyl, $C_2$–$C_8$alkynyl, aryl-$C_1$–$C_6$alkyl, $(CH_2)_p$C(O)$R_4$ or $C_1$–$C_6$alkoxy-$C_2$–$C_6$alkyl;

$R_4$ is H, $C_1$–$C_6$alkyl, $C_3$–$C_8$cycloalkyl, $C_1$–$C_6$haloalkyl, $C_1$–$C_6$alkoxy, $N(R_5)_2$ or $C_1$–$C_6$alkoxy-$C_2$–$C_6$alkyl;

$R_5$ is H, $C_1$–$C_6$alkyl, $C_3$–$C_8$cycloalkyl, $C_1$–$C_6$haloalkyl or aryl-$C_1$–$C_6$alkyl;

$R_6$ is H, $C_1$–$C_6$alkyl, $C_3$–$C_8$cycloalkyl or —C(=O)—$R_5$;

$R_7$ is

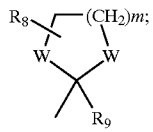

$R_8$ and $R_9$ are each independently of the other H or $C_1$–$C_6$alkyl;

$X_1$ is $R_{10}$;

$X_2$ and $X_3$ are each independently of the other H or $R_{10}$;

$R_{10}$ is halogen, CN, $NO_2$, $C_1$–$C_6$alkyl, $C_3$–$C_8$cycloalkyl, $C_1$–$C_6$haloalkyl, $C_3$–$C_8$halocycloalkyl, $C_1$–$C_6$alkoxy, $C_3$–$C_8$cycloalkoxy, $C_1$–$C_6$haloalkoxy, $C_3$–$C_8$halocycloalkoxy, $C_1$–$C_6$alkylthio, $C_3$–$C_8$cycloalkylthio, $C_1$–$C_6$haloalkylthio or $C_3$–$C_8$halocycloalkylthio;

m is 1, 2, 3 or 4;
n is 0, 1 or 2; and
W is O or S;

with the proviso that the radical A—$R_1$ and the phenyl group substituted by $X_1$, $X_2$ and $X_3$ are not in the vicinal position relative to one another on the triazine ring, with the further proviso, that $X_1$ is not $CH_3$, Cl or F, when $X_2$ and $X_3$ are H, A is a single bond, $R_1$ is phenyl, 2-fluorophenyl, p-fluorophenyl or 3-chlorophenyl and $R_2$ is H, Cl or $NHC_2$—$H_5$;

and with the exception of 3,6-di-(2-chlorophenyl)-5-hydroxy-1,2,4-triazine and with the exception of 3-(2-methylphenyl)-6-(4-methylphenyl)-5-trifluoromethyl-1,2,4-triazine;

and to the physiologically tolerable and agrochemically acceptable addition compounds thereof, and where appropriate to E/Z isomers, to mixtures of E/Z isomers and/or to tautomers, in each case in free form or in salt form;

to a process for the preparation of those compounds and to their use, to pesticidal compositions in which the active ingredient is selected from those compounds, in each case in free form or in agrochemically acceptable salt form, and to a process for the manufacture of those compositions and to their use.

Preferred are compounds of the formula (I), wherein $R_1$ is unsubstituted or mono- to penta-substituted aryl or heteroaryl, wherein the substituents are selected from the group consisting of OH, Halogen, CN, $NO_2$, $C_1$–$C_6$-Alkyl, $C_3$–$C_8$-Cycloalkyl, $C_1$–$C_6$-Alkyl-$C_3$–$C_8$- cycloalkyl, $C_3$–$C_8$-Cycloalkyl-$C_1$–$C_6$-alkyl, $C_1$–$C_6$-Haloalkyl, $C_3$–$C_8$-Halocycloalkyl, $C_1$–$C_6$-Alkoxy, $C_3$–$C_8$-Cycloalkoxy, $C_1$–$C_6$-Haloalkoxy, $C_3$–$C_8$-Halocycloalkoxy, $C_1$–$C_6$-Alkylthio, $C_3$–$C_8$-Cycloalkylthio, $C_1$–$C_6$-Haloalkylthio, $C_3$–$C_8$-Halocycloalkylthio, $C_1$–$C_6$-Alkylsulfinyl, $C_3$–$C_8$-Cycloalkylsulfinyl, $C_1$–$C_6$-Haloalkylsulfinyl, $C_3$–$C_8$-Halocycloalkylsulfinyl, $C_1$–$C_6$-Alkylsulfonyl, $C_3$–$C_8$-Cycloalkylsulfonyl, $C_1$–$C_6$-Haloalkylsulfonyl, $C_3$–$C_8$-Halocycloalkylsulfonyl, $C_1$–$C_8$-Alkenyl, $C_2$–$C_8$-Alkinyl, $C_1$–$C_6$-Alkylcarbonyl, $C_1$–$C_6$-Alkyl-C(=NOR$_6$), R$_7$, is unsubstituted or mono- to penta-substituted phenyl, wherein the substituents are selected from the group consisting of OH, Halogen, CN, NO$_2$, $C_1$–$C_6$-Alkyl, $C_3$–$C_8$-Cycloalkyl, $C_1$–$C_6$-Haloalkyl, $C_3$–$C_8$-Halocycloalkyl, $C_1$–$C_6$-Alkoxy, $C_3$–$C_8$-Cycloalkoxy, $C_1$–$C_6$-Haloalkoxy, $C_3$–$C_8$-Halocycloalkoxy, $C_1$–$C_6$-Alkylthio, $C_3$–$C_8$-Cycloalkylthio, $C_1$–$C_6$-Haloalkylthio, $C_3$–$C_8$-Halocycloalkylthio, $C_1$–$C_6$-Alkylsulfinyl, $C_3$–$C_8$-Cycloalkylsulfinyl, $C_1$–$C_6$-Haloalkylsulfinyl, $C_3$–$C_8$-Halocycloalkylsulfinyl, $C_1$–$C_6$-Alkylsulfonyl, $C_3$–$C_8$-Cycloalkylsulfonyl, $C_1$–$C_6$-Haloalkylsulfonyl, $C_3$–$C_8$-Halocycloalkylsulfonyl, $C_2$–$C_8$-Alkenyl, $C_2$–$C_8$-Alkinyl, $C_1$–$C_6$-Alkylcarbonyl, $C_1$–$C_6$-Alkyl-C(=NOR$_6$) and R$_7$; is unsubstituted or mono- to penta-substituted phenoxy, is unsubstituted or mono- to penta-substituted phenylthio, is unsubstituted or mono- to penta-substituted phenylamino and is unsubstituted or mono- to penta-substituted phenyl-($C_1$–$C_6$-alkyl)-amino, wherein the substituents are selected from the group consisting of Halogen, CN, NO$_2$, $C_1$–$C_6$-Alkyl, $C_3$–$C_8$-Cycloalkyl, $C_1$–$C_6$-Haloalkyl, $C_3$–$C_8$-Halocycloalkyl, $C_1$–$C_6$-Alkoxy, $C_3$–$C_8$-Cycloalkoxy, $C_1$–$C_6$-Alkylthio, $C_3$–$C_8$-Cycloalkylthio, $C_1$–$C_6$-Haloalkylthio and $C_3$–$C_8$-Halocycloalkylthio;

R$_2$ is H, Halogen, CN, NO$_2$, $C_1$–$C_6$-Alkyl, $C_3$–$C_8$-Cycloalkyl, $C_1$–$C_6$-Haloalkyl or $C_3$–$C_8$-Halocycloalkyl;

A is $(CR_{11}R_{12})_p$, $O(CR_{11}R_{12})_p$, $S(O)_n(CR_{11}R_{12})_p$, unsubstituted or substituted $C_2$–$C_8$-Alkenylen, unsubstituted or substituted $C_2$–$C_8$-Alkinylen, wherein the substituents are selected from the group consisting of R$_1$, and R$_{12}$; or NR$_3$(CH$_2$)$_p$;

R$_3$ is H, $C_1$–$C_6$-Alkyl, $C_3$–$C_8$-Cycloalkyl, $C_1$–$C_6$-Haloalkyl, $C_2$–$C_8$-Alkenyl, $C_2$–$C_8$-Alkinyl, Aryl-$C_1$–$C_6$-alkyl, (CH$_2$)$_p$C(O)R$_4$ or $C_1$–$C_6$-Alkoxy-$C_2$–$C_6$-alkyl;

R$_4$ is H, $C_1$–$C_6$-Alkyl, $C_3$–$C_8$-Cycloalkyl, $C_1$–$C_6$-Haloalkyl, $C_1$–$C_6$-Alkoxy, N(R$_5$)$_2$ or $C_1$–$C_6$-Alkoxy-$C_2$–$C_6$-alkyl;

R$_5$ is H, $C_1$–$C_6$-Alkyl, $C_3$–$C_8$-Cycloalkyl, $C_1$–$C_6$-Haloalkyl or Aryl-$C_1$–$C_6$-alkyl;

R$_6$ is H, $C_1$–$C_6$-Alkyl or $C_3$–$C_8$-Cycloalkyl;

R$_7$ is

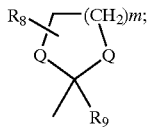

R$_8$ and R$_9$ are each independently of the other H or $C_1$–$C_6$-Alkyl;

X$_1$ is R$_{10}$;

X$_2$ and X$_3$ are each independently of the other H or R$_{10}$;

R$_{10}$ is Halogen, CN, NO$_2$, $C_1$–$C_6$-Alkyl, $C_3$–$C_8$-Cycloalkyl, $C_1$–$C_6$-Haloalkyl, $C_3$–$C_8$-Halocycloalkyl, $C_1$–$C_6$-Alkoxy, $C_3$–$C_8$-Cycloalkoxy, $C_1$–$C_6$-Haloalkoxy, $C_3$–$C_8$-Halocycloalkoxy, $C_1$–$C_6$-Alkylthio, $C_3$–$C_8$-Cycloalkylthio, $C_1$–$C_6$-Haloalkylthio or $C_3$–$C_8$-Halocycloalkylthio;

R$_{11}$ and R$_{12}$ are each independently of the other H or $C_1$–$C_6$-Alkyl;

m 1, 2, 3 or 4;

n is 0, 1 or 2;

p is 0, 1, 2, 3, 4, 5 or 6; and

Q is O or S.

Certain 1,2,4-triazine derivatives are proposed in the literature as active ingredients in compositions for controlling pests on domestic animals and productive livestock and in crops of useful plants. The biological properties of those known compounds are not entirely satisfactory in the field of pest control, however, for which reason there is a need to provide further compounds having pesticidal properties, that problem being solved according to the invention by the provision of the present compounds of formula (I). Because they contain at least three basic centres, the compounds of formula (I) may be in the form of salts or may form e.g. acid addition salts. The latter are formed, for example, with strong inorganic acids, such as mineral acids, e.g. sulfuric acid, a phosphoric acid or a hydrohalic acid, with strong organic carboxylic acids, such as unsubstituted or substituted, e.g. halo-substituted, $C_1$–$C_4$alkanecarboxylic acids, for example acetic acid, saturated or unsaturated dicarboxylic acids, e.g. oxalic, malonic, maleic, fumaric or phthalic acid, hydroxycarboxylic acids, e.g. ascorbic, lactic, malic, tartaric or citric acid, or benzoic acid, or with organic sulfonic acids, such as unsubstituted or substituted, e.g. halo-substituted, $C_1$–$C_4$alkane- or aryl-sulfonic acids, e.g. methane- or p-toluene-sulfonic acid. Hereinabove and hereinbelow any reference to the free compounds of formula (I) or to their salts is to be understood as including also the corresponding salts or the free compounds of formula (I), respectively, as appropriate and expedient, the free form being preferred.

The general terms used hereinabove and hereinbelow have the meanings given below, unless defined otherwise.

Unless defined otherwise, carbon-containing groups and compounds each contain from 1 up to and including 6, preferably from 1 up to and including 4, more especially 1 or 2, carbon atoms.

Aryl is phenyl or naphthyl.

Heteroaryl is especially pyridyl, pyrimidyl, s-triazinyl, 1,2,4-triazinyl, thienyl, furanyl, pyrryl, pyrazolyl, imidazolyl, thiazolyl, triazolyl, oxazolyl, thiadiazolyl, oxadiazolyl, benzothienyl, benzofuranyl, benzothiazolyl, indolyl or indazolyl, which are preferably bonded via a carbon atom; thiazolyl, benzofuranyl, benzothiazolyl or indolyl, especially thiazolyl or indolyl, is preferred.

Halogen—both as a group per se and as a structural element of other groups and compounds, such as haloalkyl, haloalkoxy and haloalkylthio—is fluorine, chlorine, bromine or iodine, especially fluorine, chlorine or bromine, more especially fluorine or chlorine.

Alkyl—both as a group per se and as a structural element of other groups and compounds, such as haloalkyl, alkoxy and alkylthio—is, in each case giving due consideration to the number of carbon atoms contained in the group or compound in question, either straight-chained, i.e. methyl, ethyl, propyl, butyl, pentyl, hexyl, heptyl or octyl, or branched, for example isopropyl, isobutyl, sec-butyl, tert-butyl, isopentyl, neopentyl or isohexyl.

Cycloalkyl—both as a group per se and as a structural element of other groups and compounds, such as halocycloalkyl, cycloalkoxy and cycloalkylthio—is, in each case giving due consideration to the number of carbon atoms contained in the group or compound in question, cyclopropyl, cyclobutyl, cyclopentyl, cyclohexyl, cycloheptyl or cyclooctyl.

Alkenyl—both as a group per se and as a structural element of other groups and compounds—is, in each case giving due consideration to the number of carbon atoms and conjugated or isolated double bonds contained in the group or compound in question, either straight-chained, e.g. allyl, 2-butenyl, 3-pentenyl, 1-hexenyl, 1-heptenyl, 1,3-hexadienyl or 1,3-octadienyl, or branched, e.g. isopropenyl, isobutenyl, isoprenyl, tert-pentenyl, isohexenyl, isoheptenyl or isooctenyl.

Alkynyl—both as a group per se and as a structural element of other groups and compounds—is, in each case giving due consideration to the number of carbon atoms and conjugated or isolated double bonds contained in the group or compound in question, either straight-chained, e.g. propargyl, 2-butynyl, 3-pentynyl, 1-hexynyl, 1-heptynyl, 3-hexen-1-ynyl or 1,5-heptadien-3-ynyl, or branched, e.g. 3-methylbut-1-ynyl, 4-ethylpent-1-ynyl, 4-methylhex-2-ynyl or 2-methylhept-3-ynyl.

Alkylene, alkenylene and alkynylene are straight-chained or branched bridge members, especially —$CH_2$—, —$CH_2$—$CH_2$—, —$CH(CH_3)$—, —$CH(CH_3)CH_2$—, —$CH(CH_3)CH_2$—$CH_2$—, —$CH_2C(CH_3)_2$—$CH_2$—, —$CH$=$CH$—, —$CH_2$—$CH$=$CH$—, —$CH_2$—$CH$=$CH$—$CH_2$—; —$C$≡$C$—, and —$CH_2C$≡$C$—; more especially —$CH_2$—.

Halo-substituted carbon-containing groups and compounds, such as haloalkyl, haloalkoxy and haloalkylthio, may be partially halogenated or perhalogenated, the halogen substituents in the case of polyhalogenation being the same or different. Examples of haloalkyl—both as a group per se and as a structural element of other groups and compounds, such as haloalkoxy and haloalkylthio—are methyl substituted from one to three times by fluorine, chlorine and/or bromine, such as $CHF_2$ or $CF_3$; ethyl substituted from one to five times by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl substituted from one to seven times by fluorine, chlorine and/or bromine, such as $CH_2CHBrCH_2Br$, $CF_2CHFCF_3$, $CH_2CF_2CF_3$ or $CH(CF_3)_2$; butyl or an isomer thereof substituted from one to nine times by fluorine, chorine and/or bromine, such as $CF(CF_3)CHFCF_3$ or $CH_2(CF_2)_2CF_3$; pentyl or an isomer thereof substituted from one to eleven times by fluorine, chlorine and/or bromine, such as $CF(CF_3)(CHF)_2CF_3$ or $CH_2(CF_2)_3CF_3$; and hexyl or an isomer thereof substituted from one to thirteen times by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Optionally substituted radicals such as for instance $C_2$–$C_8$alkenyl, $C_2$–$C_8$alkynyl, $C_3$–$C_8$cycloalkenyl or $C_1$–$C_6$alkyl, are preferrably substituted with OH, CN, nitro, halogen, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$haloalkylsulfinyl, $C_1$–$C_6$alkylsulfonyl, $C_1$–$C_6$haloalkylsulfonyl, phenyl, halogenphenyl, phenoxy, $NHR_3$, —$C(=O)NH_2$, —$C(=O)O$—$C_1$–$C_6$-alkyl and —$C(=O)$—$C_1$–$C_6$-alkyl.

Preferred embodiments within the scope of the invention, taking into account the proviso mentioned above, are a compound of formula (I):

(1) wherein $R_1$ is an unsubstituted or mono- to tri-substituted aryl or heteroaryl ring, the substituents being selected from the group consisting of OH, halogen, CN, $NO_2$, $C_1$–$C_4$alkyl, $C_3$–$C_6$cycloalkyl, optionally substituted $C_5$–$C_6$cycloalkenyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsulfonyl, $C_1$–$C_4$haloalkylsulfonyl, optionally substituted $C_2$–$C_6$alkenyl, optionally substituted $C_2$–$C_6$alkynyl, $C_1$–$C_4$alkylcarbonyl, unsubstituted or mono- to penta-substituted phenyl, the substituents being selected from the group consisting of OH, halogen, CN, $NO_2$, $C_1$–$C_4$alkyl, $C_3$–$C_6$cycloalkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsulfonyl, $C_1$–$C_4$haloalkylsulfonyl, $C_2$–$C_6$alkenyl, $C_2$–$C_6$alkynyl and $C_1$–$C_4$alkylcarbonyl, and unsubstituted or mono- to penta-substituted phenoxy or unsubstituted or mono- to penta-substituted phenylamino, the substituents of the phenoxy- and phenylaminogroup being selected from the group consisting of halogen, CN, $NO_2$, $C_1$–$C_4$alkyl, $C_3$–$C_6$cycloalkyl, $C_1$–$C_4$haloalkyl, $C_1$–$C_4$alkoxy, $C_1$–$C_4$halo-alkoxy, $C_1$–$C_4$alkylthio, $C_1$–$C_4$alkylsulfinyl, $C_1$–$C_4$alkylsulfonyl, $C_1$–$C_4$haloalkylsulfinyl, $C_1$–$C_4$haloalkylsulfonyl, and $C_1$–$C_4$haloalkylthio;

especially mono- or di-substituted phenyl, the substituents being selected from the group consisting of halogen, CN, $NO_2$, $C_1$–$C_2$alkyl, $C_1$–$C_2$haloalkyl, $C_1$–$C_2$alkoxy, $C_1$–$C_2$haloalkoxy, unsubstituted or mono- or di-substituted phenyl, the substituents of the said phenyl being selected from the group consisting of halogen, $C_1$–$C_2$alkyl, $C_1$–$C_2$haloalkyl, $C_1$–$C_2$alkoxy, $C_1$–$C_2$haloalkoxy, $C_1$–$C_2$alkylthio and $C_1$–$C_2$haloalkylthio; and phenoxy;

more especially mono- or di-substituted phenyl, the substituents being selected from the group consisting of halogen, methyl, halomethyl, methoxy, halomethoxy, unsubstituted or mono- or di-substituted phenyl, the substituents being selected from the group consisting of halogen, methyl, halomethyl, methoxy, halomethoxy, methylthio and halomethylthio; and phenoxy;

especially wherein $R_1$ is a phenyl ring, which is monosubstituted by mono- or di-substituted phenyl, which is preferably in the 4-position, the substituents on the mentioned phenyl radical being selected from the group consisting of halogen, methyl, trifluoromethyl, methoxy, trifluoromethoxy, methylthio and trifluoromethylthio;

(2) wherein $R_2$ is H, halogen or $C_1$–$C_4$alkyl, especially H or $C_1$–$C_4$alkyl, more especially H;

(3) a compound of formula (I) wherein
A is a single bond, $C_1$–$C_4$alkylene, O, $OCH_2$, $C_2$–$C_4$alkenylene, $C_2$–$C_4$alkynylene or $NR_3$, especially a single bond, O, $OCH_2$, C≡C, CH=CH or NH, more especially a single bond;

(4) wherein $R_3$ is H, $C_1$–$C_6$alkyl or $C_1$–$C_6$haloalkyl, especially H or $C_1$–$C_6$alkyl, more especially H or $C_1$–$C_2$alkyl, especially H;

(5) wherein $X_1$ is halogen, $C_1$–$C_4$alkyl, $C_3$–$C_6$cycloalkyl, $C_1$–$C_4$haloalkyl, $C_1$–$C_4$alkoxy, $C_1$–$C_4$haloalkoxy, $C_1$–$C_4$alkylthio or $C_1$–$C_4$haloalkylthio; especially halogen, $C_1$–$C_2$alkyl, $C_1$–$C_2$haloalkyl, $C_1$–$C_2$alkoxy or $C_1$–$C_2$haloalkoxy; more especially fluorine, chlorine, methyl, trifluoromethyl or methoxy, especially fluorine or chlorine, more especially fluorine;

(6) wherein $X_2$ is H, halogen, $C_1$–$C_4$alkyl, $C_3$–$C_6$cycloalkyl, $C_1$–$C_4$haloalkyl, $C_1$–$C_4$alkoxy, $C_1$–$C_4$haloalkoxy, $C_1$–$C_4$alkylthio or $C_1$–$C_4$haloalkylthio; especially H, halogen, $C_1$–$C_2$alkyl, $C_1$–$C_2$haloalkyl, $C_1$–$C_2$alkoxy or $C_1$–$C_2$haloalkoxy; more especially fluorine, chlorine, methyl, trifluoromethyl or methoxy, especially fluorine or chlorine, more especially fluorine;

(7) wherein $X_3$ is H, halogen, $C_1$–$C_4$alkyl, $C_3$–$C_6$cycloalkyl, $C_1$–$C_4$haloalkyl, $C_1$–$C_4$alkoxy, $C_1$–$C_4$haloalkoxy, $C_1$–$C_4$alkylthio or $C_1$–$C_4$haloalkylthio; especially H, halogen, $C_1$–$C_2$alkyl, $C_1$–$C_2$haloalkyl, $C_1$–$C_2$alkoxy or $C_1$–$C_2$haloalkoxy; more especially fluorine, chlorine, methyl, trifluoromethyl or methoxy, especially H, fluorine or chlorine, preferably H;

(8) wherein the phenyl group substituted by $X_1$, $X_2$ and $X_3$ is in the 3-position on the triazine ring;

(9) wherein $R_1$ is an unsubstituted or mono- to tri-substituted aryl or heteroaryl ring, the substituents being selected from the group consisting of OH, halogen, CN, $NO_2$, $C_1$–$C_4$alkyl, $C_3$–$C_6$cycloalkyl, optionally substituted $C_5$–$C_6$cycloalkenyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsulfonyl, $C_1$–$C_4$haloalkylsulfonyl, optionally substituted $C_2$–$C_6$alkenyl, optionally substituted $C_2$–$C_6$alkynyl, $C_1$–$C_4$alkylcarbonyl, unsubstituted or mono- to penta-substituted phenyl, the substituents being selected from the group consisting of OH, halogen, CN, $NO_2$, $C_1$–$C_4$alkyl, $C_3$–$C_6$cycloalkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsulfonyl, $C_1$–$C_4$haloalkylsulfonyl, $C_2$–$C_6$alkenyl, $C_2$–$C_6$alkynyl and $C_1$–$C_4$alkylcarbonyl, unsubstituted or mono- to penta-substituted phenoxy, and unsubstituted or mono- to penta-substituted phenylamino, the substituents being selected from the group consisting of halogen, CN, $NO_2$, $C_1$–$C_4$alkyl, $C_3$–$C_6$cycloalkyl, $C_1$–$C_4$haloalkyl, $C_1$–$C_4$alkoxy, $C_1$–$C_4$haloalkoxy, $C_1$–$C_4$alkylthio, $C_1$–$C_4$haloalkylthio, $C_1$–$C_4$alkylsulfonyl and $C_1$–$C_4$haloalkylsulfonyl;

$R_2$ is H, halogen or $C_1$–$C_4$alkyl;

A is a single bond, $C_1$–$C_6$alkylene, O($C_1$–$C_6$alkylene), $C_2$–$C_4$alkenylene, $C_2$–$C_4$alkynylene or $NR_3$;

$R_3$ is H, $C_1$–$C_6$alkyl or $C_1$–$C_6$haloalkyl;

$X_1$ is halogen, $C_1$–$C_4$alkyl, $C_3$–$C_6$cycloalkyl, $C_1$–$C_4$haloalkyl, $C_1$–$C_4$alkoxy, $C_1$–$C_4$haloalkoxy, $C_1$–$C_4$alkylthio or $C_1$–$C_4$haloalkylthio;

$X_2$ and $X_3$ are each independently of the other H, halogen, $C_1$–$C_4$alkyl, $C_3$–$C_6$cycloalkyl, $C_1$–$C_4$haloalkyl, $C_1$–$C_4$alkoxy, $C_1$–$C_4$haloalkoxy, $C_1$–$C_4$alkylthio or $C_1$–$C_4$haloalkylthio; and the phenyl group substituted by $X_1$, $X_2$ and $X_3$ is in the 3-position on the triazine ring;

(11) wherein $R_1$ is mono- or di-substituted phenyl, the substituents being selected from the group consisting of halogen, CN, $NO_2$, $C_1$–$C_2$alkyl, $C_1$–$C_2$haloalkyl, $C_1$–$C_2$alkoxy, $C_1$–$C_2$haloalkoxy, unsubstituted or mono- or di-substituted phenyl, the substituents being selected from the group consisting of halogen, $C_1$–$C_2$alkyl, $C_1$–$C_2$haloalkyl, $C_1$–$C_2$alkoxy, $C_1$–$C_2$haloalkoxy, $C_1$–$C_2$alkylthio and $C_1$–$C_2$haloalkylthio, and phenoxy;

$R_2$ is H or $C_1$–$C_4$alkyl;

A is a single bond, O, $OCH_2$, C—C, CH=CH or NH;

$X_1$ is halogen, $C_1$–$C_2$alkyl, $C_1$–$C_2$haloalkyl, $C_1$–$C_2$alkoxy or $C_1$–$C_2$haloalkoxy;

$X_2$ and $X_3$ are each independently of the other H, halogen, $C_1$–$C_2$alkyl, $C_1$–$C_2$haloalkyl, $C_1$–$C_2$alkoxy or $C_1$–$C_2$haloalkoxy; and the phenyl group substituted by $X_1$, $X_2$ and $X_3$ is in the 3-position on the triazine ring;

(12) wherein $R_1$ is mono- or di-substituted phenyl, the substituents being selected from the group consisting of halogen, methyl, halomethyl, methoxy, halomethoxy, unsubstituted or mono- or di-substituted phenyl, the substituents being selected from the group consisting of halogen, methyl, halomethyl, methoxy, halomethoxy, methylthio and halomethylthio; and phenoxy;

$R_2$ is H;

A is a single bond;

$X_1$ is fluorine, chlorine, methyl, trifluoromethyl or methoxy;

$X_2$ and $X_3$ are each independently of the other H, fluorine, chlorine, methyl, trifluoromethyl or methoxy; and the phenyl group substituted by $X_1$, $X_2$ and $X_3$ is in the 3-position on the triazine ring;

in each case including the physiologically tolerable addition compounds.

(13) wherein the group A—$R_1$ is in the 6-position on the triazine ring.

Within the scope of the invention preference is given especially to the compounds of formula (I) listed in Tables 1 to 6 and more especially to the compounds of formula (I) mentioned in the Synthesis Examples.

The invention relates also to a process for the preparation of the compounds of formula (I), in each case in free form or in salt form, which comprises, for example, a) for the preparation of a compound of formula (I) wherein A is a single bond and the phenyl group substituted by $X_1$, $X_2$ and $X_3$ is in the 6-position on the triazine ring, reacting a compound of formula

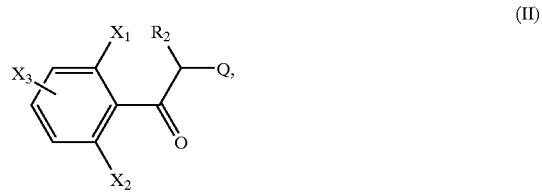

(II)

which is known or can be prepared analogously to corresponding known compounds and in which $X_1$, $X_2$, $X_3$ and $R_2$ are as defined for formula (I) and Q is a leaving group, with two equivalents of a compound of formula

(III)

which is known or can be prepared analogously to corresponding known compounds and in which $R_1$ is as defined for formula (I), optionally in the presence of a catalyst, preferably silver acetate, or b) for the preparation of a compound of formula (I) wherein A is a single bond and the phenyl group substituted by $X_1$, $X_2$ and $X_3$ is in the 3-position on the triazine ring, reacting two equivalents of a compound of formula

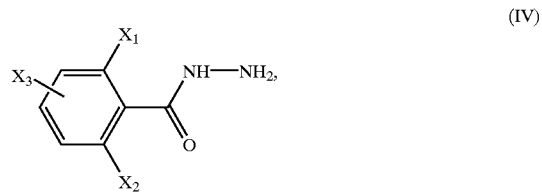

(IV)

which is known or can be prepared analogously to corresponding known compounds and in which $X_1$, $X_2$ and $X_3$ are as defined for formula (I), with one equivalent of a compound of formula

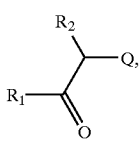 (V)

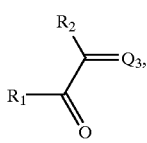 (IX)

which is known or can be prepared analogously to corresponding known compounds and in which $R_1$ and $R_2$ are as defined for formula (I) and $Q_1$ is a leaving group, optionally in the presence of a catalyst, preferably silver acetate, or c) for the preparation of a compound of formula (I) wherein A has the meanings defined for formula (I) with the exception of a single bond, reacting a compound of formula

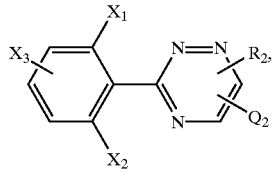 (VI)

which is known or can be prepared analogously to corresponding known compounds and in which $X_1$, $X_2$, $X_3$ and $R_2$ are as defined for formula (I) and $Q_2$ is a leaving group, with a compound of formula

$R_1$—A—M  (VII), which is known or can be prepared analogously to corresponding known compounds and in which $R_1$ is as defined for formula (I) and A has the meanings defined for formula (I) with the exception of S(O), S(O)($C_1$–$C_{12}$alkylene), S(O)$_2$ and S(O)$_2$($C_1$–$C_{12}$alkylene), and M is hydrogen, a transition metal or an alkali metal, and when A is S or S($C_1$–$C_{12}$alkylene), if desired oxidising the resulting product, optionally after intermediate isolation, for the preparation of a compound of formula (I) wherein A is S(O), S(O)($C_1$–$C_{12}$alkylene), S(O)$_2$ or S(O)$_2$($C_1$–$C_{12}$alkylene), or d) for the preparation of a compound of formula (i) wherein A is a single bond, oxidising a compound of formula

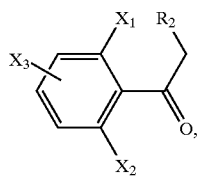 (VIII)

which is known or can be prepared analogously to corresponding known compounds and in which $X_1$, $X_2$, $X_3$ and $R_2$ are as defined for formula (I), with an oxidising agent and reacting the resulting product, optionally after intermediate isolation, with a compound of formula (III) and reacting the resulting product, optionally after intermediate isolation, with an ammonium salt, preferably ammonium acetate, or e) for the preparation of a compound of formula (I) wherein the phenyl group substituted by $X_1$, $X_2$ and $X_3$ is in the 3-position on the triazine ring, reacting a compound of formula which is known or can be prepared analogously to corresponding known compounds and in which $R_1$ and $R_2$ are as defined for formula (I) and $Q_3$ is O or NOH, with a compound of formula

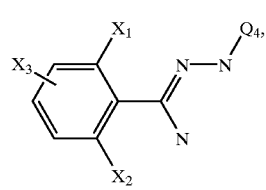 (X)

which is known or can be prepared analogously to corresponding known compounds and in which $X_1$, $X_2$ and $X_3$ are as defined for formula (I) and $Q_4$ is H or a protecting group capable of being removed, in free form or in salt form, or f) for the preparation of a compound of formula (I) wherein A is $C_1$–$C_{12}$alkylene, $C_2$–$C_8$alkenylene or $C_2$–$C_8$alkynylene, reacting a compound of formula (VI), which is known or can be prepared analogously to corresponding known compounds and in which $X_1$, $X_2$, $X_3$ and $R_2$ are as defined for formula (I) and $Q_2$ is $C_1$–$C_6$alkyl, preferably methyl, with a compound of formula

$R_1$—$C_1$–$C_{10}$alkyl-CHO  (XI), which is known or can be prepared analogously to corresponding known compounds and in which $R_1$ is as defined for formula (I), optionally in the presence of a strong base catalyst, preferably lithium diethylamide or butyllithium, and dehydrating the resulting product, optionally after intermediate isolation, optionally in the presence of a strong acid, and, if desired, for the preparation of a compound of formula (I) wherein A is $C_1$–$C_{12}$alkylene, carrying out hydrogenation in the presence of a hydrogenation catalyst, or for the preparation of a compound of formula (I) wherein A is $C_2$–$C_8$alkynylene, carrying out reaction with a halogen and then with a strong base, preferably NaOH; or g) for the preparation of a compound of formula (I) wherein the phenyl ring substituted by the substituents X is in the 3-position and $AR_1$ is in the 6-position, reacting a compound of formula

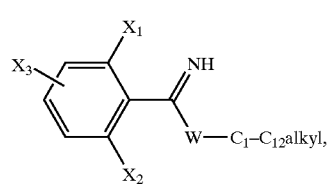 (XII)

which is known or can be prepared analogously to corresponding known compounds and in which $X_1$, $X_2$ and $X_3$ are as defined for formula (I) and W is O or S, or a salt thereof, with a compound of formula

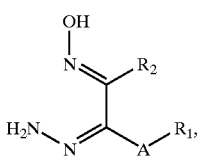

(XIII)

which is known or can be prepared analogously to corresponding known compounds and in which A, $R_1$ and $R_2$ are as defined for formula (I);

and in each case, if desired, converting a compound of formula (I), in each case in free form or in salt form, obtainable in accordance with the process or by another method into a different compound of formula (I), separating a mixture of isomers obtainable in accordance with the process and isolating the desired isomer and/or converting a free compound of formula (I) obtainable in accordance with the process into a salt or converting a salt of a compound of formula (I) obtainable in accordance with the process into the free compound of formula (I) or into a different salt.

The comments made above in connection with salts of compounds of formula (I) apply analogously, in respect of their salts, to starting materials mentioned hereinabove and hereinbelow.

In the individual process steps the reactants can be reacted with one another as such, that is to say without the addition of a solvent or diluent, for example in the molten state. Generally, however, it is advantageous to add an inert solvent or diluent or a mixture thereof.

Variant a):

Examples of solvents and diluents include: aromatic, aliphatic and alicyclic hydrocarbons and halogenated hydrocarbons, such as benzene, toluene, xylene, mesitylene, Tetralin, chlorobenzene, dichlorobenzene, bromobenzene, petroleum ether, hexane, cyclohexane, dichloromethane, trichloromethane, tetrachloromethane, dichloroethane, trichloroethene and tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran and dioxane; ketones, such as acetone, methyl ethyl ketone and methyl isobutyl ketone; alcohols, such as methanol, ethanol, propanol, isopropanol, butanol, ethylene glycol and glycerol; amides, such as N,N-dimethylformamide, N,N-diethylformamide, N,N-dimethylacetamide, N-methylpyrrolidone and hexamethylphosphoric acid triamide; nitriles, such as acetonitrile and propionitrile; and sulfoxides, such as dimethyl sulfoxide.

Preferred leaving groups are halogens, tosylates, mesylates and triflates, especially halogens, more especially chlorine.

The reaction is advantageously effected in a temperature range of from about 0° C. to about +150° C., preferably from about 20° C. to about +100° C.

In a preferred embodiment of variant a), a compound of formula (II) is reacted with a compound of formula (III) at from about 50° to about 100°, preferably about 85°, in an ether, preferably ethylene glycol dimethyl ether, in the presence of a catalyst, preferably silver acetate.

Variant b):

Examples of solvents and diluents are given under variant a).

Preferred leaving groups are halogens, tosylates, mesylates and triflates, especially halogens, more especially chlorine.

The reaction is advantageously effected in a temperature range of from about 0° C. to about +150° C., preferably from about 20° C. to about +100° C.

In a preferred embodiment of variant b), a compound of formula (IV) is reacted with a compound of formula (V) at from about 50° C. to about 100° C., preferably about 85°, in an ether, preferably ethylene glycol dimethyl ether, in the presence of a catalyst, preferably silver acetate.

Variant c):

Examples of solvents and diluents are given under variant a).

Preferred leaving groups are OH, halogens, tosylates, mesylates and triflates, especially halogens, more especially bromine and chlorine.

The reaction is advantageously effected in a temperature range of from about 0° C. to about +150° C., preferably from about 20° C. to about +100° C.

In a preferred embodiment of variant c), a compound of formula (VI) is reacted with a compound of formula (VII) at from about 0° to about 100°, preferably about 20°, in an inert solvent, optionally in the presence of a base as catalyst.

Variant d):

Examples of solvents and diluents are given under variant a).

Preferred oxidising agents are halogens, more especially bromine.

The reactions are advantageously effected in a temperature range of from about 0° C. to about +120° C., preferably from about 0° C. to about +80° C.

In a preferred embodiment of variant d), a compound of formula (VII) is oxidised with bromine at from about 0° to about 100°, preferably about 80°, in a polar solvent, preferably DMSO/water, and then, after intermediate isolation of the resulting diketo compound, reacted with a compound of formula (III) at from about 0° to about 60°, preferably about 20°, in a polar solvent, preferably an alcohol, and then, preferably without intermediate isolation, reacted with ammonium acetate at from about 0° to about 120°, preferably about 100°, in a polar solvent, preferably glacial acetic acid.

Variant e):

Examples of solvents and diluents are given under variant a).

Preferred protecting groups are $C_1$–$C_6$alkoxycarbonyl.

The reactions are advantageously effected in a temperature range of from about 0° C. to about +150° C., preferably from about 0° C. to about +120° C.

In a preferred embodiment of variant e), a compound of formula (IX) is reacted with a compound of formula (X) at from about 0° to about 100°, preferably about 20°, in an alcohol, preferably ethanol or an ethanol/water mixture, optionally in the presence of an acid catalyst, preferably formic acid.

Variant f):

Examples of solvents and diluents are given under variant a).

The reactions are advantageously effected in a temperature range of from about –80° C. to about +150° C., preferably from about 0° C. to about +110° C.

In a preferred embodiment of variant f), a compound of formula (VI) wherein $Q_2$ is methyl is reacted with an aldehyde of formula (XI) at from about –80° C. to about 0° C., preferably about –70° C., in a non-polar solvent, preferably tetrahydrofuran, in the presence of a strong base, preferably n-butyllithium, and then, preferably after intermediate isolation, reacted with a strong acid, preferably toluenesulfonic acid, at from about 80° C. to about 150° C., preferably at the boiling temperature of the solvent, in a non-polar solvent, preferably toluene.

Variant g):

Examples of solvents and diluents are given under variant a); alcohols, such as methanol, ethanol and n-propanol, and also amides, such as dimethylformamide and dimethylacetamide, are especially suitable.

The reactions are advantageously effected in a temperature range of from about room temperature to the boiling point of the solvent used, preferably from about 60° C. to about +100° C.

In a preferred embodiment of variant g), a compound of formula (XII) wherein W is S is reacted with a compound of formula (XIII) at from about 25° C. to about 100° C., preferably at about 100° C., in an alcohol, preferably in n-propanol.

Salts of compounds of formula (I) can be prepared in a manner known per se. For example, acid addition salts of compounds of formula (I) are obtained by treatment with a suitable acid or a suitable ion exchange reagent and salts with bases by treatment with a suitable base or a suitable ion exchange reagent.

Salts of compounds of formula (I) can be converted into the free compounds of formula (I) in customary manner; acid addition salts, for example, by treatment with a suitable basic agent or a suitable ion exchange reagent and salts with bases, for example, by treatment with a suitable acid or a suitable ion exchange reagent.

Salts of compounds of formula (I) can be converted in a manner known per se into other salts of compounds of formula (I); acid addition salts can be converted, for example, into other acid addition salts, for example by treatment of a salt of an inorganic acid, such as a hydrochloride, with a suitable metal salt, such as a sodium, barium or silver salt, of an acid, for example with silver acetate, in a suitable solvent in which an inorganic salt that forms, for example silver chloride, is insoluble and thus precipitates out from the reaction mixture.

Depending upon the procedure and reaction conditions, compounds of formula (I) having salt-forming properties may be obtained in free form or in the form of salts.

The compounds of formula (I) may also be obtained in the form of solvates, especially in the form of their hydrates.

The invention relates to all those forms of the process in which a compound obtainable as starting compound or intermediate at any stage of the process is used as starting material and all or some of the remaining steps are carried out or a starting material is used in the form of a derivative or salt or, especially, is formed under the reaction conditions.

In the process of the present invention it is preferable to use those starting materials and intermediates which result in the compounds of formula (I) described at the beginning as being especially valuable.

The invention relates especially to the processes described in the Preparation Examples.

The invention relates also to novel starting materials and intermediates, in each case in free form or in salt form, used according to the invention for the preparation of the compounds of formula (I) and their salts, to their use and to processes for their preparation.

In the area of pest control, the compounds of formula (I) according to the invention are active ingredients exhibiting valuable preventive and/or curative activity with a very advantageous biocidal spectrum, even at low rates of concentration, while being well tolerated by warm-blooded animals, fish and plants. The active ingredients according to the invention are effective against all or individual development stages of normally sensitive animal pests, but also of resistant animal pests, such as insects and representatives of the order Acarina. The insecticidal, ovicidal and/or acaricidal action of the active ingredients according to the invention may manifest itself directly, i.e. in the mortality of the pests, which occurs immediately or only after some time, for example during moulting, or of their eggs, or indirectly, for example in reduced oviposition and/or hatching rate, good activity corresponding to a mortality of at least 50 to 60%.

The said animal pests include, for example, those mentioned in European Patent Application EP-A-736 252. The pests listed therein are therefore included by reference in the subject matter of the present invention; representatives of the order Acarina are especially

*Acarus siro, Aceria sheldoni, Aculus schlechtendali*, Amblyomma spp., Argas spp., Boophilus spp., Brevipalpus spp., *Bryobia praetiosa*, Calipitrimerus spp., Chorioptes spp., *Dermanyssus gallinae, Eotetranychus carpini*, Eriophyes spp., Hyalomma spp., Ixodes spp., *Olygonychus pratensis*, Ornithodoros spp., Panonychus spp., *Phyllocoptruta oleivora, Polyphagotarsonemus latus*, Psoroptes spp., Rhipicephalus spp., Rhizoglyphus spp., Sarcoptes spp., Tarsonemus spp. and Tetranychus spp.

The compounds according to the invention can be used to control, i.e. to inhibit or destroy, pests of the mentioned type occurring especially on plants, more especially on useful plants and ornamentals in agriculture, in horticulture and in forestry, or on parts of such plants, such as the fruits, blossoms, leaves, stems, tubers or roots, while in some cases parts of plants that grow later are still protected against those pests.

Target crops include both natural crops and crops that have been modified by breeding or genetic methods, especially cereals, such as wheat, barley, rye, oats, rice, maize and sorghum; beet, such as sugar beet and fodder beet; fruit, e.g. pomes, stone fruit and soft fruit, such as apples, pears, plums, peaches, almonds, cherries and berries, e.g. strawberries, raspberries and blackberries; leguminous plants, such as beans, lentils, peas and soybeans; oil plants, such as rape, mustard, poppy, olives, sunflowers, coconut, castor oil, cocoa and groundnuts; cucurbitaceae, such as marrows, cucumbers and melons; fibre plants, such as cotton, flax, hemp and jute; citrus fruits, such as oranges, lemons, grapefruit and mandarins; vegetables, such as spinach, lettuce, asparagus, cabbages, carrots, onions, tomatoes, potatoes and paprika; lauraceae, such as avocado, cinnamon and camphor; and tobacco, nuts, coffee, aubergines, sugar cane, tea, pepper, vines, hops, bananas, natural rubber plants and ornamentals.

The compounds according to the invention are especially suitable for controlling insects and representatives of the order Acarina, especially plant-destructive feeding insects, such as *Anthonomus grandis, Diabrotica balteata, Heliothis virescens* larvae, *Plutella xylostella* and *Spodoptera littoralis* larvae, and spider mites, such as *Tetranychus* spp., in cotton, fruit, citrus, maize, soybean, rape and vegetable crops.

Further areas of use of the compounds according to the invention are the protection of stored goods and stocks and of material, and also in the hygiene sector, especially in the protection of warm-blooded animals, including farm animals, such as cows, pigs, sheep and goats, poultry, such as hens, turkeys and geese, animals bred for their fur, such as mink, foxes, chinchillas, rabbits and the like, and also domestic animals and pets, such as cats and dogs, and even human beings, against pests of the mentioned type.

For example, flea infestation in domestic animals and pets is a problem for the animal owner to which there have as yet been found only unsatisfactory solutions. Owing to the complicated life cycle of the flea, none of the known methods of controlling fleas is totally satisfactory, especially since most of the known methods are aimed principally at controlling the fully grown fleas in the coat and take no account at all of the various juvenile stages of the fleas, which live not only in the animal's coat, but also on the floor, on carpets, on the animal's sleeping place, on chairs, in the garden and in all the other places with which the infested animal comes into contact. Flea treatment is generally expensive and must be continued for a prolonged period, success generally only being achieved when the treatment is applied not only to the affected animal, e.g. the dog or cat, but also simultaneously to any places frequented by the affected animal.

The compounds of formula (I) according to the invention can be used alone or in combination with other biocides. For example, in order to increase the effect they can be combined with pesticides having the same direction of action or in order to broaden the spectrum of action they can be combined with substances having a different direction of action. Where it is desired to extend the spectrum of action to endoparasites, e.g. worms, the compounds of formula (I) are advantageously combined with substances having endoparasiticidal properties. They can of course also be used in combination with anti-bacterial agents. Since the compounds of formula (I) are "adulticides", that is to say they are effective especially against the fully grown stages of the target parasites, the addition of pesticides that are more effective against the juvenile stages of the parasite may be very advantageous, since in this way the entire spectrum of the parasite population will be reached and, furthermore, a substantial contribution is made to avoiding the development of resistance.

The good pesticidal activity of the compounds of formula (I) according to the invention corresponds to a mortality of at least 50–60% of the mentioned pests.

The action of the compounds according to the invention and the compositions comprising them against animal pests can be significantly broadened and adapted to the given circumstances by the addition of other insecticides and/or acaricides. Suitable additives include, for example, representatives of the following classes of active ingredient: organophosphorus compounds, nitrophenols and derivatives, formamidines, thioureas, benzoylureas, carbamates, pyrethroids, neonicotinoids, chlorinated hydrocarbons and Bacillus thuringiensis preparations.

Especially suitable mixing partners are: Azamethiphos; Chlorfenvinphos; Cypermethrin, Cypermethrin high-cis; Cyromazin; Diafenthiuron; Diazinon; Dichlorvos; Dicrotophos; Dicyclanil; Fenoxycarb; Fluazuron; Furathiocarb; Isazofos; Jodfenphos; Kinoprene; Lufenuron; Methacriphos; Methidathion; Monocrotophos; Phosphamidon; Profenofos; Diofenolan; o compound obtainable from *Bacillus thuringiensis* strain GC91 or from NCTC11821; Pymetrozine; Bromopropylate; Methoprene; Disulfuton; Quinalphos; Tau-Fluvalinate; Thiocyclam; Thiometon; Aldicarb; Azinphosmethyl; Benfuracarb; Bifenthrin; Buprofezin; Carbofuran; Cartap; Chlorfluazuron; Chlorpyrifos; Cyfluthrin; Lambda-Cyhalothrin; Alpha-cypermethrin; zeta-Cypermethrin; Deltamethrin; Diflubenzuron; Endosulfan; Ethiofencarb; Fenitrothion; Fenobucarb; Fenvalerate; Formothion; Methiocarb; Heptenophos; Imidacloprid; Isoprocarb; Methamidophos; Methomyl; Mevinphos; Parathion; Parathion-methyl; Phosalone; Pirimicarb; Propoxur; Teflubenzuron; Terbufos; Triazamate; Abamectin; Fenobucarb; Tebufenozide; Fipronil; beta-Cyfluthrin; Silafluofen; Fenpyroximate; Pyridaben; Fenazaquin; Pyriproxyfen; Pyrimidifen; Nitenpyram; NI-25, Acetamiprid; Avermectin $B_1$ (Abamectin); an insecticidally active extract of a plant; a preparation containing a nematocidally active component; a compound obtainable from Bacillus subtilis; a preparation containing insecticidally active fungi; a preparation containing an insecticidally active virus; AC 303 630; Acephate; Acrinathrin; Alanycarb; Alphamethrin; Amitraz; AZ 60541; Azinphos A; Azinphos M; Azocyclotin; Bendiocarb; Bensultap; Betacyfluthrin; BPMC; Brofenprox; Bromophos A; Bufencarb; Butocarboxin; Butylpyridaben; Cadusafos; Carbaryl; Carbophenothion; Chloethocarb; Chlorethoxyfos; Chlormephos; Cis-Res-methrin; Clocythrin; Clofentezin; Cyanophos; Cycloprothrin; Cyhexatin; Demeton M; Demeton S; Demeton-S-methyl; Dichlofenthion; Dicliphos; Diethion; Dimethoat; Dimethylvinphos; Dioxathion; Edifenphos; Emamectin; Esfenvalerat; Ethion; Ethofenprox; Ethoprophos; Etrimphos; Fenamiphos; Fenbutatinoxid; Fenothiocarb; Fenpropathrin; Fenpyrad; Fenthion; Fluazinam; Flucycloxuron; Flucythrinat; Flufenoxuron; Flufenprox; Fonophos; Fosthiazat; Fubfenprox; HCH; Hexaflumuron; Hexythiazox; Iprobenfos; Isofenphos; Isoxathion; Ivermectin; Lambda-cyhalothrin; Malathion; Mecarbam; Mesulfenphos; Metaldehyd; Metolcarb; Milbemectin; Moxidectin; Naled; NC 184; Omethoat; Oxamyl; Oxydemethon M; Oxydeprofos; Permethrin; Phenthoat; Phorat; Phosmet; Phoxim; Pirimiphos M; Pirimiphos A; Promecarb; Propaphos; Prothiofos; Prothoat; Pyrachlophos; Pyradaphenthion; Pyresmethrin; Pyrethrum; RH 5992; Salithion; Sebufos; Sulfotep; Sulprofos; Tebufenpyrad; Tebupirimphos; Tefluthrin; Temephos; Terbam; Tetrachlor-vinphos; Thiacloprid; Thiamethoxam; Thiafenox; Thiodicarb; Thiofanox; Thionazin; Thuringiensin; Tralomethrin; Triarthen; Triazophos; Triazuron; Trichlorfon; Triflumuron; Trimethacarb; Vamidothion; Xylylcarb; YI 5301/5302; Zetamethrin; DPX-MP062; RH-2485; D 2341 or XMC (3,5,-Xy-lyl Methylcarbamate).

The compounds of formula (I) are used in unmodified form or, preferably, together with the adjuvants conventionally employed in formulation technology and can therefore be formulated in known manner e.g. into emulsifiable concentrates, directly sprayable or dilutable solutions, dilute emulsions, wettable powders, soluble powders, dusts, granules, and also encapsulations in polymer substances.

The formulations, that is to say the compositions, preparations or mixtures comprising the compound (active ingredient) of formula (I), or a combination of that active ingredient with other agrochemical active ingredients and, as appropriate, a solid or liquid adjuvant, are prepared in known manner, e.g. by homogeneously mixing and/or grinding the active ingredients with extenders, for example with solvents, solid carriers, and optionally surface-active compounds (surfactants) and the invention relates also thereto.

The invention relates also to the methods of application of the compositions, i.e. the methods of controlling pests of the mentioned type, such as spraying, atomising, dusting, coating, dressing, scattering or pouring, which are selected in accordance with the intended objectives and the prevailing circumstances, and to the use of the compositions for controlling pests of the mentioned type. Typical rates of concentration are from 0.1 to 1000 ppm, preferably from 0.1 to 500 ppm, of active ingredient. The rates of application per hectare are generally from 1 to 2000 g of active ingredient per hectare, especially from 10 to 1000 g/ha, preferably from 20 to 600 g/ha.

A preferred method of application in the area of plant protection is application to the foliage of the plants (foliar application), the frequency and the rate of application being dependent upon the risk of infestation by the pest in question. However, the active ingredient can also penetrate the plants through the roots (systemic action) by impregnating the locus of the plants with a liquid formulation or by incorporating the active ingredient in solid form into the locus of the plants, for example into the soil, e.g. in granular form (soil application). In the case of paddy rice crops, such granules may be applied in metered amounts to the flooded rice field.

The crop protection agents of the invention are also suitable for protecting vegetative reproductive material, e.g. seeds, such as fruits, tubers or grains, or plant seedlings, from animal pests. The reproductive material can be treated with the composition before the start of cultivation, seeds for example being dressed before they are sown. The active ingredients of the invention can also be applied to seeds (coating) by either soaking the seeds in a liquid composition or coating them with a solid composition. The composition can also be given when the reproductive material is introduced to the place of cultivation, e.g. when the seeds are sown in the seed furrow. The treatment procedures for vegetative reproductive material and the vegetative reproductive material thus treated are further objects of the invention.

As formulation auxiliaries there are used, for example, solid carriers, solvents, stabilisers, "slow release" auxiliaries, dyes and optionally surface-active substances (surfactants). Suitable carriers and auxiliaries include all those substances customarily used in plant protection compositions. Suitable auxiliaries, such as solvents, solid carriers, surface-active compounds, non-ionic surfactants, cationic surfactants, anionic surfactants and other auxiliaries in the compositions used according to the invention, include e.g. those described in EP-A-736 252; they are included by reference in the subject matter of the present invention.

Suitable anionic surfactants include both so-called water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tall oil. Mention may also be made of fatty acid methyltaurine salts as surfactants.

More frequently, however, so-called synthetic surfactants are used, as mentioned in EP-A-736 252, especially fatty sulfonates, fatty sulfates, sulfonated benzimidazole derivatives and alkylarylsulfonates.

The compounds of formula (I) are distinguished inter alia also by excellent activity against fleas, not only adult fleas being rapidly killed but also, by a circuitous route, the juvenile stages of the fleas. Flea larvae hatching out from the flea eggs feed substantially on the excreta of the adult fleas. Since the compounds of formula (I) according to the invention kill the adult fleas very rapidly, the necessary excreta are missing and the juvenile stages are deprived of the nutrient medium, so that they perish before reaching the adult stage.

The present invention therefore relates preferably to a method of controlling parasites on human beings, domestic animals, productive livestock and pets, wherein an effective amount of a composition comprising at least one compound of formula (I), or a physiologically tolerable salt thereof, is administered systemically or, preferably, topically to the warm-blooded animal.

The long-term action is achieved by the compounds of formula (I) according to the invention with various forms of administration, for example by administering the active ingredient in a formulated form externally or internally to the animal to be treated. "Formulated" in this case means, for example, in the form of a powder, a tablet or granules, in liposomes or a capsule, in the form of an emulsion, a foam or a spray, in microencapsulated form or in pour-on or spot-on form. It will be understood that all orally administrable compositions comprise, in addition to customary formulation substances, further additives that encourage the host animal to take the composition orally voluntarily, e.g. suitable odorants and flavourings.

Percutaneous administration, e.g. by subcutaneous or intramuscular injection or as a depot preparation in the form of an implant, and topical application, for example in pour-on or spot-on form, represent preferred subjects of this invention on account of their being easy to carry out. A further mode of administration is oral administration, e.g. in the form of a tablet. Percutaneous and topical forms of administration are of particular interest and give excellent results.

Percutaneous forms of administration include, for example, subcutaneous, intramuscular and even intravenous administration of injectable forms. In addition to the customary syringes with needles, it is also possible to use needle-less high-pressure syringe devices.

Pour-on and spot-on formulations are especially preferred as topical forms of administration, but administration in the form of sprays, ointments, solutions or powders may also be expedient.

By selection of a suitable formulation, it is possible to enhance the ability of the active ingredients to penetrate the living tissue of the host animal and/or to maintain their availability. That is important when, for example, more sparingly soluble active ingredients are used, the low solubility of which requires means for enhancing solubility, since in such cases the animal's body fluid is capable of dissolving only small amounts of active ingredients at a time.

Furthermore, in order to obtain a strongly delayed release of active ingredient, a compound of formula (I) according to the invention may also be present in a matrix formulation which physically prevents the active ingredient from being released and excreted prematurely and maintains the bioavailability of the active ingredient. Such a matrix formulation is injected into the body, e.g. intramuscularly or subcutaneously, and remains there as a form of depot from which the active ingredient is released continuously. Such matrix formulations are known to a person skilled in the art. They are generally wax-like, semi-solid substances, for example vegetable waxes and polyethylene glycols having a high molecular weight, or solid polymer formulations, for example so-called microspheres.

The rate of release of the active ingredient from the implant and thus the period of time over which the implant exhibits an action is generally determined by the accuracy with which the implant has been calibrated (amount of active ingredient in the implant), the environment around the implant and the polymer formulation from which the implant has been made.

The administration of veterinary medicinal additives to animal feed is well known in the field of animal health. It is usual first to prepare a so-called premix in which the active ingredient is dispersed in a liquid or is in finely divided form in solid carriers. That premix can normally comprise about 1 to 800 mg of compound per kg of premix, depending on the desired final concentration in the food.

Since the compounds of formula (I) according to the invention may be hydrolysed by the constituents of the food, they should be formulated in a protective matrix, for example in gelatin, before being added to the premix.

The present invention accordingly relates also to the aspect of controlling parasites by administering to the host animal with its food a compound of formula (I) that has been protected against hydrolysis.

A compound of formula (I) according to the invention is advantageously administered in a dose of from 0.01 to 800 mg/kg, preferably from 0.1 to 200 mg/kg, especially from 0.5 to 30 mg/kg, body weight, based on the host animal.

A good dose that can be routinely administered to the host animal is from 0.5 to 100 mg/kg, especially from 0.1 to 40 mg/kg, body weight. The administration is effected at suitable intervals in dependence upon the mode of administration and body weight.

The total dose may vary from one species of animal to another and also within a species of animal for the same active ingredient, since it depends inter alia on the weight, age and constitution of the host animal.

When used according to the invention, the compound of formula (I) according to the invention will normally be administered not in pure form but, preferably, in the form of a composition that comprises, in addition to the active ingredient, constituents that assist administration, suitable constituents being those that are tolerated by the host animal. It is of course possible, as well as controlling the adult parasites in accordance with the invention, additionally to use conventional methods to control the juvenile stages of the fleas, although the latter is not absolutely essential.

Such compositions to be administered in accordance with the invention generally comprise from 0.1 to 99% by weight, especially from 0.1 to 95% by weight, of a compound of formula (I) according to the invention and from 99.9 to 1% by weight, especially from 99.9 to 5% by weight, of a solid or liquid, physiologically tolerable carrier, including from 0 to 25% by weight, especially from 0.1 to 25% by weight, of a non-toxic dispersant.

Whereas commercial products will preferably be formulated as concentrates, the end user will normally employ dilute formulations.

Such formulations may also comprise further auxiliaries, such as stabilisers, antifoams, viscosity regulators, binders and tackifiers as well as other active ingredients for obtaining special effects.

The physiologically tolerable carriers known from veterinary medicinal practice for oral, percutaneous and topical administration can be used as formulation auxiliaries. Some examples are given below.

Suitable carriers are especially fillers, such as sugars, e.g. lactose, saccharose, mannitol or sorbitol, cellulose preparations and/or calcium phosphates, for example tricalcium phosphate or calcium hydrogen phosphate, and binders, such as starch pastes using, for example, maize, wheat, rice or potato starch, gelatin, tragacanth, methylcellulose and/or, if desired, disintegrators, such as the above-mentioned starches, also carboxymethyl starch, cross-linked polyvinylpyrrolidone, agar, alginic acid or a salt thereof, such as sodium alginate. Adjuvants are especially flow conditioners and lubricants, for example silicic acid, talc, stearic acid or salts thereof, such as magnesium or calcium stearate, and/or polyethylene glycol. Dragée cores can be provided with suitable, optionally enteric, coatings, there being used inter alia concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes, flavourings or pigments may be added to the tablets or dragee coatings, for example for identification purposes or to indicate different doses of active ingredient.

Other orally administrable preparations are hard gelatin capsules, and also soft sealed capsules made of gelatin and a plasticiser, such as glycerol or sorbitol. The hard gelatin capsules may comprise the active ingredient in the form of granules, for example in admixture with fillers, such as lactose, binders, such as starches, and/or glidants, such as talc or magnesium stearate, and, if desired, stabilisers. In soft capsules, the active ingredient is preferably dissolved or suspended in suitable liquids, such as fatty oils, paraffin oil or liquid polyethylene glycols, to which stabilisers may likewise have been added. Preference is given inter alia to capsules that may either easily be bitten through or swallowed without being chewed.

The pour-on or spot-on method comprises applying the compound of formula (I) to a locally defined area of the skin or coat, advantageously on the back of the neck or the backbone of the animal. This is carried out, for example, by applying a swab or spray of the pour-on or spot-on formulation to a relatively small area of the coat from where the active ingredient becomes distributed over a wide area of the coat almost automatically as a result of the spreading constituents of the formulation assisted by the movements of the animal.

Pour-on and spot-on formulations advantageously comprise carriers that assist rapid distribution over the surface of the skin and in the coat of the host animal and are generally termed spreading oils. There are suitable, for example, oily solutions; alcoholic and isopropanolic solutions, e.g. solutions of 2-octyl dodecanol or oleyl alcohol; solutions in esters of monocarboxylic acids, such as isopropyl myristate, isopropyl palmitate, lauric acid oxalic ester, oleic acid oleyl ester, oleic acid decyl ester, hexyl laurate, oleyl oleate, decyl oleate, caproic acid esters of saturated fatty alcohols of chain length $C_{12}$–$C_{18}$; solutions of esters of dicarboxylic acids, such as dibutyl phthalate, diisopropyl isophthalate, adipic acid diisopropyl ester, di-n-butyl adipate or solutions of esters of aliphatic acids, e.g. glycols. It may be advantageous for a dispersant known from the pharmaceutical or cosmetic industry also to be present. Examples are pyrrolidin-2-one, N-alkylpyrrolidin-2-one, acetone, polyethylene glycol and its ethers and esters, propylene glycol or synthetic triglycerides.

The oily solutions include e.g. vegetable oils, such as olive oil, groundnut oil, sesame oil, pine oil, linseed oil and castor oil. The vegetable oils may also be in epoxidised form. It is also possible to use paraffins and silicone oils.

Generally a pour-on or spot-on formulation will contain from 1 to 20% by weight of a compound of formula (I), from 0.1 to 50% by weight dispersant and from 45 to 98.9% by weight solvent.

The pour-on or spot-on method can be used especially advantageously for herd animals, such as cattle, horses, sheep and pigs, where it is difficult or time-consuming to treat all the animals orally or via injection. By virtue of its simplicity, this method can of course also be used for all other animals, including individual domestic animals and pets, and is very popular with the keepers of the animals because it can often be carried out without the expert assistance of a veterinary surgeon.

Suitable for parenteral and percutaneous administration are oily injection solutions or suspensions, there being used suitable lipophilic solvents or vehicles, such as fatty oils, for example sesame oil, or synthetic fatty acid esters, for example ethyl oleate, or triglycerides, or aqueous injection solutions or suspensions that comprise viscosity-increasing substances, for example sodium carboxymethylcellulose, sorbitol and/or dextran, and, optionally, stabilisers.

The preparations of the present invention can be prepared in a manner known per se, for example by means of conventional mixing, granulating, confectioning, dissolving or lyophilising processes. For example, pharmaceutical preparations for oral administration can be obtained by combining the active ingredient with solid carriers, optionally granulating the resulting mixture, and processing the mixture or granules, if desired or necessary after the addition of suitable excipients, to form tablets or dragee cores.

The following Examples serve merely to illustrate the invention and do not limit the invention.

Preferred formulations have especially the following composition (throughout, percentages are by weight):

| Emulsifiable concentrates: | |
| --- | --- |
| active ingredient: | 1 to 90%, preferably 5 to 20% |
| surface-active agent: | 1 to 30%, preferably 10 to 20% |
| liquid carrier: | 5 to 94%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.5 to 30%, preferably 3 to 15% |
| solid carrier: | 99.5 to 70%, preferably 97 to 85% |
| Injection solution: | |
| active ingredient: | 0.1 to 10%, preferably 0.5 to 5% |
| non-ionic surfactant: | 0.1 to 30%, preferably 0.5 to 10% |
| mixture of ethanol and propylene glycol | 60 to 99%, preferably 85 to 90% |
| Injection suspension (aqueous or oily): | |
| active ingredient: | 0.1 to 20%, preferably 1 to 10% |
| non-ionic surfactant: | 0.1 to 20%, preferably 1 to 10% |
| water or vegetable oil: | 60 to 99%, preferably 85 to 95% |

The compositions may also comprise further ingredients, such as stabilisers, e.g. vegetable oils or epoxidised vegetable oils (epoxidised coconut oil, rape oil or soybean oil), antifoams, e.g. silicone oil, preservatives, viscosity regulators, binders and tackifiers as well as fertilisers or other active ingredients for obtaining special effects.

The following Examples illustrate the invention described above but do not limit the scope thereof in any way. Temperatures are given in degrees Celsius. The symbol 'h' stands for 'hour'.

1. SYNTHESIS EXAMPLES

Example 1.1

3-(4-Bromophenyl)-6-(2,6-difluorophenyl)-[1,2,4]triazine a) 40.6 g of 2,6-difluoroacetophenone are placed in 120 ml of chloroform, and 0.1 g of aluminium chloride is added. Then, at 0° C., 37 g of bromine in 240 ml of chloroform are added dropwise and stirring is carried out at 0° C. for 1 h. The reaction mixture is then heated to room temperature and is concentrated using a rotary evaporator. The residue is distilled over a Vigreux column. In this way 2-bromo-1-(2,6-difluorophenyl)-ethanone having a boiling point of 101–11° C. at 9 mbar is obtained.

b) 24.2 g of 4-bromobenzoic acid hydrazide and 9.17 g of silver acetate are placed in 290 ml of dimethoxyethane. The brown suspension is heated at 60° C., 12.9 g of 2-bromo-1-(2,6-di-fluorophenyl)-ethanone are added and stirring is then carried out, with reflux cooling (about 85° C.), for 48 h. The suspension is cooled to 40° C. and filtered, and the filtrate is concentrated using a rotary evaporator. The crude product is purified by means of flash chromatography (silica gel; dichloromethane/n-hexane 1:1). In this way the title compound having a melting point of 167–169° C. is obtained.

Example 1.2

6-(2,6-Difluorophenyl)-3-(4'-trifluoromethoxybiphenyl-4-yl)-[1,2,4]triazine 244 mg of 3-(4-bromophenyl)-6-(2,6-difluorophenyl)-[1,2,4]triazine are placed in 1.8 ml of 1,2-dimethoxyethane, and 2.5 mg of bis(triphenylphosphine)palladium(II) dichloride, 159 mg of 4-trifluoromethoxyphenylboric acid and 176 mg of sodium hydrogen carbonate in 1.8 ml of water are added in succession. The reaction mixture is then heated at 70° C. for 5 h. After cooling to room temperature, the suspension is poured into 1N sodium hydroxide solution and extracted with ethyl acetate. The organic phase is washed with saturated sodium chloride solution, dried over sodium sulfate, filtered and concentrated. The crude product is dissolved in a minimum of hot ethyl acetate, filtered clear and crystallised at 0° C. In this way the title compound having a melting point of 199–202° C. is obtained.

Example 1.3

6-(4-Bromophenyl)-3-(2,6-difluorophenyl)-[1,2,4]triazine a) Under nitrogen, 3.15 g of methylthio-2,6-difluorobenzimidinium iodide are dissolved in 30 ml of absolute methanol, and 1.32 g of tert-butyl carbazate are added. After being stirred at room temperature for 17 hours the reaction mixture is concentrated using a rotary evaporator and the residue is dried under a high vacuum. In this way N'-[(2,6-difluorophenyl)-iminomethyl]-hydrazinecarboxylic acid tert-butyl ester is obtained in the form of a yellowish foam, which is reacted further without further purification.

b) 19.9 g of 4-bromoacetophenone are placed in 150 ml of methanol under nitrogen, and 14.7 ml of isopentyl nitrite are added. To the resulting solution there are then added dropwise, at 17–23° C., 22.2 ml of a 5.4M solution of sodium methanolate in methanol. After 70 hours' stirring at room temperature the orange suspension is concentrated using a rotary evaporator. 300 ml of water are added to the residue, and the mixture is rendered acidic with 60 ml of 2N hydrochloric acid. The resulting yellow suspension is filtered and washed with water; the filter cake is taken up in ethyl acetate and washed with water. The organic phase is washed with saturated sodium chloride solution, dried over sodium sulfate, filtered and concentrated. The crude product is recrystallised from ethyl acetate/toluene. In this way (4-bromophenyl)-oxoacetaldehyde oxime is obtained in the form of a colourless powder.

c) A mixture of 200 mg of N'-[(2,6-difluorophenyl)-iminomethyl]-hydrazinecarboxylic acid tert-butyl ester, 114 mg of (4-bromophenyl)-oxoacetaldehyde oxime and 123 mg of sodium acetate in 1.5 ml of glacial acetic acid is heated at 10° C. for 3 h. After cooling to room temperature, the reaction mixture is poured into water and extracted with ethyl acetate. The organic phase is washed in succession with saturated sodium hydrogen carbonate solution and saturated sodium chloride solution, dried over sodium sulfate, filtered and concentrated. The residue is purified by means of flash chromatography (1% methanol in dichloromethane). In this way the title compound having a melting point of 180–181° C. is obtained.

Example 1.4

3-(2,6-Difluorophenyl)-6-(4'-trifluoromethoxybiphenyl-4-yl)-[1,2,4]triazine

Analogously to the procedure indicated in Example 1.2, the title compound having a melting point of 225–230° C. is obtained by Pd-catalysed coupling of 6-(4-bromophenyl)-3-(2,6-di-fluorophenyl)-[1,2,4]triazine with 4-trifluoromethoxyphenylboric acid.

Example 1.5

3-(4-Bromophenyl)-5-(2,6-difluorophenyl)-[1,2,4]triazine a) 5 g of 2,6-difluoroacetophenone are placed in 13.6 ml of DMSO, and 2.7 ml of bromine (8.8M in water) are added dropwise, the reaction temperature rising from room temperature to 40° C. When the addition of bromine is complete, the mixture is heated at 80° C. for 30 min. After cooling to room temperature, the reaction mixture is poured into 100 ml of dichloromethane; with stirring, sodium sulfate and solid sodium hydrogen carbonate are added to the solution, filtration is carried out and the reaction mixture is concentrated using a rotary evaporator. The crude product is subjected to flash chromatography with dichloromethane. In this way (2,6-difluorophenyl)-oxoacetaldehyde is obtained in the form of a colourless viscous oil.

b) 2 g of (2,6-difluorophenyl)-oxoacetaldehyde are placed in 15 ml of methanol at room temperature, and 1.59 g of 4-bromophenyl hydrazide are added, the latter dissolving completely. After stirring at room temperature for 2 h, the precipitated product is filtered off and then washed with a small amount of cold methanol. In this way, 4-bromobenzoic acid [2-(2,6-difluorophenyl)-2-oxoethylidene] hydrazide is obtained and is reacted further without further purification.

c) A mixture of 1.85 g of 4-bromobenzoic acid [2-(2,6-difluorophenyl)-2-oxoethylidene] hydrazide and 0.77 g of ammonium acetate is heated in 15 ml of glacial acetic acid at 10° C. for 14 h. After cooling to room temperature, the reaction mixture is poured into ice-water and extracted with ethyl acetate, and the organic phase is washed with saturated sodium hydrogen carbonate and saturated sodium chloride solution. After the organic phase has been dried over sodium sulfate, filtering and concentration in a rotary evaporator are carried out. The residue is purified by means of flash chromatography (5% ethyl acetate in toluene). In this way the title compound is obtained in the form of yellow crystals.

Example 1.6

5-(2,6-Difluorophenyl)-3-(4'-trifluoromethoxybiphenyl-4-yl)-[1,2,4]triazine

Analogously to the procedure indicated in Example 1.2, the title compound having a melting point of 159–160° C. is obtained by Pd-catalysed coupling of 150 mg of 3-(4-bromophenyl)-5-(2,6-difluorophenyl)-[1,2,4]triazine with 97 mg of 4-trifluoromethoxyphenyl-boric acid.

Example 1.7

6-(4-Chlorobenzylamino)-3-(2,6-difluorophenyl)-[1,2,4]triazine a) At room temperature, 30 g of N'-[(2,6-difluorophenyl)-imino-methyl]-hydrazinecarboxylic acid tert-butyl ester and 23.8 g of glyoxylic acid ethyl ester are stirred in 500 ml of toluene at 70° C. for 4 hours. The reaction mixture is then concentrated, 200 ml of formic acid are added and stirring is continued at room temperature for 5 hours. The reaction mixture is concentrated, and the residue is taken up in 300 ml of ethanol and boiled under reflux for 6 h. After concentration of the reaction mixture and recrystallisation from ethyl acetate there is obtained 3-(2,6-difluorophenyl)-[1,2,4]triazin-6(1H)-one having a melting point of 219–226° C.

b) 1 g of 3-(2,6-difluorophenyl)-[1,2,4]triazin-6(1H)-one is placed in 20 ml of dioxane and at room temperature 0.73 g of $POCl_3$ is added. Then, within a period of 5 min, 0.48 g of triethylamine in 3 ml of dioxane is added dropwise and stirring is carried out at room temperature for 30 min. The reaction mixture is then poured into ice-water and extracted with ethyl acetate, and the organic phase is separated off and concentrated. In this way 6-chloro-3-(2,6-difluorophenyl)-[1,2,4]triazine is obtained in the form of a yellow oil. The crude product is reacted further without purification.

c) 0.9 g of 6-chloro-3-(2,6-difluorophenyl)-[1,2,4]triazine is placed in 10 ml of methylene chloride, and 0.57 g of 4-chlorobenzylamine and 0.81 g of triethylamine are added. After being stirred at room temperature for 2 h, the reaction mixture is poured into water and extracted with methylene chloride; the organic phase is concentrated and the residue is purified by means of column chromatography over silica gel. In this way the title compound having a melting point of 200–205° C. is obtained.

Example 1.8

6-(3-Chlorophenoxy)-3-(2,6-difluorophenyl)-[1,2,4]triazine 325 mg of 6-chloro-3-(2,6-difluorophenyl)-[1,2,4]triazine (see Example 1.7 b) are placed in 10 ml of acetonitrile; 230 mg of 3-chlorophenol and 190 mg of potassium carbonate are added and stirring is carried out at room temperature for 2 h. The reaction mixture is then poured into water and extracted with ethyl acetate; the ethyl acetate phase is concentrated and the crude product is purified by means of flash chromatography. In this way the title compound having a melting point of 132–137° C. is obtained.

Example 1.9

6-[2-(4-Chlorophenyl)-vinyl]-3-(2,6-difluorophenyl)-[1,2,4]triazine a) 1.89 g of methylglyoxal (40% in water) are added to 2.71 g of N'-[(2,6-difluorophenyl)-iminomethyl]- hydrazinecarboxylic acid tert-butyl ester in 30 ml of ethanol and stirring is carried out at room temperature for 16 h. The reaction mixture is then concentrated, and the residue is taken up in 20 ml of formic acid and stirring is continued at room temperature for 5 h. The reaction mixture is concentrated by evaporation; the residue is again dissolved in 20 ml of ethanol, boiled under reflux for 2 h, then concentrated and purified by means of column chromatography. In this way 3-(2,6-difluorophenyl)-6-methyl-[1,2,4]triazine having a melting point of 90–93° C. is obtained.

b) At −20° C., 1.5 ml of n-butyllithium (1.6M in hexane) are added to 202 mg of diisopropylamine in 6 ml of tetrahydrofuran. After 15 min. the reaction mixture is cooled to −50° C. and 0.414 g of 3-(2,6-difluorophenyl)-6-methyl-[1,2,4]triazine in 2 ml of tetrahydrofuran is added dropwise. After 20 min. the mixture is cooled to −70° C., 0.281 g of 4-chlorobenzaldehyde in 3 ml of tetrahydrofuran is added dropwise and the mixture is then stirred at −70° C. for 2 h. The reaction mixture is then poured into ice-water and extracted with ethyl acetate; the organic phase is concentrated and the residue is purified by means of flash chromatography. In this way 1-(4-chlorophenyl)-2-[3-(2,6-difluorophenyl)-[1,2,4]triazin-6-yl]-ethanol is obtained in the form of a light-brown resin. After recrystallisation from diethyl ether/hexane, 1-(4-chlorophenyl)-2-[3-(2,6-difluorophenyl)-[1,2,4]triazin-6-yl]-ethanol is obtained in the form of beige crystals having a melting point of 98–102° C.

c) 140 mg of 1-(4-chlorophenyl)-2-[3-(2,6-difluorophenyl)-[1,2,4]triazin-6-yl]-ethanol and 10 mg of p-toluenesulfonic acid in 10 ml of toluene are boiled under reflux using a water separator for 2 h; the reaction mixture is then poured into water, and the toluene phase is separated off, dried with sodium sulfate and concentrated by evaporation. After recrystallisation of the residue from cyclohexane, the title compound having a melting point of 135–140° C. is obtained.

Analogously to the procedures described above it is also possible to prepare the substances mentioned in the following Tables 1 to 6. The numerical values relate to the melting points and are given in °C.

TABLE 1

Compounds of the formula

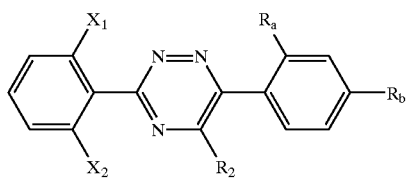

| No. | $X_1$ | $X_2$ | $R_2$ | $R_a$ | $R_b$ | Phys. data |
|---|---|---|---|---|---|---|
| 1.1 | F | F | H | $CH_3$ | 4-F—Ph | |
| 1.2 | F | F | H | $CH_3$ | 4-Cl—Ph | |
| 1.3 | F | F | H | $CH_3$ | 3-$CF_3$—Ph | |
| 1.4 | F | F | H | $CH_3$ | 4-$CF_3$—Ph | |
| 1.5 | F | F | H | $CH_3$ | 4-$OCF_3$—Ph | |
| 1.6 | F | F | H | $CH_3$ | 4-tert-butyl-Ph | |
| 1.7 | F | F | H | $CH_3$ | 2,4-$Cl_2$—Ph | |
| 1.8 | F | F | H | $CH_3$ | 3,5-$Cl_2$—Ph | |
| 1.9 | F | F | H | $CH_3$ | 2-$CF_3$—Ph | |
| 1.10 | F | F | H | $CH_3$ | 4-$OCH_3$—Ph | |
| 1.11 | F | F | H | $CH_3$ | 4-$SCH_3$—Ph | |
| 1.12 | F | F | H | $CH_3$ | 3-$OCH_3$—Ph | |
| 1.13 | F | F | H | $CH_3$ | 3-Cl—Ph | |
| 1.14 | F | F | H | $CH_3$ | 3,4-$Cl_2$—Ph | |
| 1.15 | F | F | H | $CH_3$ | 3-Cl-4-F—Ph | |
| 1.16 | F | F | H | $CH_3$ | 4-Br | 163–165 |
| 1.17 | F | F | H | $OCH_3$ | 4-F—Ph | |
| 1.18 | F | F | H | $OCH_3$ | 4-Cl—Ph | 172–173 |
| 1.19 | F | F | H | $OCH_3$ | 3-$CF_3$—Ph | |
| 1.20 | F | F | H | $OCH_3$ | 4-$CF_3$—Ph | 178–179 |
| 1.21 | F | F | H | $OCH_3$ | 4-$OCF_3$—Ph | 162–163 |
| 1.22 | F | F | H | $OCH_2CH_3$ | 4-tert-butyl-Ph | 135–137 |
| 1.23 | F | F | H | $OCH_3$ | 2,4-$Cl_2$—Ph | |
| 1.24 | F | F | H | $OCH_3$ | 3,5-$Cl_2$—Ph | |
| 1.25 | F | F | H | $OCH_3$ | 2-$CF_3$—Ph | |
| 1.26 | F | F | H | $OCH_3$ | 4-$OCH_3$—Ph | |
| 1.27 | F | F | H | $OCH_3$ | 4-$SCH_3$—Ph | |
| 1.28 | F | F | H | $OCH_3$ | 3-$OCH_3$—Ph | |
| 1.29 | F | F | H | $OCH_3$ | 3-Cl—Ph | |
| 1.30 | F | F | H | $OCH_3$ | 3,4-$Cl_2$—Ph | |
| 1.31 | F | F | H | $OCH_3$ | 3-Cl-4-F—Ph | 182–183 |
| 1.32 | F | F | H | $CF_3$ | 4-F—Ph | |
| 1.33 | F | F | H | $CF_3$ | 4-Cl—Ph | |
| 1.34 | F | F | H | $CF_3$ | 3-$CF_3$—Ph | |
| 1.35 | F | F | H | $CF_3$ | 4-$CF_3$—Ph | |
| 1.36 | F | F | H | $CF_3$ | 4-$OCF_3$—Ph | |
| 1.37 | F | F | H | $CF_3$ | 4-tert-butyl-Ph | |
| 1.38 | F | F | H | $CF_3$ | 2,4-$Cl_2$—Ph | |

TABLE 1-continued

Compounds of the formula

| No. | $X_1$ | $X_2$ | $R_2$ | $R_a$ | $R_b$ | Phys. data |
|---|---|---|---|---|---|---|
| 1.39 | F | F | H | CF$_3$ | 3,5-Cl$_2$—Ph | |
| 1.40 | F | F | H | CF$_3$ | 2-CF$_3$—Ph | |
| 1.41 | F | F | H | CF$_3$ | 4-OCH$_3$—Ph | |
| 1.42 | F | F | H | CF$_3$ | 4-SCH$_3$—Ph | |
| 1.43 | F | F | H | CF$_3$ | 3-OCH$_3$—Ph | |
| 1.44 | F | F | H | CF$_3$ | 3-Cl—Ph | |
| 1.45 | F | F | H | CF$_3$ | 3,4-Cl$_2$—Ph | |
| 1.46 | F | F | H | CF$_3$ | 3-Cl-4-F—Ph | |
| 1.47 | F | F | CH$_3$ | H | 4-F—Ph | |
| 1.48 | F | F | CH$_3$ | H | 4-Cl—Ph | |
| 1.49 | F | F | CH$_3$ | H | 3-CF$_3$—Ph | |
| 1.50 | F | F | CH$_3$ | H | 4-CF$_3$—Ph | 201–203 |
| 1.51 | F | F | CH$_3$ | H | 4-OCF$_3$—Ph | 168–189 |
| 1.52 | F | F | CH$_3$ | H | 4-tert-butyl-Ph | |
| 1.53 | F | F | CH$_3$ | H | 2,4-Cl$_2$—Ph | |
| 1.54 | F | F | CH$_3$ | H | 3,5-Cl$_2$—Ph | |
| 1.55 | F | F | CH$_3$ | H | 2-CF$_3$—Ph | |
| 1.56 | F | F | CH$_3$ | H | 4-OCH$_3$—Ph | |
| 1.57 | F | F | CH$_3$ | H | 4-SCH$_3$—Ph | |
| 1.58 | F | F | CH$_3$ | H | 3-OCH$_3$—Ph | |
| 1.59 | F | F | CH$_3$ | H | 3-Cl—Ph | |
| 1.60 | F | F | CH$_3$ | H | 3,4-Cl$_2$—Ph | |
| 1.61 | F | F | CH$_3$ | H | 3-Cl-4-F—Ph | |
| 1.62 | F | F | CH$_3$ | CH$_3$ | 4-F—Ph | |
| 1.63 | F | F | CH$_3$ | CH$_3$ | 4-Cl—Ph | |
| 1.64 | F | F | CH$_3$ | CH$_3$ | 3-CF$_3$—Ph | |
| 1.65 | F | F | CH$_3$ | CH$_3$ | 4-CF$_3$—Ph | |
| 1.66 | F | F | CH$_3$ | CH$_3$ | 4-OCF$_3$—Ph | |
| 1.67 | F | F | CH$_3$ | CH$_3$ | 4-tert-butyl-Ph | |
| 1.68 | F | F | CH$_3$ | CH$_3$ | 2,4-Cl$_2$—Ph | |
| 1.69 | F | F | CH$_3$ | CH$_3$ | 3,5-Cl$_2$—Ph | |
| 1.70 | F | F | CH$_3$ | CH$_3$ | 2-CF$_3$—Ph | |
| 1.71 | F | F | CH$_3$ | CH$_3$ | 4-OCH$_3$—Ph | |
| 1.72 | F | F | CH$_3$ | CH$_3$ | 4-SCH$_3$—Ph | |
| 1.73 | F | F | CH$_3$ | CH$_3$ | 3-OCH$_3$—Ph | |
| 1.74 | F | F | CH$_3$ | CH$_3$ | 3-Cl—Ph | |
| 1.75 | F | F | CH$_3$ | CH$_3$ | 3,4-Cl$_2$—Ph | |
| 1.76 | F | F | CH$_3$ | CH$_3$ | 3-Cl-4-F—Ph | |
| 1.77 | F | F | CH$_3$ | OCH$_3$ | 4-F—Ph | |
| 1.78 | F | F | CH$_3$ | OCH$_3$ | 4-Cl—Ph | |
| 1.79 | F | F | CH$_3$ | OCH$_3$ | 3-CF$_3$—Ph | |
| 1.80 | F | F | CH$_3$ | OCH$_3$ | 4-CF$_3$—Ph | |
| 1.81 | F | F | CH$_3$ | OCH$_3$ | 4-OCF$_3$—Ph | |
| 1.82 | F | F | CH$_3$ | OCH$_3$ | 4-tert-butyl-Ph | |
| 1.83 | F | F | CH$_3$ | OCH$_3$ | 2,4-Cl$_2$—Ph | |
| 1.84 | F | F | CH$_3$ | OCH$_3$ | 3,5-Cl$_2$—Ph | |
| 1.85 | F | F | CH$_3$ | OCH$_3$ | 2-CF$_3$—Ph | |
| 1.86 | F | F | CH$_3$ | OCH$_3$ | 4-OCH$_3$—Ph | |
| 1.87 | F | F | CH$_3$ | OCH$_3$ | 4-SCH$_3$—Ph | |
| 1.88 | F | F | CH$_3$ | OCH$_3$ | 3-OCH$_3$—Ph | |
| 1.89 | F | F | CH$_3$ | OCH$_3$ | 3-Cl—Ph | |
| 1.90 | F | F | CH$_3$ | OCH$_3$ | 3,4-Cl$_2$—Ph | |
| 1.91 | F | F | CH$_3$ | OCH$_3$ | 3-Cl-4-F—Ph | |
| 1.92 | F | F | CH$_3$ | CF$_3$ | 4-F—Ph | |
| 1.93 | F | F | CH$_3$ | CF$_3$ | 4-Cl—Ph | |
| 1.94 | F | F | CH$_3$ | CF$_3$ | 3-CF$_3$—Ph | |
| 1.95 | F | F | CH$_3$ | CF$_3$ | 4-CF$_3$—Ph | |
| 1.96 | F | F | CH$_3$ | CF$_3$ | 4-OCF$_3$—Ph | |
| 1.97 | F | F | CH$_3$ | CF$_3$ | 4-tert-butyl-Ph | |
| 1.98 | F | F | CH$_3$ | CF$_3$ | 2,4-Cl$_2$—Ph | |
| 1.99 | F | F | CH$_3$ | CF$_3$ | 3,5-Cl$_2$—Ph | |
| 1.100 | F | F | CH$_3$ | CF$_3$ | 2-CF$_3$—Ph | |
| 1.101 | F | F | CH$_3$ | CF$_3$ | 4-OCH$_3$—Ph | |
| 1.102 | F | F | CH$_3$ | CF$_3$ | 4-SCH$_3$—Ph | |
| 1.103 | F | F | CH$_3$ | CF$_3$ | 3-OCH$_3$—Ph | |

TABLE 1-continued

Compounds of the formula

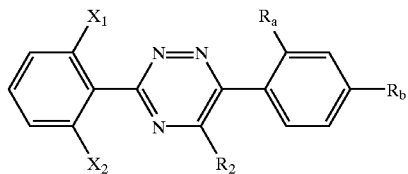

| No. | $X_1$ | $X_2$ | $R_2$ | $R_a$ | $R_b$ | Phys. data |
|---|---|---|---|---|---|---|
| 1.104 | F | F | CH$_3$ | CF$_3$ | 3-Cl—Ph | |
| 1.105 | F | F | CH$_3$ | CF$_3$ | 3,4-Cl$_2$—Ph | |
| 1.106 | F | F | CH$_3$ | CF$_3$ | 3-Cl-4-F—Ph | |
| 1.107 | F | Cl | H | H | 4-F—Ph | |
| 1.108 | F | Cl | H | H | 4-Cl—Ph | |
| 1.109 | F | Cl | H | H | 3-CF$_3$—Ph | |
| 1.110 | F | Cl | H | H | 4-CF$_3$—Ph | |
| 1.111 | F | Cl | H | H | 4-OCF$_3$—Ph | |
| 1.112 | F | Cl | H | H | 4-tert-butyl-Ph | |
| 1.113 | F | Cl | H | H | 2,4-Cl$_2$—Ph | |
| 1.114 | F | Cl | H | H | 3,5-Cl$_2$—Ph | |
| 1.115 | F | Cl | H | H | 2-CF$_3$—Ph | |
| 1.116 | F | Cl | H | H | 4-OCH$_3$—Ph | |
| 1.117 | F | Cl | H | H | 4-SCH$_3$—Ph | |
| 1.118 | F | Cl | H | H | 3-OCH$_3$—Ph | |
| 1.119 | F | Cl | H | H | 3-Cl—Ph | |
| 1.120 | F | Cl | H | H | 3,4-Cl$_2$—Ph | |
| 1.121 | F | Cl | H | H | 3-Cl-4-F—Ph | |
| 1.122 | F | Cl | H | CH$_3$ | 4-F—Ph | |
| 1.123 | F | Cl | H | CH$_3$ | 4-Cl—Ph | |
| 1.124 | F | Cl | H | CH$_3$ | 3-CF$_3$—Ph | |
| 1.125 | F | Cl | H | CH$_3$ | 4-CF$_3$—Ph | |
| 1.126 | F | Cl | H | CH$_3$ | 4-OCF$_3$—Ph | |
| 1.127 | F | Cl | H | CH$_3$ | 4-tert-butyl-Ph | |
| 1.128 | F | Cl | H | CH$_3$ | 2,4-Cl$_2$—Ph | |
| 1.129 | F | Cl | H | CH$_3$ | 3,5-Cl$_2$—Ph | |
| 1.130 | F | Cl | H | CH$_3$ | 2-CF$_3$—Ph | |
| 1.131 | F | Cl | H | CH$_3$ | 4-OCH$_3$—Ph | |
| 1.132 | F | Cl | H | CH$_3$ | 4-SCH$_3$—Ph | |
| 1.133 | F | Cl | H | CH$_3$ | 3-OCH$_3$—Ph | |
| 1.134 | F | Cl | H | CH$_3$ | 3-Cl—Ph | |
| 1.135 | F | Cl | H | CH$_3$ | 3,4-Cl$_2$—Ph | |
| 1.136 | F | Cl | H | CH$_3$ | 3-Cl-4-F—Ph | |
| 1.137 | F | Cl | H | OCH$_3$ | 4-F—Ph | |
| 1.138 | F | Cl | H | OCH$_3$ | 4-Cl—Ph | |
| 1.139 | F | Cl | H | OCH$_3$ | 3-CF$_3$—Ph | |
| 1.140 | F | Cl | H | OCH$_3$ | 4-CF$_3$—Ph | |
| 1.141 | F | Cl | H | OCH$_3$ | 4-OCF$_3$—Ph | |
| 1.142 | F | Cl | H | OCH$_3$ | 4-tert-butyl-Ph | |
| 1.143 | F | Cl | H | OCH$_3$ | 2,4-Cl$_2$—Ph | |
| 1.144 | F | Cl | H | OCH$_3$ | 3,5-Cl$_2$—Ph | |
| 1.145 | F | Cl | H | OCH$_3$ | 2-CF$_3$—Ph | |
| 1.146 | F | Cl | H | OCH$_3$ | 4-OCH$_3$—Ph | |
| 1.147 | F | Cl | H | OCH$_3$ | 4-SCH$_3$—Ph | |
| 1.148 | F | Cl | H | OCH$_3$ | 3-OCH$_3$—Ph | |
| 1.149 | F | Cl | H | OCH$_3$ | 3-Cl—Ph | |
| 1.150 | F | Cl | H | OCH$_3$ | 3,4-Cl$_2$—Ph | |
| 1.151 | F | Cl | H | OCH$_3$ | 3-Cl-4-F—Ph | |
| 1.152 | F | Cl | H | CF$_3$ | 4-F—Ph | |
| 1.153 | F | Cl | H | CF$_3$ | 4-Cl—Ph | |
| 1.154 | F | Cl | H | CF$_3$ | 3-CF$_3$—Ph | |
| 1.155 | F | Cl | H | CF$_3$ | 4-CF$_3$—Ph | |
| 1.156 | F | Cl | H | CF$_3$ | 4-OCF$_3$—Ph | |
| 1.157 | F | Cl | H | CF$_3$ | 4-tert-butyl-Ph | |
| 1.158 | F | Cl | H | CF$_3$ | 2,4-Cl$_2$—Ph | |
| 1.159 | F | Cl | H | CF$_3$ | 3,5-Cl$_2$—Ph | |
| 1.160 | F | Cl | H | CF$_3$ | 2-CF$_3$—Ph | |
| 1.161 | F | Cl | H | CF$_3$ | 4-OCH$_3$—Ph | |
| 1.162 | F | Cl | H | CF$_3$ | 4-SCH$_3$—Ph | |
| 1.163 | F | Cl | H | CF$_3$ | 3-OCH$_3$—Ph | |
| 1.164 | F | Cl | H | CF$_3$ | 3-Cl—Ph | |
| 1.165 | F | Cl | H | CF$_3$ | 3,4-Cl$_2$—Ph | |
| 1.166 | F | Cl | H | CF$_3$ | 3-Cl-4-F—Ph | |
| 1.167 | F | Cl | CH$_3$ | H | 4-F—Ph | |
| 1.168 | F | Cl | CH$_3$ | H | 4-Cl—Ph | |

TABLE 1-continued

Compounds of the formula

| No. | $X_1$ | $X_2$ | $R_2$ | $R_a$ | $R_b$ | Phys. data |
|---|---|---|---|---|---|---|
| 1.169 | F | Cl | $CH_3$ | H | 3-$CF_3$—Ph | |
| 1.170 | F | Cl | $CH_3$ | H | 4-$CF_3$—Ph | |
| 1.171 | F | Cl | $CH_3$ | H | 4-$OCF_3$—Ph | |
| 1.172 | F | Cl | $CH_3$ | H | 4-tert-butyl-Ph | |
| 1.173 | F | Cl | $CH_3$ | H | 2,4-$Cl_2$—Ph | |
| 1.174 | F | Cl | $CH_3$ | H | 3,5-$Cl_2$—Ph | |
| 1.175 | F | Cl | $CH_3$ | H | 2-$CF_3$—Ph | |
| 1.176 | F | Cl | $CH_3$ | H | 4-$OCH_3$—Ph | |
| 1.177 | F | Cl | $CH_3$ | H | 4-$SCH_3$—Ph | |
| 1.178 | F | Cl | $CH_3$ | H | 3-$OCH_3$—Ph | |
| 1.179 | F | Cl | $CH_3$ | H | 3-Cl—Ph | |
| 1.180 | F | Cl | $CH_3$ | H | 3,4-$Cl_2$—Ph | |
| 1.181 | F | Cl | $CH_3$ | H | 3-Cl-4-F—Ph | |
| 1.182 | F | Cl | $CH_3$ | $CH_3$ | 4-F—Ph | |
| 1.183 | F | Cl | $CH_3$ | $CH_3$ | 4-Cl—Ph | |
| 1.184 | F | Cl | $CH_3$ | $CH_3$ | 3-$CF_3$—Ph | |
| 1.185 | F | Cl | $CH_3$ | $CH_3$ | 4-$CF_3$—Ph | |
| 1.186 | F | Cl | $CH_3$ | $CH_3$ | 4-$OCF_3$—Ph | |
| 1.187 | F | Cl | $CH_3$ | $CH_3$ | 4-tert-butyl-Ph | |
| 1.188 | F | Cl | $CH_3$ | $CH_3$ | 2,4-$Cl_2$—Ph | |
| 1.189 | F | Cl | $CH_3$ | $CH_3$ | 3,5-$Cl_2$—Ph | |
| 1.190 | F | Cl | $CH_3$ | $CH_3$ | 2-$CF_3$—Ph | |
| 1.191 | F | Cl | $CH_3$ | $CH_3$ | 4-$OCH_3$—Ph | |
| 1.192 | F | Cl | $CH_3$ | $CH_3$ | 4-$SCH_3$—Ph | |
| 1.193 | F | Cl | $CH_3$ | $CH_3$ | 3-$OCH_3$—Ph | |
| 1.194 | F | Cl | $CH_3$ | $CH_3$ | 3-Cl—Ph | |
| 1.195 | F | Cl | $CH_3$ | $CH_3$ | 3,4-$Cl_2$—Ph | |
| 1.196 | F | Cl | $CH_3$ | $CH_3$ | 3-Cl-4-F—Ph | |
| 1.197 | F | Cl | $CH_3$ | $OCH_3$ | 4-F—Ph | |
| 1.198 | F | Cl | $CH_3$ | $OCH_3$ | 4-Cl—Ph | |
| 1.199 | F | Cl | $CH_3$ | $OCH_3$ | 3-$CF_3$—Ph | |
| 1.200 | F | Cl | $CH_3$ | $OCH_3$ | 4-$CF_3$—Ph | |
| 1.201 | F | Cl | $CH_3$ | $OCH_3$ | 4-$OCF_3$—Ph | |
| 1.202 | F | Cl | $CH_3$ | $OCH_3$ | 4-tert-butyl-Ph | |
| 1.203 | F | Cl | $CH_3$ | $OCH_3$ | 2,4-$Cl_2$—Ph | |
| 1.204 | F | Cl | $CH_3$ | $OCH_3$ | 3,5-$Cl_2$—Ph | |
| 1.205 | F | Cl | $CH_3$ | $OCH_3$ | 2-$CF_3$—Ph | |
| 1.206 | F | Cl | $CH_3$ | $OCH_3$ | 4-$OCH_3$—Ph | |
| 1.207 | F | Cl | $CH_3$ | $OCH_3$ | 4-$SCH_3$—Ph | |
| 1.208 | F | Cl | $CH_3$ | $OCH_3$ | 3-$OCH_3$—Ph | |
| 1.209 | F | Cl | $CH_3$ | $OCH_3$ | 3-Cl—Ph | |
| 1.210 | F | Cl | $CH_3$ | $OCH_3$ | 3,4-$Cl_2$—Ph | |
| 1.211 | F | Cl | $CH_3$ | $OCH_3$ | 3-Cl-4-F—Ph | |
| 1.212 | F | Cl | $CH_3$ | $CF_3$ | 4-F—Ph | |
| 1.213 | F | Cl | $CH_3$ | $CF_3$ | 4-Cl—Ph | |
| 1.214 | F | Cl | $CH_3$ | $CF_3$ | 3-$CF_3$—Ph | |
| 1.215 | F | Cl | $CH_3$ | $CF_3$ | 4-$CF_3$—Ph | |
| 1.216 | F | Cl | $CH_3$ | $CF_3$ | 4-$OCF_3$—Ph | |
| 1.217 | F | Cl | $CH_3$ | $CF_3$ | 4-tert-butyl-Ph | |
| 1.218 | F | Cl | $CH_3$ | $CF_3$ | 2,4-$Cl_2$—Ph | |
| 1.219 | F | Cl | $CH_3$ | $CF_3$ | 3,5-$Cl_2$—Ph | |
| 1.220 | F | Cl | $CH_3$ | $CF_3$ | 2-$CF_3$—Ph | |
| 1.221 | F | Cl | $CH_3$ | $CF_3$ | 4-$OCH_3$—Ph | |
| 1.222 | F | Cl | $CH_3$ | $CF_3$ | 4-$SCH_3$—Ph | |
| 1.223 | F | Cl | $CH_3$ | $CF_3$ | 3-$OCH_3$—Ph | |
| 1.224 | F | Cl | $CH_3$ | $CF_3$ | 3-Cl—Ph | |
| 1.225 | F | Cl | $CH_3$ | $CF_3$ | 3,4-$Cl_2$—Ph | |
| 1.226 | F | Cl | $CH_3$ | $CF_3$ | 3-Cl-4-F—Ph | |
| 1.227 | Cl | Cl | H | H | 4-F—Ph | |
| 1.228 | Cl | Cl | H | H | 4-Cl—Ph | |
| 1.229 | Cl | Cl | H | H | 3-$CF_3$—Ph | |
| 1.230 | Cl | Cl | H | H | 4-$CF_3$—Ph | |
| 1.231 | Cl | Cl | H | H | 4-$OCF_3$—Ph | |
| 1.232 | Cl | Cl | H | H | 4-tert-butyl-Ph | |
| 1.233 | Cl | Cl | H | H | 2,4-$Cl_2$—Ph | |

TABLE 1-continued

Compounds of the formula

| No. | $X_1$ | $X_2$ | $R_2$ | $R_a$ | $R_b$ | Phys. data |
|---|---|---|---|---|---|---|
| 1.234 | Cl | Cl | H | H | 3,5-$Cl_2$—Ph | |
| 1.235 | Cl | Cl | H | H | 2-$CF_3$—Ph | |
| 1.236 | Cl | Cl | H | H | 4-$OCH_3$—Ph | |
| 1.237 | Cl | Cl | H | H | 4-$SCH_3$—Ph | |
| 1.238 | Cl | Cl | H | H | 3-$OCH_3$—Ph | |
| 1.239 | Cl | Cl | H | H | 3-Cl—Ph | |
| 1.240 | Cl | Cl | H | H | 3,4-$Cl_2$—Ph | |
| 1.241 | Cl | Cl | H | H | 3-Cl-4-F—Ph | |
| 1.242 | Cl | Cl | H | $CH_3$ | 4-F—Ph | |
| 1.243 | Cl | Cl | H | $CH_3$ | 4-Cl—Ph | |
| 1.244 | Cl | Cl | H | $CH_3$ | 3-$CF_3$—Ph | |
| 1.245 | Cl | Cl | H | $CH_3$ | 4-$CF_3$—Ph | |
| 1.246 | Cl | Cl | H | $CH_3$ | 4-$OCF_3$—Ph | |
| 1.247 | Cl | Cl | H | $CH_3$ | 4-tert-butyl-Ph | |
| 1.248 | Cl | Cl | H | $CH_3$ | 2,4-$Cl_2$—Ph | |
| 1.249 | Cl | Cl | H | $CH_3$ | 3,5-$Cl_2$—Ph | |
| 1.250 | Cl | Cl | H | $CH_3$ | 2-$CF_3$—Ph | |
| 1.251 | Cl | Cl | H | $CH_3$ | 4-$OCH_3$—Ph | |
| 1.252 | Cl | Cl | H | $CH_3$ | 4-$SCH_3$—Ph | |
| 1.253 | Cl | Cl | H | $CH_3$ | 3-$OCH_3$—Ph | |
| 1.254 | Cl | Cl | H | $CH_3$ | 3-Cl—Ph | |
| 1.255 | Cl | Cl | H | $CH_3$ | 3,4-$Cl_2$—Ph | |
| 1.256 | Cl | Cl | H | $CH_3$ | 3-Cl-4-F—Ph | |
| 1.257 | Cl | Cl | H | $OCH_3$ | 4-F—Ph | |
| 1.258 | Cl | Cl | H | $OCH_3$ | 4-Cl—Ph | |
| 1.259 | Cl | Cl | H | $OCH_3$ | 3-$CF_3$—Ph | |
| 1.260 | Cl | Cl | H | $OCH_3$ | 4-$CF_3$—Ph | |
| 1.261 | Cl | Cl | H | $OCH_3$ | 4-$OCF_3$—Ph | |
| 1.262 | Cl | Cl | H | $OCH_3$ | 4-tert-butyl-Ph | |
| 1.263 | Cl | Cl | H | $OCH_3$ | 2,4-$Cl_2$—Ph | |
| 1.264 | Cl | Cl | H | $OCH_3$ | 3,5-$Cl_2$—Ph | |
| 1.265 | Cl | Cl | H | $OCH_3$ | 2-$CF_3$—Ph | |
| 1.266 | Cl | Cl | H | $OCH_3$ | 4-$OCH_3$—Ph | |
| 1.267 | Cl | Cl | H | $OCH_3$ | 4-$SCH_3$—Ph | |
| 1.268 | Cl | Cl | H | $OCH_3$ | 3-$OCH_3$—Ph | |
| 1.269 | Cl | Cl | H | $OCH_3$ | 3-Cl—Ph | |
| 1.270 | Cl | Cl | H | $OCH_3$ | 3,4-$Cl_2$—Ph | |
| 1.271 | Cl | Cl | H | $OCH_3$ | 3-Cl-4-F—Ph | |
| 1.272 | Cl | Cl | H | $CF_3$ | 4-F—Ph | |
| 1.273 | Cl | Cl | H | $CF_3$ | 4-Cl—Ph | |
| 1.274 | Cl | Cl | H | $CF_3$ | 3-$CF_3$—Ph | |
| 1.275 | Cl | Cl | H | $CF_3$ | 4-$CF_3$—Ph | |
| 1.276 | Cl | Cl | H | $CF_3$ | 4-$OCF_3$—Ph | |
| 1.277 | Cl | Cl | H | $CF_3$ | 4-tert-butyl-Ph | |
| 1.278 | Cl | Cl | H | $CF_3$ | 2,4-$Cl_2$—Ph | |
| 1.279 | Cl | Cl | H | $CF_3$ | 3,5-$Cl_2$—Ph | |
| 1.280 | Cl | Cl | H | $CF_3$ | 2-$CF_3$—Ph | |
| 1.281 | Cl | Cl | H | $CF_3$ | 4-$OCH_3$—Ph | |
| 1.282 | Cl | Cl | H | $CF_3$ | 4-$SCH_3$—Ph | |
| 1.283 | Cl | Cl | H | $CF_3$ | 3-$OCH_3$—Ph | |
| 1.284 | Cl | Cl | H | $CF_3$ | 3-Cl—Ph | |
| 1.285 | Cl | Cl | H | $CF_3$ | 3,4-$Cl_2$—Ph | |
| 1.286 | Cl | Cl | H | $CF_3$ | 3-Cl-4-F—Ph | |
| 1.287 | Cl | Cl | $CH_3$ | H | 4-F—Ph | |
| 1.288 | Cl | Cl | $CH_3$ | H | 4-Cl—Ph | |
| 1.289 | Cl | Cl | $CH_3$ | H | 3-$CF_3$—Ph | |
| 1.290 | Cl | Cl | $CH_3$ | H | 4-$CF_3$—Ph | |
| 1.291 | Cl | Cl | $CH_3$ | H | 4-$OCF_3$—Ph | |
| 1.292 | Cl | Cl | $CH_3$ | H | 4-tert-butyl-Ph | |
| 1.293 | Cl | Cl | $CH_3$ | H | 2,4-$Cl_2$—Ph | |
| 1.294 | Cl | Cl | $CH_3$ | H | 3,5-$Cl_2$—Ph | |
| 1.295 | Cl | Cl | $CH_3$ | H | 2-$CF_3$—Ph | |
| 1.296 | Cl | Cl | $CH_3$ | H | 4-$OCH_3$—Ph | |
| 1.297 | Cl | Cl | $CH_3$ | H | 4-$SCH_3$—Ph | |
| 1.298 | Cl | Cl | $CH_3$ | H | 3-$OCH_3$—Ph | |

TABLE 1-continued

Compounds of the formula

| No. | X₁ | X₂ | R₂ | Rₐ | R_b | Phys. data |
|---|---|---|---|---|---|---|
| 1.299 | Cl | Cl | CH₃ | H | 3-Cl—Ph | |
| 1.300 | Cl | Cl | CH₃ | H | 3,4-Cl₂—Ph | |
| 1.301 | Cl | Cl | CH₃ | H | 3-Cl-4-F—Ph | |
| 1.302 | Cl | Cl | CH₃ | CH₃ | 4-F—Ph | |
| 1.303 | Cl | Cl | CH₃ | CH₃ | 4-Cl—Ph | |
| 1.304 | Cl | Cl | CH₃ | CH₃ | 3-CF₃—Ph | |
| 1.305 | Cl | Cl | CH₃ | CH₃ | 4-CF₃—Ph | |
| 1.306 | Cl | Cl | CH₃ | CH₃ | 4-OCF₃—Ph | |
| 1.307 | Cl | Cl | CH₃ | CH₃ | 4-tert-butyl-Ph | |
| 1.308 | Cl | Cl | CH₃ | CH₃ | 2,4-Cl₂—Ph | |
| 1.309 | Cl | Cl | CH₃ | CH₃ | 3,5-Cl₂—Ph | |
| 1.310 | Cl | Cl | CH₃ | CH₃ | 2-CF₃—Ph | |
| 1.311 | Cl | Cl | CH₃ | CH₃ | 4-OCH₃—Ph | |
| 1.312 | Cl | Cl | CH₃ | CH₃ | 4-SCH₃—Ph | |
| 1.313 | Cl | Cl | CH₃ | CH₃ | 3-OCH₃—Ph | |
| 1.314 | Cl | Cl | CH₃ | CH₃ | 3-Cl—Ph | |
| 1.315 | Cl | Cl | CH₃ | CH₃ | 3,4-Cl₂—Ph | |
| 1.316 | Cl | Cl | CH₃ | CH₃ | 3-Cl-4-F—Ph | |
| 1.317 | Cl | Cl | CH₃ | OCH₃ | 4-F—Ph | |
| 1.318 | Cl | Cl | CH₃ | OCH₃ | 4-Cl—Ph | |
| 1.319 | Cl | Cl | CH₃ | OCH₃ | 3-CF₃—Ph | |
| 1.320 | Cl | Cl | CH₃ | OCH₃ | 4-CF₃—Ph | |
| 1.321 | Cl | Cl | CH₃ | OCH₃ | 4-OCF₃—Ph | |
| 1.322 | Cl | Cl | CH₃ | OCH₃ | 4-tert-butyl-Ph | |
| 1.323 | Cl | Cl | CH₃ | OCH₃ | 2,4-Cl₂—Ph | |
| 1.324 | Cl | Cl | CH₃ | OCH₃ | 3,5-Cl₂—Ph | |
| 1.325 | Cl | Cl | CH₃ | OCH₃ | 2-CF₃—Ph | |
| 1.326 | Cl | Cl | CH₃ | OCH₃ | 4-OCH₃—Ph | |
| 1.327 | Cl | Cl | CH₃ | OCH₃ | 4-SCH₃—Ph | |
| 1.328 | Cl | Cl | CH₃ | OCH₃ | 3-OCH₃—Ph | |
| 1.329 | Cl | Cl | CH₃ | OCH₃ | 3-Cl—Ph | |
| 1.330 | Cl | Cl | CH₃ | OCH₃ | 3,4-Cl₂—Ph | |
| 1.331 | Cl | Cl | CH₃ | OCH₃ | 3-Cl-4-F—Ph | |
| 1.332 | Cl | Cl | CH₃ | CF₃ | 4-F—Ph | |
| 1.333 | Cl | Cl | CH₃ | CF₃ | 4-Cl—Ph | |
| 1.334 | Cl | Cl | CH₃ | CF₃ | 3-CF₃—Ph | |
| 1.335 | Cl | Cl | CH₃ | CF₃ | 4-CF₃—Ph | |
| 1.336 | Cl | Cl | CH₃ | CF₃ | 4-OCF₃—Ph | |
| 1.337 | Cl | Cl | CH₃ | CF₃ | 4-tert-butyl-Ph | |
| 1.338 | Cl | Cl | CH₃ | CF₃ | 2,4-Cl₂—Ph | |
| 1.339 | Cl | Cl | CH₃ | CF₃ | 3,5-Cl₂—Ph | |
| 1.340 | Cl | Cl | CH₃ | CF₃ | 2-CF₃—Ph | |
| 1.341 | Cl | Cl | CH₃ | CF₃ | 4-OCH₃—Ph | |
| 1.342 | Cl | Cl | CH₃ | CF₃ | 4-SCH₃—Ph | |
| 1.343 | Cl | Cl | CH₃ | CF₃ | 3-OCH₃—Ph | |
| 1.344 | Cl | Cl | CH₃ | CF₃ | 3-Cl—Ph | |
| 1.345 | Cl | Cl | CH₃ | CF₃ | 3,4-Cl₂—Ph | |
| 1.346 | Cl | Cl | CH₃ | CF₃ | 3-Cl-4-F—Ph | |
| 1.347 | F | F | H | H | 4-SCH₃—Ph | |
| 1.348 | Cl | H | F | H | 4-CF₃—Ph | |
| 1.349 | Cl | H | F | H | 4-OCF₃—Ph | |
| 1.350 | Cl | H | F | H | 3,5-Cl₂—Ph | |
| 1.351 | F | F | H | H | 3,4(OCH₃)₂—Ph | 207–209 |
| 1.352 | F | F | CH₃ | H | 4-Br | 182–185 |
| 1.353 | F | F | H | H | 4-OH—Ph | 224–227 |
| 1.354 | F | F | H | H | 4-CN—Ph | 146–147 |
| 1.355 | F | F | H | H | 3-CN—Ph | solid |
| 1.356 | H | H | H | H | 4-Br | 210–212 |
| 1.357 | F | F | H | H | 4-OCH₃ | 152–153 |
| 1.358 | F | F | H | H | furan-2-yl | 183–184 |
| 1.359 | F | F | H | H | —CH=CH—C(=O)OCH₃ | 222–224 |
| 1.360 | F | F | H | H | —CH=CH—C₆H₅ | 220–221 |
| 1.361 | F | F | H | H | —CH=CH—C₆H₄-Br | 199–201 |
| 1.362 | F | F | H | H | cyclohex-1-en-3-on-1-yl | 231–232 |
| 1.363 | F | F | H | H | —CH=CH—C(=O)NH₂ | >250 |

TABLE 1-continued

Compounds of the formula

| No. | X₁ | X₂ | R₂ | Rₐ | R_b | Phys. data |
|---|---|---|---|---|---|---|
| 1.364 | F | F | H | H | —CH=C(CH₃)—C(=O)OCH₃ | 151–155 |
| 1.365 | F | F | H | H | cyclohex-1-en-1-yl | 139–141 |
| 1.366 | F | F | H | H | —CH=CH—SO₂CH₃ | 231–232 |
| 1.367 | F | F | H | H | —C[COOCH₃]=CH—COOCH₃ | 169–175 |
| 1.368 | F | F | H | H | —CH=CH—CH₂—O—C₆H₅ | 152–156 |
| 1.369 | F | F | H | H | —C₆H₄-4-CHO | 230–233 |
| 1.370 | F | F | H | H | —C₆H₄-3-CHO | 201–203 |
| 1.371 | F | F | H | H | —C(CH₃)=CH—C(=O)OCH₃ | 185–187 |
| 1.372 | F | F | H | H | —C₆H₄-4-CH=NOH | solid |
| 1.373 | F | F | H | H | —C₆H₄-4-CH=NOC(=O)CH₃ | 188–190 |
| 1.374 | F | F | H | H | —C₆H₄-3-CH=NOH | solid |
| 1.375 | F | F | H | H | —C₆H₄-4-C(=O)CH₃ | 231–233 |
| 1.376 | F | F | H | H | —C₆H₄-3-C(=O)CH₃ | 200–203 |
| 1.377 | F | F | H | H | —CH=CH—CN | >250 |
| 1.378 | F | F | H | H | —C₆H₄-4-C(CH₃)=NOCH₃ | 198–201 |
| 1.379 | F | F | H | H | —C₆H₄-3-C(CH₃)=NOCH₃ | 162–164 |
| 1.380 | F | F | H | H | —C≡C—C₆H₄-2-F | 191–192 |
| 1.381 | F | F | H | H | —C≡C—C(CH₃)₂OH | 179–180 |
| 1.382 | F | F | H | H | —P(=O)(OC₂H₅)₂ | 114–115 |
| 1.383 | F | F | H | H | H | 100–104 |
| 1.384 | F | F | H | CH₂SCH₃ | 4-CF₃—Ph | |
| 1.385 | F | F | H | CH₂SCH₃ | 4-OCF₃—Ph | |
| 1.386 | F | F | H | CH₂CH₃ | 4-CF₃—Ph | |
| 1.387 | F | F | H | CH₂CH₃ | 4-OCF₃—Ph | |
| 1.388 | F | F | i-Prop | H | 4-CF₃—Ph | 165–170 |
| 1.389 | F | F | H | H | —C≡C—C₆H₄-4-CH₃ | 188–190 |
| 1.390 | F | F | H | H | —C≡C—C₆H₄-4-Cl | 199–202 |
| 1.391 | F | F | CH₂Br | H | Br | |
| 1.392 | F | F | CHBr₂ | H | Br | |
| 1.393 | F | F | H | H | Cyclohexyl | 138–140 |
| 1.394 | F | H | H | H | 4-CH₃—Ph | 249–250 |
| 1.395 | F | F | H | —O—C₂H₅ | t-Butyl | 135–137 |
| 1.396 | F | H | H | H | Br | 173 |
| 1.397 | F | F | H | H | 4-SCF₃—Ph | |
| 1.398 | F | F | H | H | 4-SOCF₃—Ph | |
| 1.399 | F | F | H | H | 4-SO₂CF₃—Ph | |
| 1.400 | F | Cl | H | H | 4-SCF₃—Ph | |
| 1.401 | F | Cl | H | H | 4-SOCF₃—Ph | |
| 1.402 | F | Cl | H | H | 4-SO₂CF₃—Ph | |
| 1.403 | F | F | CH₃ | H | 4-SCF₃—Ph | |
| 1.404 | F | F | CH₃ | H | 4-SOCF₃—Ph | |
| 1.405 | F | F | CH₃ | H | 4-SO₂CF₃—Ph | |
| 1.406 | F | H | H | H | 4-F—Ph | |
| 1.407 | F | H | H | H | 4-Cl—Ph | 277–278 |
| 1.408 | F | H | H | H | 3-CF₃—Ph | 189–190 |
| 1.409 | F | H | H | H | 4-CF₃—Ph | 294–295 |
| 1.410 | F | H | H | H | 4-OCF₃—Ph | 302–303 |
| 1.411 | F | H | H | H | 4-t-Butyl-Ph | 206–207 |
| 1.412 | F | H | H | H | 2,4-Cl₂—Ph | 229–230 |
| 1.413 | F | H | H | H | 3,5-Cl₂—Ph | 203–204 |
| 1.414 | F | H | H | H | 2-CF₃—Ph | |
| 1.415 | F | H | H | H | 4-OCH₃—Ph | |
| 1.416 | F | H | H | H | 4-SCH₃—Ph | 262–263 |
| 1.417 | F | H | H | H | 3-OCH₃—Ph | |
| 1.418 | F | H | H | H | 3-Cl—Ph | 194–195 |
| 1.419 | F | H | H | H | 3,4-Cl₂—Ph | |
| 1.420 | F | H | H | H | 3-Cl-4-F—Ph | 208–209 |
| 1.421 | F | H | H | H | 4-SCF₃—Ph | |
| 1.422 | F | H | H | H | 4-SOCF₃—Ph | |
| 1.423 | F | H | H | H | 4-SO₂CF₃—Ph | |
| 1.424 | CH₃ | H | H | H | 4-F—Ph | |
| 1.425 | CH₃ | H | H | H | 4-Cl—Ph | |
| 1.426 | CH₃ | H | H | H | 3-CF₃—Ph | |
| 1.427 | CH₃ | H | H | H | 4-CF₃—Ph | 221–222 |
| 1.428 | CH₃ | H | H | H | 4-OCF₃—Ph | 216–217 |

TABLE 1-continued

Compounds of the formula

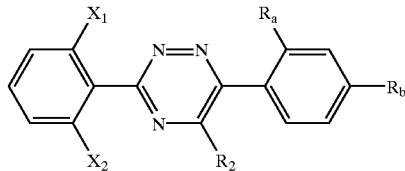

| No. | $X_1$ | $X_2$ | $R_2$ | $R_a$ | $R_b$ | Phys. data |
|---|---|---|---|---|---|---|
| 1.429 | CH$_3$ | H | H | H | 4-t-Butyl-Ph | |
| 1.430 | CH$_3$ | H | H | H | 2,4-Cl$_2$—Ph | |
| 1.431 | CH$_3$ | H | H | H | 3,5-Cl$_2$—Ph | 181–182 |
| 1.432 | CH$_3$ | H | H | H | 2-CF$_3$—Ph | |
| 1.433 | CH$_3$ | H | H | H | 4-OCH$_3$—Ph | |
| 1.434 | CH$_3$ | H | H | H | 4-SCH$_3$—Ph | |
| 1.435 | CH$_3$ | H | H | H | 3-OCH$_3$—Ph | |
| 1.436 | CH$_3$ | H | H | H | 3-Cl—Ph | |
| 1.437 | CH$_3$ | H | H | H | 3,4-Cl$_2$—Ph | |
| 1.438 | CH$_3$ | H | H | H | 3-Cl-4-F—Ph | |
| 1.439 | CH$_3$ | H | H | H | 4-SCF$_3$—Ph | |
| 1.440 | CH$_3$ | H | H | H | 4-SOCF$_3$—Ph | |
| 1.441 | CH$_3$ | H | H | H | 4-SO$_2$CF$_3$—Ph | |
| 1.442 | F | F | OH | H | 4-F—Ph | |
| 1.443 | F | F | OH | H | 4-Cl—Ph | |
| 1.444 | F | F | OH | H | 3-CF$_3$—Ph | |
| 1.445 | F | F | OH | H | 4-CF$_3$—Ph | |
| 1.446 | F | F | OH | H | 4-OCF$_3$—Ph | |
| 1.447 | F | F | OH | H | 4-t-Butyl-Ph | |
| 1.448 | F | F | OH | H | 2,4-Cl$_2$—Ph | |
| 1.449 | F | F | OH | H | 3,5-Cl$_2$—Ph | |
| 1.450 | F | F | OH | H | 2-CF$_3$—Ph | |
| 1.451 | F | F | OH | H | 4-OCH$_3$—Ph | |
| 1.452 | F | F | OH | H | 4-SCH$_3$—Ph | |
| 1.453 | F | F | OH | H | 3-OCH$_3$—Ph | |
| 1.454 | F | F | OH | H | 3-Cl—Ph | |
| 1.455 | F | F | OH | H | 3,4-Cl$_2$—Ph | |
| 1.456 | F | F | OH | H | 3-Cl-4-F—Ph | |
| 1.457 | F | F | OH | H | 4-SCF$_3$—Ph | |
| 1.458 | F | F | OH | H | 4-SOCF$_3$—Ph | |
| 1.459 | F | F | OH | H | 4-SO$_2$CF$_3$—Ph | |
| 1.460 | F | F | OCH$_3$ | H | 4-Cl—Ph | |
| 1.461 | F | F | OCH$_3$ | H | 3-CF$_3$—Ph | |
| 1.462 | F | F | OCH$_3$ | H | 4-CF$_3$—Ph | |
| 1.463 | F | F | OCH$_3$ | H | 4-OCF$_3$—Ph | |
| 1.464 | F | F | OCH$_3$ | H | 4-t-Butyl-Ph | |
| 1.465 | F | F | OCH$_3$ | H | 2,4-Cl$_2$—Ph | |
| 1.466 | F | F | OCH$_3$ | H | 3,5-Cl$_2$—Ph | |
| 1.467 | F | F | OCH$_3$ | H | 2-CF$_3$—Ph | |
| 1.468 | F | F | OCH$_3$ | H | 4-OCH$_3$—Ph | |
| 1.469 | F | F | OCH$_3$ | H | 4-SCH$_3$—Ph | |
| 1.470 | F | F | OCH$_3$ | H | 3-OCH$_3$—Ph | |
| 1.471 | F | F | OCH$_3$ | H | 3-Cl—Ph | |
| 1.472 | F | F | OCH$_3$ | H | 3,4-Cl$_2$—Ph | |
| 1.473 | F | F | OCH$_3$ | H | 3-Cl-4-F—Ph | |
| 1.474 | F | F | OCH$_3$ | H | 4-SCF$_3$—Ph | |
| 1.475 | F | F | OCH$_3$ | H | 4-SOCF$_3$—Ph | |
| 1.476 | F | F | OCH$_3$ | H | 4-SO$_2$CF$_3$—Ph | |
| 1.477 | F | F | Cl | H | 4-F—Ph | |
| 1.478 | F | F | Cl | H | 4-Cl—Ph | |
| 1.479 | F | F | Cl | H | 3-CF$_3$—Ph | |
| 1.480 | F | F | Cl | H | 4-CF$_3$—Ph | |
| 1.481 | F | F | Cl | H | 4-OCF$_3$—Ph | |
| 1.482 | F | F | Cl | H | 4-t-Butyl-Ph | |
| 1.483 | F | F | Cl | H | 2,4-Cl$_2$—Ph | |
| 1.484 | F | F | Cl | H | 3,5-Cl$_2$—Ph | |
| 1.485 | F | F | Cl | H | 2-CF$_3$—Ph | |
| 1.486 | F | F | Cl | H | 4-OCH$_3$—Ph | |
| 1.487 | F | F | Cl | H | 4-SCH$_3$—Ph | |
| 1.488 | F | F | Cl | H | 3-OCH$_3$—Ph | |
| 1.489 | F | F | Cl | H | 3-Cl—Ph | |
| 1.490 | F | F | Cl | H | 3,4-Cl$_2$—Ph | |
| 1.491 | F | F | Cl | H | 3-Cl-4-F—Ph | |
| 1.492 | F | F | Cl | H | 4-SCF$_3$—Ph | |
| 1.493 | F | F | Cl | H | 4-SOCF$_3$—Ph | |

TABLE 1-continued

Compounds of the formula

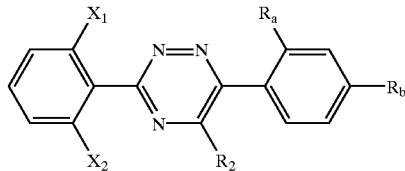

| No. | $X_1$ | $X_2$ | $R_2$ | $R_a$ | $R_b$ | Phys. data |
|---|---|---|---|---|---|---|
| 1.494 | F | F | Cl | H | 4-SO$_2$CF$_3$—Ph | |
| 1.495 | F | F | SCH$_3$ | H | 4-F—Ph | |
| 1.496 | F | F | SCH$_3$ | H | 4-Cl—Ph | |
| 1.497 | F | F | SCH$_3$ | H | 3-CF$_3$—Ph | |
| 1.498 | F | F | SCH$_3$ | H | 4-CF$_3$—Ph | |
| 1.499 | F | F | SCH$_3$ | H | 4-OCF$_3$—Ph | |
| 1.500 | F | F | SCH$_3$ | H | 4-t-Butyl-Ph | |
| 1.501 | F | F | SCH$_3$ | H | 2,4-Cl$_2$—Ph | |
| 1.502 | F | F | SCH$_3$ | H | 3,5-Cl$_2$—Ph | |
| 1.503 | F | F | SCH$_3$ | H | 2-CF$_3$—Ph | |
| 1.504 | F | F | SCH$_3$ | H | 4-OCH$_3$—Ph | |
| 1.505 | F | F | SCH$_3$ | H | 4-SCH$_3$—Ph | |
| 1.506 | F | F | SCH$_3$ | H | 3-OCH$_3$—Ph | |
| 1.507 | F | F | SCH$_3$ | H | 3-Cl—Ph | |
| 1.508 | F | F | SCH$_3$ | H | 3,4-Cl$_2$—Ph | |
| 1.509 | F | F | SCH$_3$ | H | 3-Cl-4-F—Ph | |
| 1.510 | F | F | SCH$_3$ | H | 4-SCF$_3$—Ph | |
| 1.511 | F | F | SCH$_3$ | H | 4-SOCF$_3$—Ph | |
| 1.512 | F | F | SCH$_3$ | H | 4-SO$_2$CF$_3$—Ph | |
| 1.513 | F | F | CN | H | 4-F—Ph | |
| 1.514 | F | F | CN | H | 4-Cl—Ph | |
| 1.515 | F | F | CN | H | 3-CF$_3$—Ph | |
| 1.516 | F | F | CN | H | 4-CF$_3$—Ph | |
| 1.517 | F | F | CN | H | 4-OCF$_3$—Ph | |
| 1.518 | F | F | CN | H | 4-t-Butyl-Ph | |
| 1.519 | F | F | CN | H | 2,4-Cl$_2$—Ph | |
| 1.520 | F | F | CN | H | 3,5-Cl$_2$—Ph | |
| 1.521 | F | F | CN | H | 2-CF$_3$—Ph | |
| 1.522 | F | F | CN | H | 4-OCH$_3$—Ph | |
| 1.523 | F | F | CN | H | 4-SCH$_3$—Ph | |
| 1.524 | F | F | CN | H | 3-OCH$_3$—Ph | |
| 1.525 | F | F | CN | H | 3-Cl—Ph | |
| 1.526 | F | F | CN | H | 3,4-Cl$_2$—Ph | |
| 1.527 | F | F | CN | H | 3-Cl-4-F—Ph | |
| 1.528 | F | F | CN | H | 4-SCF$_3$—Ph | |
| 1.529 | F | F | CN | H | 4-SOCF$_3$—Ph | |
| 1.530 | F | F | CN | H | 4-SO$_2$CF$_3$—Ph | |
| 1.531 | F | F | NHCH$_3$ | H | 4-F—Ph | |
| 1.532 | F | F | NHCH$_3$ | H | 4-Cl—Ph | |
| 1.533 | F | F | NHCH$_3$ | H | 3-CF$_3$—Ph | |
| 1.534 | F | F | NHCH$_3$ | H | 4-CF$_3$—Ph | |
| 1.535 | F | F | NHCH$_3$ | H | 4-OCF$_3$—Ph | |
| 1.536 | F | F | NHCH$_3$ | H | 4-t-Butyl-Ph | |
| 1.537 | F | F | NHCH$_3$ | H | 2,4-Cl$_2$—Ph | |
| 1.538 | F | F | NHCH$_3$ | H | 3,5-Cl$_2$—Ph | |
| 1.539 | F | F | NHCH$_3$ | H | 2-CF$_3$—Ph | |
| 1.540 | F | F | NHCH$_3$ | H | 4-OCH$_3$—Ph | |
| 1.541 | F | F | NHCH$_3$ | H | 4-SCH$_3$—Ph | |
| 1.542 | F | F | NHCH$_3$ | H | 3-OCH$_3$—Ph | |
| 1.543 | F | F | NHCH$_3$ | H | 3-Cl—Ph | |
| 1.544 | F | F | NHCH$_3$ | H | 3,4-Cl$_2$—Ph | |
| 1.545 | F | F | NHCH$_3$ | H | 3-Cl-4-F—Ph | |
| 1.546 | F | F | NHCH$_3$ | H | 4-SCF$_3$—Ph | |
| 1.547 | F | F | NHCH$_3$ | H | 4-SOCF$_3$—Ph | |
| 1.548 | F | F | NHCH$_3$ | H | 4-SO$_2$CF$_3$—Ph | |
| 1.549 | F | F | SH | H | 4-F—Ph | |
| 1.550 | F | F | SH | H | 4-Cl—Ph | |
| 1.551 | F | F | SH | H | 3-CF$_3$—Ph | |
| 1.552 | F | F | SH | H | 4-CF$_3$—Ph | |
| 1.553 | F | F | SH | H | 4-OCF$_3$—Ph | |
| 1.554 | F | F | SH | H | 4-t-Butyl-Ph | |
| 1.555 | F | F | SH | H | 2,4-Cl$_2$—Ph | |
| 1.556 | F | F | SH | H | 3,5-Cl$_2$Ph | |
| 1.557 | F | F | SH | H | 2-CF$_3$—Ph | |
| 1.558 | F | F | SH | H | 4-OCH$_3$—Ph | |

TABLE 1-continued

Compounds of the formula

[Structure: 3-(2,6-disubstituted phenyl)-5-(substituted phenyl)-1,2,4-triazine with X₁, X₂ on one ring and Rₐ, R_b on the other, plus R₂ on the triazine]

| No. | X₁ | X₂ | R₂ | Rₐ | R_b | Phys. data |
|---|---|---|---|---|---|---|
| 1.559 | F | F | SH | H | 4-SCH₃—Ph | |
| 1.560 | F | F | SH | H | 3-OCH₃—Ph | |
| 1.561 | F | F | SH | H | 3-Cl—Ph | |
| 1.562 | F | F | SH | H | 3,4-Cl₂—Ph | |
| 1.563 | F | F | SH | H | 3-Cl-4-F—Ph | |
| 1.564 | F | F | SH | H | 4-SCF₃—Ph | |
| 1.565 | F | F | SH | H | 4-SOCF₃—Ph | |
| 1.566 | F | F | SH | H | 4-SO₂CF₃—Ph | |
| 1.567 | F | F | CH₂NO₂ | H | 4-F—Ph | |
| 1.568 | F | F | CH₂NO₂ | H | 4-Cl—Ph | |
| 1.569 | F | F | CH₂NO₂ | H | 3-CF₃—Ph | |
| 1.570 | F | F | CH₂NO₂ | H | 4-CF₃—Ph | 141–142 |
| 1.571 | F | F | CH₂NO₂ | H | 4-OCF₃—Ph | 137–139 |
| 1.572 | F | F | CH₂NO₂ | H | 4-t-Butyl-Ph | |
| 1.573 | F | F | CH₂NO₂ | H | 2,4-Cl₂—Ph | |
| 1.574 | F | F | CH₂NO₂ | H | 3,5-Cl₂—Ph | |
| 1.575 | F | F | CH₂NO₂ | H | 2-CF₃—Ph | |
| 1.576 | F | F | CH₂NO₂ | H | 4-OCH₃—Ph | |
| 1.577 | F | F | CH₂NO₂ | H | 4-SCH₃—Ph | |
| 1.578 | F | F | CH₂NO₂ | H | 3-OCH₃—Ph | |
| 1.579 | F | F | CH₂NO₂ | H | 3-Cl—Ph | |
| 1.580 | F | F | CH₂NO₂ | H | 3,4-Cl₂—Ph | |
| 1.581 | F | F | CH₂NO₂ | H | 3-Cl-4-F—Ph | |
| 1.582 | F | F | CH₂NO₂ | H | 4-SCF₃—Ph | |
| 1.583 | F | F | CH₂NO₂ | H | 4-SOCF₃—Ph | |
| 1.584 | F | F | CH₂NO₂ | H | 4-SO₂CF₃—Ph | |
| 1.585 | F | F | CH₂SCH₃ | H | 4-F—Ph | |
| 1.586 | F | F | CH₂SCH₃ | H | 4-Cl—Ph | |
| 1.587 | F | F | CH₂SCH₃ | H | 3-CF₃—Ph | |
| 1.588 | F | F | CH₂SCH₃ | H | 4-CF₃—Ph | 174–176 |
| 1.589 | F | F | CH₂SCH₃ | H | 4-OCF₃—Ph | |
| 1.590 | F | F | CH₂SCH₃ | H | 4-t-Butyl-Ph | |
| 1.591 | F | F | CH₂SCH₃ | H | 2,4-Cl₂—Ph | |
| 1.592 | F | F | CH₂SCH₃ | H | 3,5-Cl₂—Ph | |
| 1.593 | F | F | CH₂SCH₃ | H | 2-CF₃—Ph | |
| 1.594 | F | F | CH₂SCH₃ | H | 4-OCH₃—Ph | |
| 1.595 | F | F | CH₂SCH₃ | H | 4-SCH₃—Ph | |
| 1.596 | F | F | CH₂SCH₃ | H | 3-OCH₃—Ph | |
| 1.597 | F | F | CH₂SCH₃ | H | 3-Cl—Ph | |
| 1.598 | F | F | CH₂SCH₃ | H | 3,4-Cl₂—Ph | |
| 1.599 | F | F | CH₂SCH₃ | H | 3-Cl-4-F—Ph | |
| 1.600 | F | F | CH₂SCH₃ | H | 4-SCF₃—Ph | |
| 1.601 | F | F | CH₂SCH₃ | H | 4-SOCF₃—Ph | |
| 1.602 | F | F | CH₂SCH₃ | H | 4-SO₂CF₃—Ph | |
| 1.603 | F | F | H | H | 4-F-Phenoxy | 150–152 |
| 1.604 | F | F | H | H | 4-Cl-Phenoxy | 126–130 |
| 1.605 | F | F | H | H | 3-CF₃-Phenoxy | 111–114 |
| 1.606 | F | F | H | H | 4-CF₃-Phenoxy | |
| 1.607 | F | F | H | H | 4-OCF₃-Phenoxy | 142–144 |
| 1.608 | F | F | H | H | 4-t-Butyl-Phenoxy | 170–173 |
| 1.609 | F | F | H | H | 2,4-Cl₂-Phenoxy | |
| 1.610 | F | F | H | H | 3,5-Cl₂-Phenoxy | 146–148 |
| 1.611 | F | F | H | H | 2-CF₃-Phenoxy | |
| 1.612 | F | F | H | H | 4-OCH₃-Phenoxy | |
| 1.613 | F | F | H | H | 4-SCH₃-Phenoxy | |
| 1.614 | F | F | H | H | 3-OCH₃-Phenoxy | |
| 1.615 | F | F | H | H | 3-Cl-Phenoxy | |
| 1.616 | F | F | H | H | 3,4-Cl₂-Phenoxy | |
| 1.617 | F | F | H | H | 3-Cl-4-F-Phenoxy | |
| 1.618 | F | F | H | H | 4-SCF₃-Phenoxy | |
| 1.619 | F | F | H | H | 4-SOCF₃-Phenoxy | |
| 1.620 | F | F | H | H | 4-SO₂CF₃-Phenoxy | |
| 1.621 | F | F | H | H | 4-F-Phenylamino | |
| 1.622 | F | F | H | H | 4-Cl-Phenylamino | |
| 1.623 | F | F | H | H | 3-CF₃-Phenylamino | |

TABLE 1-continued

Compounds of the formula

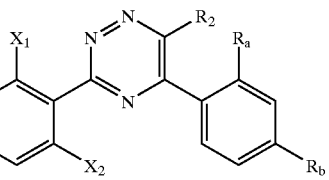

| No. | $X_1$ | $X_2$ | $R_2$ | $R_a$ | $R_b$ | Phys. data |
|---|---|---|---|---|---|---|
| 1.624 | F | F | H | H | 4-CF$_3$-Phenylamino | 222–223 |
| 1.625 | F | F | H | H | 4-OCF$_3$-Phenylamino | |
| 1.626 | F | F | H | H | 4-t-Butyl-Phenylamino | |
| 1.627 | F | F | H | H | 2,4-Cl$_2$-Phenylamino | |
| 1.628 | F | F | H | H | 3,5-Cl$_2$-Phenylamino | |
| 1.629 | F | F | H | H | 2-CF$_3$-Phenylamino | |
| 1.630 | F | F | H | H | 4-OCH$_3$-Phenylamino | |
| 1.631 | F | F | H | H | 4-SCH$_3$-Phenylamino | |
| 1.632 | F | F | H | H | 3-OCH$_3$-Phenylamino | |
| 1.633 | F | F | H | H | 3-Cl-Phenylamino | |
| 1.634 | F | F | H | H | 3,4-Cl$_2$-Phenylamino | |
| 1.635 | F | F | H | H | 3-Cl-4-F-Phenylamino | |
| 1.636 | F | F | H | H | 4-SCF$_3$-Phenylamino | |
| 1.637 | F | F | H | H | 4-SOCF$_3$-Phenylamino | |
| 1.638 | F | F | H | H | 4-SO$_2$CF$_3$-Phenylamino | |
| 1.639 | F | F | H | H | 4-CH$_3$-Phenylamino | 171–172 |

TABLE 2

Compounds of the formula

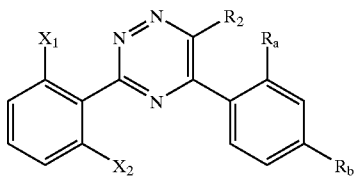

| No. | $X_1$ | $X_2$ | $R_2$ | $R_a$ | $R_b$ | Phys. data |
|---|---|---|---|---|---|---|
| 2.1 | F | F | H | CH$_3$ | 4-F—Ph | |
| 2.2 | F | F | H | CH$_3$ | 4-Cl—Ph | 171–173 |
| 2.3 | F | F | H | CH$_3$ | 3-CF$_3$—Ph | 119–121 |
| 2.4 | F | F | H | CH$_3$ | 4-CF$_3$—Ph | 121–124 |
| 2.5 | F | F | H | CH$_3$ | 4-OCF$_3$—Ph | 165–167 |
| 2.6 | F | F | H | CH$_3$ | 4-tert-butyl-Ph | |
| 2.7 | F | F | H | CH$_3$ | 2,4-Cl$_2$—Ph | |
| 2.8 | F | F | H | CH$_3$ | 3,5-Cl$_2$—Ph | 195–197 |
| 2.9 | F | F | H | CH$_3$ | 2-CF$_3$—Ph | |
| 2.10 | F | F | H | CH$_3$ | 4-OCH$_3$—Ph | |
| 2.11 | F | F | H | CH$_3$ | 4-SCH$_3$—Ph | |
| 2.12 | F | F | H | CH$_3$ | 3-OCH$_3$—Ph | |
| 2.13 | F | F | H | CH$_3$ | 3-Cl—Ph | |
| 2.14 | F | F | H | CH$_3$ | 3,4-Cl$_2$—Ph | |
| 2.15 | F | F | H | CH$_3$ | 3-Cl-4-F—Ph | 174–176 |
| 2.16 | F | F | H | OCH$_3$ | 4-F—Ph | |
| 2.17 | F | F | H | OCH$_3$ | 4-Cl—Ph | 151–152 |
| 2.18 | F | F | H | OCH$_3$ | 3-CF$_3$—Ph | 117–118 |
| 2.19 | F | F | H | OCH$_3$ | 4-CF$_3$—Ph | 145–146 |
| 2.20 | F | F | H | OCH$_3$ | 4-OCF$_3$—Ph | 109–111 |
| 2.21 | F | F | H | OCH$_3$ | 4-tert-butyl-Ph | |
| 2.22 | F | F | H | OCH$_3$ | 2,4-Cl$_2$—Ph | |
| 2.23 | F | F | H | OCH$_3$ | 3,5-Cl$_2$—Ph | 210–211 |
| 2.24 | F | F | H | OCH$_3$ | 2-CF$_3$—Ph | |
| 2.25 | F | F | H | OCH$_3$ | 4-OCH$_3$—Ph | |
| 2.26 | F | F | H | OCH$_3$ | 4-SCH$_3$—Ph | |
| 2.27 | F | F | H | OCH$_3$ | 3-OCH$_3$—Ph | |
| 2.28 | F | F | H | OCH$_3$ | 3-Cl—Ph | |
| 2.29 | F | F | H | OCH$_3$ | 3,4-Cl$_2$—Ph | |
| 2.30 | F | F | H | OCH$_3$ | 3-Cl-4-F—Ph | 196–197 |
| 2.31 | F | F | H | OCH$_3$ | 4-Br | 165–166 |
| 2.32 | F | F | H | CF$_3$ | 4-F—Ph | |
| 2.33 | F | F | H | CF$_3$ | 4-Cl—Ph | |
| 2.34 | F | F | H | CF$_3$ | 3-CF$_3$—Ph | |
| 2.35 | F | F | H | CF$_3$ | 4-CF$_3$—Ph | |
| 2.36 | F | F | H | CF$_3$ | 4-OCF$_3$—Ph | |
| 2.37 | F | F | H | CF$_3$ | 4-tert-butyl-Ph | |
| 2.38 | F | F | H | CF$_3$ | 2,4-Cl$_2$—Ph | |
| 2.39 | F | F | H | CF$_3$ | 3,5-Cl$_2$—Ph | |
| 2.40 | F | F | H | CF$_3$ | 2-CF$_3$—Ph | |
| 2.41 | F | F | H | CF$_3$ | 4-OCH$_3$—Ph | |
| 2.42 | F | F | H | CF$_3$ | 4-SCH$_3$—Ph | |
| 2.43 | F | F | H | CF$_3$ | 3-OCH$_3$—Ph | |
| 2.44 | F | F | H | CF$_3$ | 3-Cl—Ph | |
| 2.45 | F | F | H | CF$_3$ | 3,4-Cl$_2$—Ph | |
| 2.46 | F | F | H | CF$_3$ | 3-Cl-4-F—Ph | |
| 2.47 | F | F | CH$_3$ | H | 4-F—Ph | |
| 2.48 | F | F | CH$_3$ | H | 4-Cl—Ph | |
| 2.49 | F | F | CH$_3$ | H | 3-CF$_3$—Ph | |
| 2.50 | F | F | CH$_3$ | H | 4-CF$_3$—Ph | |
| 2.51 | F | F | CH$_3$ | H | 4-OCF$_3$—Ph | |
| 2.52 | F | F | CH$_3$ | H | 4-tert-butyl-Ph | |
| 2.53 | F | F | CH$_3$ | H | 2,4-Cl$_2$—Ph | |
| 2.54 | F | F | CH$_3$ | H | 3,5-Cl$_2$—Ph | |
| 2.55 | F | F | CH$_3$ | H | 2-CF$_3$—Ph | |
| 2.56 | F | F | CH$_3$ | H | 4-OCH$_3$—Ph | |
| 2.57 | F | F | CH$_3$ | H | 4-SCH$_3$—Ph | |
| 2.58 | F | F | CH$_3$ | H | 3-OCH$_3$—Ph | |
| 2.59 | F | F | CH$_3$ | H | 3-Cl—Ph | |
| 2.60 | F | F | CH$_3$ | H | 3,4-Cl$_2$—Ph | |

TABLE 2-continued

Compounds of the formula

| No. | $X_1$ | $X_2$ | $R_2$ | $R_a$ | $R_b$ | Phys. data |
|---|---|---|---|---|---|---|
| 2.61 | F | F | $CH_3$ | H | 3-Cl-4-F—Ph | |
| 2.62 | F | F | $CH_3$ | $CH_3$ | 4-F—Ph | |
| 2.63 | F | F | $CH_3$ | $CH_3$ | 4-Cl—Ph | |
| 2.64 | F | F | $CH_3$ | $CH_3$ | 3-$CF_3$—Ph | |
| 2.65 | F | F | $CH_3$ | $CH_3$ | 4-$CF_3$—Ph | |
| 2.66 | F | F | $CH_3$ | $CH_3$ | 4-$OCF_3$—Ph | |
| 2.67 | F | F | $CH_3$ | $CH_3$ | 4-tert-butyl-Ph | |
| 2.68 | F | F | $CH_3$ | $CH_3$ | 2,4-$Cl_2$—Ph | |
| 2.69 | F | F | $CH_3$ | $CH_3$ | 3,5-$Cl_2$—Ph | |
| 2.70 | F | F | $CH_3$ | $CH_3$ | 2-$CF_3$—Ph | |
| 2.71 | F | F | $CH_3$ | $CH_3$ | 4-$OCH_3$—Ph | |
| 2.72 | F | F | $CH_3$ | $CH_3$ | 4-$SCH_3$—Ph | |
| 2.73 | F | F | $CH_3$ | $CH_3$ | 3-$OCH_3$—Ph | |
| 2.74 | F | F | $CH_3$ | $CH_3$ | 3-Cl—Ph | |
| 2.75 | F | F | $CH_3$ | $CH_3$ | 3,4-$Cl_2$—Ph | |
| 2.76 | F | F | $CH_3$ | $CH_3$ | 3-Cl-4-F—Ph | |
| 2.77 | F | F | $CH_3$ | $OCH_3$ | 4-F—Ph | |
| 2.78 | F | F | $CH_3$ | $OCH_3$ | 4-Cl—Ph | |
| 2.79 | F | F | $CH_3$ | $OCH_3$ | 3-$CF_3$—Ph | |
| 2.80 | F | F | $CH_3$ | $OCH_3$ | 4-$CF_3$—Ph | |
| 2.81 | F | F | $CH_3$ | $OCH_3$ | 4-$OCF_3$—Ph | |
| 2.82 | F | F | $CH_3$ | $OCH_3$ | 4-tert-butyl-Ph | |
| 2.83 | F | F | $CH_3$ | $OCH_3$ | 2,4-$Cl_2$—Ph | |
| 2.84 | F | F | $CH_3$ | $OCH_3$ | 3,5-$Cl_2$—Ph | |
| 2.85 | F | F | $CH_3$ | $OCH_3$ | 2-$CF_3$—Ph | |
| 2.86 | F | F | $CH_3$ | $OCH_3$ | 4-$OCH_3$—Ph | |
| 2.87 | F | F | $CH_3$ | $OCH_3$ | 4-$SCH_3$—Ph | |
| 2.88 | F | F | $CH_3$ | $OCH_3$ | 3-$OCH_3$—Ph | |
| 2.89 | F | F | $CH_3$ | $OCH_3$ | 3-Cl—Ph | |
| 2.90 | F | F | $CH_3$ | $OCH_3$ | 3,4-$Cl_2$—Ph | |
| 2.91 | F | F | $CH_3$ | $OCH_3$ | 3-Cl-4-F—Ph | |
| 2.92 | F | F | $CH_3$ | $CF_3$ | 4-F—Ph | |
| 2.93 | F | F | $CH_3$ | $CF_3$ | 4-Cl—Ph | |
| 2.94 | F | F | $CH_3$ | $CF_3$ | 3-$CF_3$—Ph | |
| 2.95 | F | F | $CH_3$ | $CF_3$ | 4-$CF_3$—Ph | |
| 2.96 | F | F | $CH_3$ | $CF_3$ | 4-$OCF_3$—Ph | |
| 2.97 | F | F | $CH_3$ | $CF_3$ | 4-tert-butyl-Ph | |
| 2.98 | F | F | $CH_3$ | $CF_3$ | 2,4-$Cl_2$—Ph | |
| 2.99 | F | F | $CH_3$ | $CF_3$ | 3,5-$Cl_2$—Ph | |
| 2.100 | F | F | $CH_3$ | $CF_3$ | 2-$CF_3$—Ph | |
| 2.101 | F | F | $CH_3$ | $CF_3$ | 4-$OCH_3$—Ph | |
| 2.102 | F | F | $CH_3$ | $CF_3$ | 4-$SCH_3$—Ph | |
| 2.103 | F | F | $CH_3$ | $CF_3$ | 3-$OCH_3$—Ph | |
| 2.104 | F | F | $CH_3$ | $CF_3$ | 3-Cl—Ph | |
| 2.105 | F | F | $CH_3$ | $CF_3$ | 3,4-$Cl_2$—Ph | |
| 2.106 | F | F | $CH_3$ | $CF_3$ | 3-Cl-4-F—Ph | |
| 2.107 | F | Cl | H | H | 4-F—Ph | |
| 2.108 | F | Cl | H | H | 4-Cl—Ph | |
| 2.109 | F | Cl | H | H | 3-$CF_3$—Ph | |
| 2.110 | F | Cl | H | H | 4-$CF_3$—Ph | |
| 2.111 | F | Cl | H | H | 4-$OCF_3$—Ph | |
| 2.112 | F | Cl | H | H | 4-tert-butyl-Ph | |
| 2.113 | F | Cl | H | H | 2,4-$Cl_2$—Ph | |
| 2.114 | F | Cl | H | H | 3,5-$Cl_2$—Ph | |
| 2.115 | F | Cl | H | H | 2-$CF_3$—Ph | |
| 2.116 | F | Cl | H | H | 4-$OCH_3$—Ph | |
| 2.117 | F | Cl | H | H | 4-$SCH_3$—Ph | |
| 2.118 | F | Cl | H | H | 3-$OCH_3$—Ph | |
| 2.119 | F | Cl | H | H | 3-Cl—Ph | |
| 2.120 | F | Cl | H | H | 3,4-$Cl_2$—Ph | |
| 2.121 | F | Cl | H | H | 3-Cl-4-F—Ph | |
| 2.122 | F | Cl | H | $CH_3$ | 4-F—Ph | |
| 2.123 | F | Cl | H | $CH_3$ | 4-Cl—Ph | |
| 2.124 | F | Cl | H | $CH_3$ | 3-$CF_3$—Ph | |
| 2.125 | F | Cl | H | $CH_3$ | 4-$CF_3$—Ph | |
| 2.126 | F | Cl | H | $CH_3$ | 4-$OCF_3$—Ph | |
| 2.127 | F | Cl | H | $CH_3$ | 4-tert-butyl-Ph | |
| 2.128 | F | Cl | H | $CH_3$ | 2,4-$Cl_2$—Ph | |
| 2.129 | F | Cl | H | $CH_3$ | 3,5-$Cl_2$—Ph | |
| 2.130 | F | Cl | H | $CH_3$ | 2-$CF_3$—Ph | |
| 2.131 | F | Cl | H | $CH_3$ | 4-$OCH_3$—Ph | |
| 2.132 | F | Cl | H | $CH_3$ | 4-$SCH_3$—Ph | |
| 2.133 | F | Cl | H | $CH_3$ | 3-$OCH_3$—Ph | |
| 2.134 | F | Cl | H | $CH_3$ | 3-Cl—Ph | |
| 2.135 | F | Cl | H | $CH_3$ | 3,4-$Cl_2$—Ph | |
| 2.136 | F | Cl | H | $CH_3$ | 3-Cl-4-F—Ph | |
| 2.137 | F | Cl | H | $OCH_3$ | 4-F—Ph | |
| 2.138 | F | Cl | H | $OCH_3$ | 4-Cl—Ph | |
| 2.139 | F | Cl | H | $OCH_3$ | 3-$CF_3$—Ph | |
| 2.140 | F | Cl | H | $OCH_3$ | 4-$CF_3$—Ph | |
| 2.141 | F | Cl | H | $OCH_3$ | 4-$OCF_3$—Ph | |
| 2.142 | F | Cl | H | $OCH_3$ | 4-tert-butyl-Ph | |
| 2.143 | F | Cl | H | $OCH_3$ | 2,4-$Cl_2$—Ph | |
| 2.144 | F | Cl | H | $OCH_3$ | 3,5-$Cl_2$—Ph | |
| 2.145 | F | Cl | H | $OCH_3$ | 2-$CF_3$—Ph | |
| 2.146 | F | Cl | H | $OCH_3$ | 4-$OCH_3$—Ph | |
| 2.147 | F | Cl | H | $OCH_3$ | 4-$SCH_3$—Ph | |
| 2.148 | F | Cl | H | $OCH_3$ | 3-$OCH_3$—Ph | |
| 2.149 | F | Cl | H | $OCH_3$ | 3-Cl—Ph | |
| 2.150 | F | Cl | H | $OCH_3$ | 3,4-$Cl_2$—Ph | |
| 2.151 | F | Cl | H | $OCH_3$ | 3-Cl-4-F—Ph | |
| 2.152 | F | Cl | H | $CF_3$ | 4-F—Ph | |
| 2.153 | F | Cl | H | $CF_3$ | 4-Cl—Ph | |
| 2.154 | F | Cl | H | $CF_3$ | 3-$CF_3$—Ph | |
| 2.155 | F | Cl | H | $CF_3$ | 4-$CF_3$—Ph | |
| 2.156 | F | Cl | H | $CF_3$ | 4-$OCF_3$—Ph | |
| 2.157 | F | Cl | H | $CF_3$ | 4-tert-butyl-Ph | |
| 2.158 | F | Cl | H | $CF_3$ | 2,4-$Cl_2$—Ph | |
| 2.159 | F | Cl | H | $CF_3$ | 3,5-$Cl_2$—Ph | |
| 2.160 | F | Cl | H | $CF_3$ | 2-$CF_3$—Ph | |
| 2.161 | F | Cl | H | $CF_3$ | 4-$OCH_3$—Ph | |
| 2.162 | F | Cl | H | $CF_3$ | 4-$SCH_3$—Ph | |
| 2.163 | F | Cl | H | $CF_3$ | 3-$OCH_3$—Ph | |
| 2.164 | F | Cl | H | $CF_3$ | 3-Cl—Ph | |
| 2.165 | F | Cl | H | $CF_3$ | 3,4-$Cl_2$—Ph | |
| 2.166 | F | Cl | H | $CF_3$ | 3-Cl-4-F—Ph | |
| 2.167 | F | Cl | $CH_3$ | H | 4-F—Ph | |
| 2.168 | F | Cl | $CH_3$ | H | 4-Cl—Ph | |
| 2.169 | F | Cl | $CH_3$ | H | 3-$CF_3$—Ph | |
| 2.170 | F | Cl | $CH_3$ | H | 4-$CF_3$—Ph | |
| 2.171 | F | Cl | $CH_3$ | H | 4-$OCF_3$—Ph | |
| 2.172 | F | Cl | $CH_3$ | H | 4-tert-butyl-Ph | |
| 2.173 | F | Cl | $CH_3$ | H | 2,4-$Cl_2$—Ph | |
| 2.174 | F | Cl | $CH_3$ | H | 3,5-$Cl_2$—Ph | |
| 2.175 | F | Cl | $CH_3$ | H | 2-$CF_3$—Ph | |
| 2.176 | F | Cl | $CH_3$ | H | 4-$OCH_3$—Ph | |
| 2.177 | F | Cl | $CH_3$ | H | 4-$SCH_3$—Ph | |
| 2.178 | F | Cl | $CH_3$ | H | 3-$OCH_3$—Ph | |
| 2.179 | F | Cl | $CH_3$ | H | 3-Cl—Ph | |
| 2.180 | F | Cl | $CH_3$ | H | 3,4-$Cl_2$—Ph | |
| 2.181 | F | Cl | $CH_3$ | H | 3-Cl-4-F—Ph | |
| 2.182 | F | Cl | $CH_3$ | $CH_3$ | 4-F—Ph | |
| 2.183 | F | Cl | $CH_3$ | $CH_3$ | 4-Cl—Ph | |
| 2.184 | F | Cl | $CH_3$ | $CH_3$ | 3-$CF_3$—Ph | |
| 2.185 | F | Cl | $CH_3$ | $CH_3$ | 4-$CF_3$—Ph | |
| 2.186 | F | Cl | $CH_3$ | $CH_3$ | 4-$OCF_3$—Ph | |
| 2.187 | F | Cl | $CH_3$ | $CH_3$ | 4-tert-butyl-Ph | |
| 2.188 | F | Cl | $CH_3$ | $CH_3$ | 2,4-$Cl_2$—Ph | |
| 2.189 | F | Cl | $CH_3$ | $CH_3$ | 3,5-$Cl_2$—Ph | |
| 2.190 | F | Cl | $CH_3$ | $CH_3$ | 2-$CF_3$—Ph | |

TABLE 2-continued

Compounds of the formula

| No. | X₁ | X₂ | R₂ | Rₐ | R_b | Phys. data |
|---|---|---|---|---|---|---|
| 2.191 | F | Cl | CH₃ | CH₃ | 4-OCH₃—Ph | |
| 2.192 | F | Cl | CH₃ | CH₃ | 4-SCH₃—Ph | |
| 2.193 | F | Cl | CH₃ | CH₃ | 3-OCH₃—Ph | |
| 2.194 | F | Cl | CH₃ | CH₃ | 3-Cl—Ph | |
| 2.195 | F | Cl | CH₃ | CH₃ | 3,4-Cl₂—Ph | |
| 2.196 | F | Cl | CH₃ | CH₃ | 3-Cl-4-F—Ph | |
| 2.197 | F | Cl | CH₃ | OCH₃ | 4-F—Ph | |
| 2.198 | F | Cl | CH₃ | OCH₃ | 4-Cl—Ph | |
| 2.199 | F | Cl | CH₃ | OCH₃ | 3-CF₃—Ph | |
| 2.200 | F | Cl | CH₃ | OCH₃ | 4-CF₃—Ph | |
| 2.201 | F | Cl | CH₃ | OCH₃ | 4-OCF₃—Ph | |
| 2.202 | F | Cl | CH₃ | OCH₃ | 4-tert-butyl-Ph | |
| 2.203 | F | Cl | CH₃ | OCH₃ | 2,4-Cl₂—Ph | |
| 2.204 | F | Cl | CH₃ | OCH₃ | 3,5-Cl₂—Ph | |
| 2.205 | F | Cl | CH₃ | OCH₃ | 2-CF₃—Ph | |
| 2.206 | F | Cl | CH₃ | OCH₃ | 4-OCH₃—Ph | |
| 2.207 | F | Cl | CH₃ | OCH₃ | 4-SCH₃—Ph | |
| 2.208 | F | Cl | CH₃ | OCH₃ | 3-OCH₃—Ph | |
| 2.209 | F | Cl | CH₃ | OCH₃ | 3-Cl—Ph | |
| 2.210 | F | Cl | CH₃ | OCH₃ | 3,4-Cl₂—Ph | |
| 2.211 | F | Cl | CH₃ | OCH₃ | 3-Cl-4-F—Ph | |
| 2.212 | F | Cl | CH₃ | CF₃ | 4-F—Ph | |
| 2.213 | F | Cl | CH₃ | CF₃ | 4-Cl—Ph | |
| 2.214 | F | Cl | CH₃ | CF₃ | 3-CF₃—Ph | |
| 2.215 | F | Cl | CH₃ | CF₃ | 4-CF₃—Ph | |
| 2.216 | F | Cl | CH₃ | CF₃ | 4-OCF₃—Ph | |
| 2.217 | F | Cl | CH₃ | CF₃ | 4-tert-butyl-Ph | |
| 2.218 | F | Cl | CH₃ | CF₃ | 2,4-Cl₂—Ph | |
| 2.219 | F | Cl | CH₃ | CF₃ | 3,5-Cl₂—Ph | |
| 2.220 | F | Cl | CH₃ | CF₃ | 2-CF₃—Ph | |
| 2.221 | F | Cl | CH₃ | CF₃ | 4-OCH₃—Ph | |
| 2.222 | F | Cl | CH₃ | CF₃ | 4-SCH₃—Ph | |
| 2.223 | F | Cl | CH₃ | CF₃ | 3-OCH₃—Ph | |
| 2.224 | F | Cl | CH₃ | CF₃ | 3-Cl—Ph | |
| 2.225 | F | Cl | CH₃ | CF₃ | 3,4-Cl₂—Ph | |
| 2.226 | F | Cl | CH₃ | CF₃ | 3-Cl-4-F—Ph | |
| 2.227 | Cl | Cl | H | H | 4-F—Ph | |
| 2.228 | Cl | Cl | H | H | 4-Cl—Ph | |
| 2.229 | Cl | Cl | H | H | 3-CF₃—Ph | |
| 2.230 | Cl | Cl | H | H | 4-CF₃—Ph | |
| 2.231 | Cl | Cl | H | H | 4-OCF₃—Ph | |
| 2.232 | Cl | Cl | H | H | 4-tert-butyl-Ph | |
| 2.233 | Cl | Cl | H | H | 2,4-Cl₂—Ph | |
| 2.234 | Cl | Cl | H | H | 3,5-Cl₂—Ph | |
| 2.235 | Cl | Cl | H | H | 2-CF₃—Ph | |
| 2.236 | Cl | Cl | H | H | 4-OCH₃—Ph | |
| 2.237 | Cl | Cl | H | H | 4-SCH₃—Ph | |
| 2.238 | Cl | Cl | H | H | 3-OCH₃—Ph | |
| 2.239 | Cl | Cl | H | H | 3-Cl—Ph | |
| 2.240 | Cl | Cl | H | H | 3,4-Cl₂—Ph | |
| 2.241 | Cl | Cl | H | H | 3-Cl-4-F—Ph | |
| 2.242 | Cl | Cl | H | CH₃ | 4-F—Ph | |
| 2.243 | Cl | Cl | H | CH₃ | 4-Cl—Ph | |
| 2.244 | Cl | Cl | H | CH₃ | 3-CF₃—Ph | |
| 2.245 | Cl | Cl | H | CH₃ | 4-CF₃—Ph | |
| 2.246 | Cl | Cl | H | CH₃ | 4-OCF₃—Ph | |
| 2.247 | Cl | Cl | H | CH₃ | 4-tert-butyl-Ph | |
| 2.248 | Cl | Cl | H | CH₃ | 2,4-Cl₂—Ph | |
| 2.249 | Cl | Cl | H | CH₃ | 3,5-Cl₂—Ph | |
| 2.250 | Cl | Cl | H | CH₃ | 2-CF₃—Ph | |
| 2.251 | Cl | Cl | H | CH₃ | 4-OCH₃—Ph | |
| 2.252 | Cl | Cl | H | CH₃ | 4-SCH₃—Ph | |
| 2.253 | Cl | Cl | H | CH₃ | 3-OCH₃—Ph | |
| 2.254 | Cl | Cl | H | CH₃ | 3-Cl—Ph | |
| 2.255 | Cl | Cl | H | CH₃ | 3,4-Cl₂—Ph | |
| 2.256 | Cl | Cl | H | CH₃ | 3-Cl-4-F—Ph | |
| 2.257 | Cl | Cl | H | OCH₃ | 4-F—Ph | |
| 2.258 | Cl | Cl | H | OCH₃ | 4-Cl—Ph | |
| 2.259 | Cl | Cl | H | OCH₃ | 3-CF₃—Ph | |
| 2.260 | Cl | Cl | H | OCH₃ | 4-CF₃—Ph | |
| 2.261 | Cl | Cl | H | OCH₃ | 4-OCF₃—Ph | |
| 2.262 | Cl | Cl | H | OCH₃ | 4-tert-butyl-Ph | |
| 2.263 | Cl | Cl | H | OCH₃ | 2,4-Cl₂—Ph | |
| 2.264 | Cl | Cl | H | OCH₃ | 3,5-Cl₂—Ph | |
| 2.265 | Cl | Cl | H | OCH₃ | 2-CF₃—Ph | |
| 2.266 | Cl | Cl | H | OCH₃ | 4-OCH₃—Ph | |
| 2.267 | Cl | Cl | H | OCH₃ | 4-SCH₃—Ph | |
| 2.268 | Cl | Cl | H | OCH₃ | 3-OCH₃—Ph | |
| 2.269 | Cl | Cl | H | OCH₃ | 3-Cl—Ph | |
| 2.270 | Cl | Cl | H | OCH₃ | 3,4-Cl₂—Ph | |
| 2.271 | Cl | Cl | H | OCH₃ | 3-Cl-4-F—Ph | |
| 2.272 | Cl | Cl | H | CF₃ | 4-F—Ph | |
| 2.273 | Cl | Cl | H | CF₃ | 4-Cl—Ph | |
| 2.274 | Cl | Cl | H | CF₃ | 3-CF₃—Ph | |
| 2.275 | Cl | Cl | H | CF₃ | 4-CF₃—Ph | |
| 2.276 | Cl | Cl | H | CF₃ | 4-OCF₃—Ph | |
| 2.277 | Cl | Cl | H | CF₃ | 4-tert-butyl-Ph | |
| 2.278 | Cl | Cl | H | CF₃ | 2,4-Cl₂—Ph | |
| 2.279 | Cl | Cl | H | CF₃ | 3,5-Cl₂—Ph | |
| 2.280 | Cl | Cl | H | CF₃ | 2-CF₃—Ph | |
| 2.281 | Cl | Cl | H | CF₃ | 4-OCH₃—Ph | |
| 2.282 | Cl | Cl | H | CF₃ | 4-SCH₃—Ph | |
| 2.283 | Cl | Cl | H | CF₃ | 3-OCH₃—Ph | |
| 2.284 | Cl | Cl | H | CF₃ | 3-Cl—Ph | |
| 2.285 | Cl | Cl | H | CF₃ | 3,4-Cl₂—Ph | |
| 2.286 | Cl | Cl | H | CF₃ | 3-Cl-4-F—Ph | |
| 2.287 | Cl | Cl | CH₃ | H | 4-F—Ph | |
| 2.288 | Cl | Cl | CH₃ | H | 4-Cl—Ph | |
| 2.289 | Cl | Cl | CH₃ | H | 3-CF₃—Ph | |
| 2.290 | Cl | Cl | CH₃ | H | 4-CF₃—Ph | |
| 2.291 | Cl | Cl | CH₃ | H | 4-OCF₃—Ph | |
| 2.292 | Cl | Cl | CH₃ | H | 4-tert-butyl-Ph | |
| 2.293 | Cl | Cl | CH₃ | H | 2,4-Cl₂—Ph | |
| 2.294 | Cl | Cl | CH₃ | H | 3,5-Cl₂—Ph | |
| 2.295 | Cl | Cl | CH₃ | H | 2-CF₃—Ph | |
| 2.296 | Cl | Cl | CH₃ | H | 4-OCH₃—Ph | |
| 2.297 | Cl | Cl | CH₃ | H | 4-SCH₃—Ph | |
| 2.298 | Cl | Cl | CH₃ | H | 3-OCH₃—Ph | |
| 2.299 | Cl | Cl | CH₃ | H | 3-Cl—Ph | |
| 2.300 | Cl | Cl | CH₃ | H | 3,4-Cl₂—Ph | |
| 2.301 | Cl | Cl | CH₃ | H | 3-Cl-4-F—Ph | |
| 2.302 | Cl | Cl | CH₃ | CH₃ | 4-F—Ph | |
| 2.303 | Cl | Cl | CH₃ | CH₃ | 4-Cl—Ph | |
| 2.304 | Cl | Cl | CH₃ | CH₃ | 3-CF₃—Ph | |
| 2.305 | Cl | Cl | CH₃ | CH₃ | 4-CF₃—Ph | |
| 2.306 | Cl | Cl | CH₃ | CH₃ | 4-OCF₃—Ph | |
| 2.307 | Cl | Cl | CH₃ | CH₃ | 4-tert-butyl-Ph | |
| 2.308 | Cl | Cl | CH₃ | CH₃ | 2,4-Cl₂—Ph | |
| 2.309 | Cl | Cl | CH₃ | CH₃ | 3,5-Cl₂—Ph | |
| 2.310 | Cl | Cl | CH₃ | CH₃ | 2-CF₃—Ph | |
| 2.311 | Cl | Cl | CH₃ | CH₃ | 4-OCH₃—Ph | |
| 2.312 | Cl | Cl | CH₃ | CH₃ | 4-SCH₃—Ph | |
| 2.313 | Cl | Cl | CH₃ | CH₃ | 3-OCH₃—Ph | |
| 2.314 | Cl | Cl | CH₃ | CH₃ | 3-Cl—Ph | |
| 2.315 | Cl | Cl | CH₃ | CH₃ | 3,4-Cl₂—Ph | |
| 2.316 | Cl | Cl | CH₃ | CH₃ | 3-Cl-4-F—Ph | |
| 2.317 | Cl | Cl | CH₃ | OCH₃ | 4-F—Ph | |
| 2.318 | Cl | Cl | CH₃ | OCH₃ | 4-Cl—Ph | |
| 2.319 | Cl | Cl | CH₃ | OCH₃ | 3-CF₃—Ph | |
| 2.320 | Cl | Cl | CH₃ | OCH₃ | 4-CF₃—Ph | |

TABLE 2-continued

Compounds of the formula

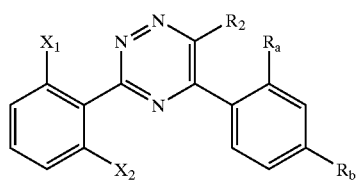

| No. | $X_1$ | $X_2$ | $R_2$ | $R_a$ | $R_b$ | Phys. data |
|---|---|---|---|---|---|---|
| 2.321 | Cl | Cl | $CH_3$ | $OCH_3$ | 4-$OCF_3$—Ph | |
| 2.322 | Cl | Cl | $CH_3$ | $OCH_3$ | 4-tert-butyl-Ph | |
| 2.323 | Cl | Cl | $CH_3$ | $OCH_3$ | 2,4-$Cl_2$—Ph | |
| 2.324 | Cl | Cl | $CH_3$ | $OCH_3$ | 3,5-$Cl_2$—Ph | |
| 2.325 | Cl | Cl | $CH_3$ | $OCH_3$ | 2-$CF_3$—Ph | |
| 2.326 | Cl | Cl | $CH_3$ | $OCH_3$ | 4-$OCH_3$—Ph | |
| 2.327 | Cl | Cl | $CH_3$ | $OCH_3$ | 4-$SCH_3$—Ph | |
| 2.328 | Cl | Cl | $CH_3$ | $OCH_3$ | 3-$OCH_3$—Ph | |
| 2.329 | Cl | Cl | $CH_3$ | $OCH_3$ | 3-Cl—Ph | |
| 2.330 | Cl | Cl | $CH_3$ | $OCH_3$ | 3,4-$Cl_2$—Ph | |
| 2.331 | Cl | Cl | $CH_3$ | $OCH_3$ | 3-Cl-4-F—Ph | |
| 2.332 | Cl | Cl | $CH_3$ | $CF_3$ | 4-F—Ph | |
| 2.333 | Cl | Cl | $CH_3$ | $CF_3$ | 4-Cl—Ph | |
| 2.334 | Cl | Cl | $CH_3$ | $CF_3$ | 3-$CF_3$—Ph | |
| 2.335 | Cl | Cl | $CH_3$ | $CF_3$ | 4-$CF_3$—Ph | |
| 2.336 | Cl | Cl | $CH_3$ | $CF_3$ | 4-$OCF_3$—Ph | |
| 2.337 | Cl | Cl | $CH_3$ | $CF_3$ | 4-tert-butyl-Ph | |
| 2.338 | Cl | Cl | $CH_3$ | $CF_3$ | 2,4-$Cl_2$—Ph | |

TABLE 2-continued

Compounds of the formula

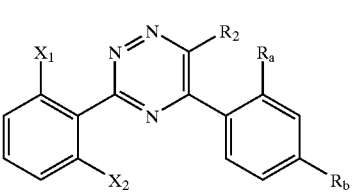

| No. | $X_1$ | $X_2$ | $R_2$ | $R_a$ | $R_b$ | Phys. data |
|---|---|---|---|---|---|---|
| 2.339 | Cl | Cl | $CH_3$ | $CF_3$ | 3,5-$Cl_2$—Ph | |
| 2.340 | Cl | Cl | $CH_3$ | $CF_3$ | 2-$CF_3$—Ph | |
| 2.341 | Cl | Cl | $CH_3$ | $CF_3$ | 4-$OCH_3$—Ph | |
| 2.342 | Cl | Cl | $CH_3$ | $CF_3$ | 4-$SCH_3$—Ph | |
| 2.343 | Cl | Cl | $CH_3$ | $CF_3$ | 3-$OCH_3$—Ph | |
| 2.344 | Cl | Cl | $CH_3$ | $CF_3$ | 3-Cl—Ph | |
| 2.345 | Cl | Cl | $CH_3$ | $CF_3$ | 3,4-$Cl_2$—Ph | |
| 2.346 | Cl | Cl | $CH_3$ | $CF_3$ | 3-Cl-4-F—Ph | |
| 2.347 | Cl | H | F | H | 4-$CF_3$—Ph | |
| 2.348 | F | F | H | H | 3,4-$Cl_2$—Ph | solid |
| 2.349 | F | F | H | H | 4-$SCH_3$—Ph | 125–129 |
| 2.350 | F | F | H | H | 2-$CH_3$—Ph | |

TABLE 3

Compounds of the formula

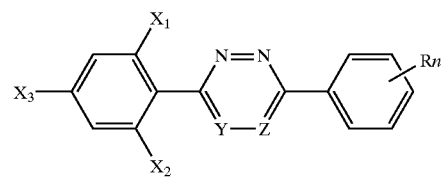

| No. | $X_1$ | $X_2$ | $X_3$ | Y | Z | $R_n$ | Phys. data[1] |
|---|---|---|---|---|---|---|---|
| 3.1 | Cl | H | Cl | N | CH | 4-OPh | $MH^+$: 394 |
| 3.2 | Cl | H | Cl | N | CH | 4-$CF_3$ | |
| 3.3 | Cl | H | Cl | N | CH | 4-(3-$CF_3$—Ph) | |
| 3.4 | Cl | H | Cl | N | CH | 4-(4-$CF_3$—Ph) | $MH^+$: 446 |
| 3.5 | Cl | H | Cl | N | CH | 4-(2,4-$Cl_2$—Ph) | $MH^+$: 446 |
| 3.6 | Cl | H | Cl | N | CH | 2,4-$Cl_2$ | $MH^+$: 369.9 |
| 3.7 | F | F | H | N | CH | 4-(4-$CH_3$—Ph) | $MH^+$: 360 |
| 3.8 | F | F | H | N | CH | 4-OPh | $MH^+$: 362.1 |
| 3.9 | F | F | H | N | CH | 4-tert-butyl | $MH^+$: 362.1 |
| 3.10 | F | F | H | N | CH | 2,6-$F_2$ | $MH^+$: 305.9 |
| 3.11 | F | F | H | N | CH | 2,4-$Cl_2$ | $MH^+$: 338 |
| 3.12 | F | F | H | N | CH | 4-(4-Cl—Ph) | 217–224 |
| 3.13 | F | F | H | N | CH | 4-(3-$CF_3$—Ph) | 193–194 |
| 3.14 | F | F | H | N | CH | 4-(2,4-$Cl_2$—Ph) | 214–215 |
| 3.15 | F | F | H | N | CH | 4-(4-$OCF_3$—Ph) | 225–230 |
| 3.16 | F | F | H | N | CH | 4-(4-$CF_3$—Ph) | 243–245 |
| 3.17 | F | F | H | N | CH | 4-Br | 180–181 |
| 3.18 | F | F | H | N | CH | 4-(4-F—Ph) | 195–197 |

TABLE 3-continued

Compounds of the formula

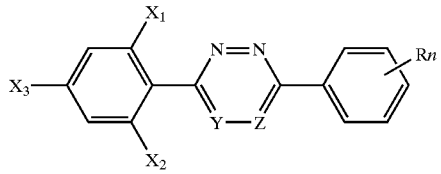

| No. | $X_1$ | $X_2$ | $X_3$ | Y | Z | $R_n$ | Phys. data[1] |
|---|---|---|---|---|---|---|---|
| 3.19 | F | F | H | N | CH | 4-(3-Cl-4-F—Ph) | 218–220 |
| 3.20 | F | F | H | N | CH | 4-(3,5-Cl$_2$—Ph) | 205–207 |
| 3.21 | F | F | H | N | CH | 4-(4-SCH$_3$—Ph) | 199–201 |
| 3.22 | F | F | H | N | CH | 4-(3-Cl—Ph) | 185–187 |
| 3.23 | F | F | H | N | CH | 4-(3-OCH$_3$—Ph) | 181–183 |
| 3.24 | F | F | H | N | CH | 4-(4-t-Bu—Ph) | 206–207 |
| 3.25 | F | F | H | N | CH | 4-(4-OCH$_3$—Ph) | 226–229 |
| 3.26 | F | F | H | N | CH | 4-(3,4-Cl$_2$—Ph) | 235–237 |
| 3.27 | F | F | H | N | CH | 4-(2-CF$_3$—Ph) | 151–153 |
| 3.28 | F | F | H | CH | N | 4-Br | 167–169 |
| 3.29 | F | F | H | CH | N | 4-(4-F—Ph) | 207–209 |
| 3.30 | F | F | H | CH | N | 4-(4-Cl—Ph) | 216–218 |
| 3.31 | F | F | H | CH | N | 4-(3-CF$_3$—Ph) | 194–195 |
| 3.32 | F | F | H | CH | N | 4-(4-CF$_3$—Ph) | 230–232 |
| 3.33 | F | F | H | CH | N | 4-(4-OCF$_3$—Ph) | 199–202 |
| 3.34 | F | F | H | CH | N | 4-(4-tert-butyl-Ph) | 187–189 |
| 3.35 | F | F | H | CH | N | 4-(2,4-Cl$_2$—Ph) | 267–269 |
| 3.36 | F | F | H | CH | N | 4-(3,5-Cl$_2$—Ph) | 213–214 |
| 3.37 | F | F | H | CH | N | 4-(2-CF$_3$—Ph) | 154–155 |
| 3.38 | F | F | H | CH | N | 4-(4-OCH$_3$—Ph) | 188–191 |
| 3.39 | F | F | H | CH | N | 4-(4-SCH$_3$—Ph) | 212–214 |
| 3.40 | F | F | H | CH | N | 4-(3-OCH$_3$—Ph) | 168–170 |
| 3.41 | F | F | H | CH | N | 4-(3-Cl—Ph) | 177–180 |
| 3.42 | F | F | H | CH | N | 4-(3,4-Cl$_2$—Ph) | 261–263 |
| 3.43 | F | F | H | CH | N | 4-(3-Cl-4-F—Ph) | 236–237 |
| 3.44 | Cl | H | Cl | CH | N | H | 163–165 |
| 3.45 | Cl | H | F | N | CH | 4-Br | 188–189 |
| 3.46 | Cl | H | F | N | CH | 4-(3-Cl-4-F—Ph) | 199–200 |
| 3.47 | Cl | H | F | N | CH | 4-(3-Cl—Ph) | 194–195 |
| 3.48 | F | F | H | N | CH | 4-(3-CF$_3$-Phenoxy) | 111–114 |
| 3.49 | F | F | H | N | CH | 4-Benzyloxy | 179–181 |
| 3.50 | F | F | H | N | CH | 4-CF$_3$ | 161–163 |
| 3.51 | F | F | H | N | CH | 4-([3-CH=NOMe]—Ph) | 200–201 |
| 3.52 | F | F | H | N | CH | 4-([3-CH=NOEt]—Ph) | 129–131 |
| 3.53 | F | F | H | N | CH | 4-([3-C{CH$_3$}=NOEt]—Ph) | 141–143 |
| 3.54 | Cl | H | H | N | CH | 4-(4-F—Ph) | |
| 3.55 | Cl | H | H | N | CH | 4-(4-Cl—Ph) | |
| 3.56 | Cl | H | H | N | CH | 4-(3-CF$_3$—Ph) | |
| 3.57 | Cl | H | H | N | CH | 4-(4-CF$_3$—Ph) | |
| 3.58 | Cl | H | H | N | CH | 4-(4-OCF$_3$—Ph) | |
| 3.59 | Cl | H | H | N | CH | 4-(4-t-Butyl-Ph) | |
| 3.60 | Cl | H | H | N | CH | 4-(2,4-Cl$_2$—Ph) | |
| 3.61 | Cl | H | H | N | CH | 4-(3,5-Cl$_2$—Ph) | |
| 3.62 | Cl | H | H | N | CH | 4-(2-CF$_3$—Ph) | |
| 3.63 | Cl | H | H | N | CH | 4-(4-OCH$_3$—Ph) | |
| 3.64 | Cl | H | H | N | CH | 4-(4-SCH$_3$—Ph) | |
| 3.65 | Cl | H | H | N | CH | 4-(3-OCH$_3$—Ph) | |
| 3.66 | Cl | H | H | N | CH | 4-(3-Cl—Ph) | |
| 3.67 | Cl | H | H | N | CH | 4-(3,4-Cl$_2$—Ph) | |
| 3.68 | Cl | H | H | N | CH | 4-(3-Cl-4-F—Ph) | |
| 3.69 | Cl | H | H | N | CH | 4-Br | |
| 3.70 | Cl | H | H | N | CH | 4-(4-CH$_3$—Ph) | |
| 3.71 | CH$_3$ | H | F | N | CH | 4-(4-F—Ph) | |
| 3.72 | CH$_3$ | H | F | N | CH | 4-(4-Cl—Ph) | |
| 3.73 | CH$_3$ | H | F | N | CH | 4-(3-CF$_3$—Ph) | |
| 3.74 | CH$_3$ | H | F | N | CH | 4-(4-CF$_3$—Ph) | |
| 3.75 | CH$_3$ | H | F | N | CH | 4-(4-OCF$_3$—Ph) | |
| 3.76 | CH$_3$ | H | F | N | CH | 4-(4-t-Butyl-Ph) | |
| 3.77 | CH$_3$ | H | F | N | CH | 4-(2,4-Cl$_2$—Ph) | |
| 3.78 | CH$_3$ | H | F | N | CH | 4-(3,5-Cl$_2$—Ph) | |
| 3.79 | CH$_3$ | H | F | N | CH | 4-(2-CF$_3$—Ph) | |
| 3.80 | CH$_3$ | H | F | N | CH | 4-(4-OCH$_3$—Ph) | |
| 3.81 | CH$_3$ | H | F | N | CH | 4-(4-SCH$_3$—Ph) | |
| 3.82 | CH$_3$ | H | F | N | CH | 4-(3-OCH$_3$—Ph) | |
| 3.83 | CH$_3$ | H | F | N | CH | 4-(3-Cl—Ph) | |

TABLE 3-continued

Compounds of the formula

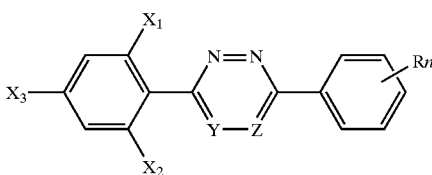

| No. | $X_1$ | $X_2$ | $X_3$ | Y | Z | $R_n$ | Phys. data[1]) |
|---|---|---|---|---|---|---|---|
| 3.84 | $CH_3$ | H | F | N | CH | 4-(3,4-$Cl_2$—Ph) | |
| 3.85 | $CH_3$ | H | F | N | CH | 4-(3-Cl-4-F—Ph) | |
| 3.86 | $CH_3$ | H | F | N | CH | 4-Br | |
| 3.87 | $CH_3$ | H | F | N | CH | 4-(4-$CH_3$—Ph) | |
| 3.88 | F | $CH_3$ | H | N | CH | 4-(4-F—Ph) | |
| 3.89 | F | $CH_3$ | H | N | CH | 4-(4-Cl—Ph) | |
| 3.90 | F | $CH_3$ | H | N | CH | 4-(3-$CF_3$—Ph) | |
| 3.91 | F | $CH_3$ | H | N | CH | 4-(4-$CF_3$—Ph) | |
| 3.92 | F | $CH_3$ | H | N | CH | 4-(4-$OCF_3$—Ph) | |
| 3.93 | F | $CH_3$ | H | N | CH | 4-(4-t-Butyl-Ph) | |
| 3.94 | F | $CH_3$ | H | N | CH | 4-(2,4-$Cl_2$—Ph) | |
| 3.95 | F | $CH_3$ | H | N | CH | 4-(3,5-$Cl_2$—Ph) | |
| 3.96 | F | $CH_3$ | H | N | CH | 4-(2-$CF_3$—Ph) | |
| 3.97 | F | $CH_3$ | H | N | CH | 4-(4-$OCH_3$—Ph) | |
| 3.98 | F | $CH_3$ | H | N | CH | 4-(4-$SCH_3$—Ph) | |
| 3.99 | F | $CH_3$ | H | N | CH | 4-(3-$OCH_3$—Ph) | |
| 3.100 | F | $CH_3$ | H | N | CH | 4-(3-Cl—Ph) | |
| 3.101 | F | $CH_3$ | H | N | CH | 4-(3,4-$Cl_2$—Ph) | |
| 3.102 | F | $CH_3$ | H | N | CH | 4-(3-Cl-4-F—Ph) | |
| 3.103 | F | $CH_3$ | H | N | CH | 4-Br | 173–174 |
| 3.104 | F | $CH_3$ | H | N | CH | 4-(4-$CH_3$—Ph) | |
| 3.105 | Cl | H | F | N | CH | 4-(4-F—Ph) | |
| 3.106 | Cl | H | F | N | CH | 4-(4-Cl—Ph) | |
| 3.107 | Cl | H | F | N | CH | 4-(3-$CF_3$—Ph) | 146–147 |
| 3.108 | Cl | H | F | N | CH | 4-(4-$CF_3$—Ph) | 195–196 |
| 3.109 | Cl | H | F | N | CH | 4-(4-$OCF_3$—Ph) | 198–200 |
| 3.110 | Cl | H | F | N | CH | 4-(4-t-Butyl-Ph) | |
| 3.111 | Cl | H | F | N | CH | 4-(2,4-$Cl_2$—Ph) | |
| 3.112 | Cl | H | F | N | CH | 4-(3,5-$Cl_2$—Ph) | 198–200 |
| 3.113 | Cl | H | F | N | CH | 4-(2-$CF_3$—Ph) | |
| 3.114 | Cl | H | F | N | CH | 4-(4-$OCH_3$—Ph) | |
| 3.115 | Cl | H | F | N | CH | 4-(4-$SCH_3$—Ph) | |
| 3.116 | Cl | H | F | N | CH | 4-(3-$OCH_3$—Ph) | |
| 3.117 | Cl | H | F | N | CH | 4-(3-Cl—Ph) | 194–195 |
| 3.118 | Cl | H | F | N | CH | 4-(3,4-$Cl_2$—Ph) | |
| 3.119 | Cl | H | F | N | CH | 4-(3-Cl-4-F—Ph) | 199–200 |
| 3.120 | Cl | H | F | N | CH | 4-Br | |
| 3.121 | Cl | H | F | N | CH | 4-(4-$CH_3$—Ph) | |
| 3.122 | F | H | Cl | N | CH | 4-(4-F—Ph) | |
| 3.123 | F | H | Cl | N | CH | 4-(4-Cl—Ph) | |
| 3.124 | F | H | Cl | N | CH | 4-(3-$CF_3$—Ph) | |
| 3.125 | F | H | Cl | N | CH | 4-(4-$CF_3$—Ph) | |
| 3.126 | F | H | Cl | N | CH | 4-(4-$OCF_3$—Ph) | |
| 3.127 | F | H | Cl | N | CH | 4-(4-t-Butyl-Ph) | |
| 3.128 | F | H | Cl | N | CH | 4-(2,4-$Cl_2$—Ph) | |
| 3.129 | F | H | Cl | N | CH | 4-(3,5-$Cl_2$—Ph) | |
| 3.130 | F | H | Cl | N | CH | 4-(2-$CF_3$—Ph) | |
| 3.131 | F | H | Cl | N | CH | 4-(4-$OCH_3$—Ph) | |
| 3.132 | F | H | Cl | N | CH | 4-(4-$SCH_3$—Ph) | |
| 3.133 | F | H | Cl | N | CH | 4-(3-$OCH_3$—Ph) | |
| 3.134 | F | H | Cl | N | CH | 4-(3-Cl—Ph) | |
| 3.135 | F | H | Cl | N | CH | 4-(3,4-$Cl_2$—Ph) | |
| 3.136 | F | H | Cl | N | CH | 4-(3-Cl-4-F—Ph) | |
| 3.137 | F | H | Cl | N | CH | 4-Br | |
| 3.138 | F | H | Cl | N | CH | 4-(4-$CH_3$—Ph) | |
| 3.139 | OMe | OMe | H | N | CH | 4-(4-F—Ph) | |
| 3.140 | OMe | OMe | H | N | CH | 4-(4-Cl—Ph) | |
| 3.141 | OMe | OMe | H | N | CH | 4-(3-$CF_3$—Ph) | |
| 3.142 | OMe | OMe | H | N | CH | 4-(4-$CF_3$—Ph) | |
| 3.143 | OMe | OMe | H | N | CH | 4-(4-$OCF_3$—Ph) | |
| 3.144 | OMe | OMe | H | N | CH | 4-(4-t-Butyl-Ph) | |
| 3.145 | OMe | OMe | H | N | CH | 4-(2,4-$Cl_2$—Ph) | |
| 3.146 | OMe | OMe | H | N | CH | 4-(3,5-$Cl_2$—Ph) | |
| 3.147 | OMe | OMe | H | N | CH | 4-(2-$CF_3$—Ph) | |
| 3.148 | OMe | OMe | H | N | CH | 4-(4-$OCH_3$—Ph) | |

TABLE 3-continued

Compounds of the formula

| No. | X₁ | X₂ | X₃ | Y | Z | Rₙ | Phys. data¹⁾ |
|---|---|---|---|---|---|---|---|
| 3.149 | OMe | OMe | H | N | CH | 4-(4-SCH₃—Ph) | |
| 3.150 | OMe | OMe | H | N | CH | 4-(3-OCH₃—Ph) | |
| 3.151 | OMe | OMe | H | N | CH | 4-(3-Cl—Ph) | |
| 3.152 | OMe | OMe | H | N | CH | 4-(3,4-Cl₂—Ph) | |
| 3.153 | OMe | OMe | H | N | CH | 4-(3-Cl-4-F—Ph) | |
| 3.154 | OMe | OMe | H | N | CH | 4-Br | |
| 3.155 | OMe | OMe | H | N | CH | 4-(4-CH₃—Ph) | |
| 3.156 | F | F | OMe | N | CH | 4-(4-F—Ph) | |
| 3.157 | F | F | OMe | N | CH | 4-(4-Cl—Ph) | |
| 3.158 | F | F | OMe | N | CH | 4-(3-CF₃—Ph) | |
| 3.159 | F | F | OMe | N | CH | 4-(4-CF₃—Ph) | |
| 3.160 | F | F | OMe | N | CH | 4-(4-OCF₃—Ph) | |
| 3.161 | F | F | OMe | N | CH | 4-(4-t-Butyl-Ph) | |
| 3.162 | F | F | OMe | N | CH | 4-(2,4-Cl₂—Ph) | |
| 3.163 | F | F | OMe | N | CH | 4-(3,5-Cl₂—Ph) | |
| 3.164 | F | F | OMe | N | CH | 4-(2-CF₃—Ph) | |
| 3.165 | F | F | OMe | N | CH | 4-(4-OCH₃—Ph) | |
| 3.166 | F | F | OMe | N | CH | 4-(4-SCH₃—Ph) | |
| 3.167 | F | F | OMe | N | CH | 4-(3-OCH₃—Ph) | |
| 3.168 | F | F | OMe | N | CH | 4-(3-Cl—Ph) | |
| 3.169 | F | F | OMe | N | CH | 4-(3,4-Cl₂—Ph) | |
| 3.170 | F | F | OMe | N | CH | 4-(3-Cl-4-F—Ph) | |
| 3.171 | F | F | OMe | N | CH | 4-Br | |
| 3.172 | F | F | OMe | N | CH | 4-(4-CH₃—Ph) | |
| 3.173 | F | CF₃ | H | N | CH | 4-(4-F—Ph) | |
| 3.174 | F | CF₃ | H | N | CH | 4-(4-Cl—Ph) | |
| 3.175 | F | CF₃ | H | N | CH | 4-(3-CF₃—Ph) | |
| 3.176 | F | CF₃ | H | N | CH | 4-(4-CF₃—Ph) | |
| 3.177 | F | CF₃ | H | N | CH | 4-(4-OCF₃—Ph) | |
| 3.178 | F | CF₃ | H | N | CH | 4-(4-t-Butyl-Ph) | |
| 3.179 | F | CF₃ | H | N | CH | 4-(2,4-Cl₂—Ph) | |
| 3.180 | F | CF₃ | H | N | CH | 4-(3,5-Cl₂—Ph) | |
| 3.181 | F | CF₃ | H | N | CH | 4-(2-CF₃—Ph) | |
| 3.182 | F | CF₃ | H | N | CH | 4-(4-OCH₃—Ph) | |
| 3.183 | F | CF₃ | H | N | CH | 4-(4-SCH₃—Ph) | |
| 3.184 | F | CF₃ | H | N | CH | 4-(3-OCH₃—Ph) | |
| 3.185 | F | CF₃ | H | N | CH | 4-(3-Cl—Ph) | |
| 3.186 | F | CF₃ | H | N | CH | 4-(3,4-Cl₂—Ph) | |
| 3.187 | F | CF₃ | H | N | CH | 4-(3-Cl-4-F—Ph) | |
| 3.188 | F | CF₃ | H | N | CH | 4-Br | |
| 3.189 | F | CF₃ | H | N | CH | 4-(4-CH₃—Ph) | |
| 3.190 | SMe | H | H | N | CH | 4-(4-F—Ph) | |
| 3.191 | SMe | H | H | N | CH | 4-(4-Cl—Ph) | |
| 3.192 | SMe | H | H | N | CH | 4-(3-CF₃—Ph) | |
| 3.193 | SMe | H | H | N | CH | 4-(4-CF₃—Ph) | |
| 3.194 | SMe | H | H | N | CH | 4-(4-OCF₃—Ph) | |
| 3.195 | SMe | H | H | N | CH | 4-(4-t-Butyl-Ph) | |
| 3.196 | SMe | H | H | N | CH | 4-(2,4-Cl₂—Ph) | |
| 3.197 | SMe | H | H | N | CH | 4-(3,5-Cl₂—Ph) | |
| 3.198 | SMe | H | H | N | CH | 4-(2-CF₃—Ph) | |
| 3.199 | SMe | H | H | N | CH | 4-(4-OCH₃—Ph) | |
| 3.200 | SMe | H | H | N | CH | 4-(4-SCH₃—Ph) | |
| 3.201 | SMe | H | H | N | CH | 4-(3-OCH₃—Ph) | |
| 3.202 | SMe | H | H | N | CH | 4-(3-Cl—Ph) | |
| 3.203 | SMe | H | H | N | CH | 4-(3,4-Cl₂—Ph) | |
| 3.204 | SMe | H | H | N | CH | 4-(3-Cl-4-F—Ph) | |
| 3.205 | SMe | H | H | N | CH | 4-Br | |
| 3.206 | SMe | H | H | N | CH | 4-(4-CH₃—Ph) | |
| 3.207 | Cl | H | F | N | CH | 4-(4-SCF₃—Ph) | |
| 3.208 | Cl | H | F | N | CH | 4-(4-SOCF₃—Ph) | |
| 3.209 | Cl | H | F | N | CH | 4-(4-SO₂CF₃—Ph) | |

TABLE 3-continued

Compounds of the formula

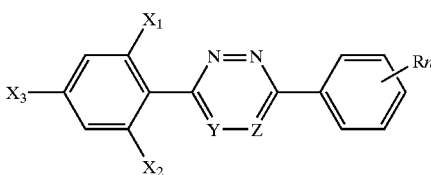

| No. | $X_1$ | $X_2$ | $X_3$ | Y | Z | $R_n$ | Phys. data[1] |
|---|---|---|---|---|---|---|---|
| 3.210 | Cl | H | F | N | CCH$_3$ | 4-(4-CF$_3$—Ph) | |
| 3.211 | Cl | H | F | N | CCH$_3$ | 4-(4-OCF$_3$—Ph) | |
| 3.212 | Cl | H | F | N | CCH$_3$ | 4-(2,5-Cl$_2$—Ph) | |
| 3.213 | Cl | H | F | N | CCH$_3$ | 4-(3-Cl, 4-F—Ph) | |
| 3.214 | Cl | H | F | N | CCH$_3$ | 4-(4-SCF$_3$—Ph) | |
| 3.215 | F | F | H | N | CH | 4-(4-CF$_3$-Benzyloxy) | 173–175 |
| 3.216 | F | F | H | N | CH | 4-(3-CF$_3$-Benzyloxy) | 151–153 |

[1]MH$^+$: Molecular peak from LC-MS measurements; other figures: melting point

TABLE 4

Compounds of the formula

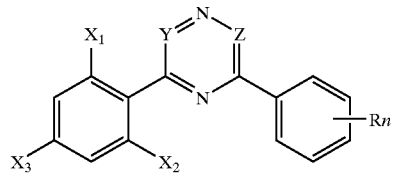

| No. | $X_1$ | $X_2$ | $X_3$ | Y | Z | $R_n$ | Phys. data[1] |
|---|---|---|---|---|---|---|---|
| 4.1 | Cl | H | Cl | N | CH | 4-OPh | MH$^+$: 394 |
| 4.2 | Cl | H | Cl | N | CH | 4-CF$_3$ | MH$^+$: 369.9 |
| 4.3 | Cl | H | Cl | N | CH | 4-(3-CF$_3$—Ph) | MH$^+$: 446 |
| 4.4 | Cl | H | Cl | N | CH | 4-(4-CF$_3$—Ph) | MH$^+$: 446 |
| 4.5 | Cl | H | Cl | N | CH | 4-(2,4-Cl$_2$—Ph) | MH$^+$: 446 |
| 4.6 | Cl | H | Cl | N | CH | 2,4-Cl$_2$ | MH$^+$: 369.9 |
| 4.7 | Cl | H | Cl | N | CH | 4-(4-Cl—Ph) | MH$^+$: 411.9 |
| 4.8 | Cl | H | Cl | N | CH | 4-tert-butyl | MH$^+$: 357.9 |
| 4.9 | Cl | H | Cl | N | CH | 4-(4-CH$_3$—Ph) | MH$^+$: 392 |
| 4.10 | Cl | H | Cl | N | CH | 2,6-F$_2$ | MH$^+$: 337.9 |
| 4.11 | F | F | H | N | CH | 4-CF$_3$ | MH$^+$: 337.9 |
| 4.12 | F | F | H | N | CH | 4-(4-CH$_3$—Ph) | MH$^+$: 360 |
| 4.13 | F | F | H | N | CH | 4-(4-Cl—Ph) | MH$^+$: 380 |
| 4.14 | F | F | H | N | CH | 4-(3-CF$_3$—Ph) | MH$^+$: 414.1 |
| 4.15 | F | F | H | N | CH | 4-(4-CF$_3$—Ph) | MH$^+$: 414.1 |
| 4.16 | F | F | H | N | CH | 4-OPh | MH$^+$: 362 |
| 4.17 | F | F | H | N | CH | 4-tert-butyl | MH$^+$: 326.1 |
| 4.18 | F | F | H | N | CH | 4-(2,4-Cl$_2$—Ph) | MH$^+$: 413.9 |
| 4.19 | F | F | H | N | CH | 2,6-F$_2$ | MH$^+$: 306 |
| 4.20 | F | F | H | N | CH | 2,4-Cl$_2$ | MH$^+$: 337.9 |
| 4.21 | F | F | H | N | CH | 4-Br | 179–180 |
| 4.22 | F | F | H | N | CH | 4-(4-F—Ph) | 172–173 |
| 4.23 | F | F | H | N | CH | 4-(4-OCH$_3$—Ph) | 139–140 |
| 4.24 | F | F | H | N | CH | 4-(4-t-Bu—Ph) | 210–211 |
| 4.25 | F | F | H | N | CH | 4-(3-OCH$_3$—Ph) | 193–194 |
| 4.26 | F | F | H | N | CH | 4-(2-CF$_3$—Ph) | 193–194 |
| 4.27 | F | F | H | N | CH | 4-(3-Cl-4-F—Ph) | 187–188 |
| 4.28 | F | F | H | N | CH | 4-(3-Cl—Ph) | 213–215 |
| 4.29 | F | F | H | N | CH | 4-(3,5-Cl$_2$Ph) | 197–199 |
| 4.30 | F | F | H | CH | N | 4-(4-Cl—Ph) | 189–190 |
| 4.31 | F | F | H | CH | N | 4-(3-CF$_3$—Ph) | 155–156 |
| 4.32 | F | F | H | CH | N | 4-(4-CF$_3$—Ph) | 193–194 |
| 4.33 | F | F | H | CH | N | 4-OCF$_3$ | 159–160 |
| 4.34 | F | F | H | CH | N | 4-(3,4-Cl$_2$—Ph) | 208–209 |
| 4.35 | F | F | H | CH | N | 4-(3-Cl-4-F—Ph) | 203–204 |
| 4.36 | F | F | H | CH | N | 4-Br | |
| 4.37 | Cl | H | F | N | CH | 4-Br | solid |
| 4.38 | Cl | H | F | N | CH | 4-(4-CF$_3$—Ph) | 126–127 |

TABLE 4-continued

Compounds of the formula

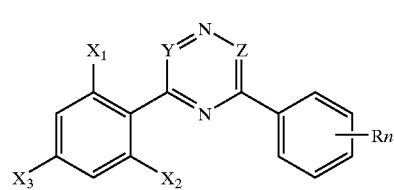

| No. | $X_1$ | $X_2$ | $X_3$ | Y | Z | $R_n$ | Phys. data[1] |
|---|---|---|---|---|---|---|---|
| 4.39 | Cl | H | F | N | CH | 4-(4-OCF$_3$—Ph) | 107–108 |
| 4.40 | Cl | H | F | N | CH | 4-(3,5-Cl$_2$—Ph) | 196–198 |
| 4.41 | F | F | H | N | CH | 4-(4-OCF$_3$—Ph) | Harz |
| 4.42 | F | F | H | N | CH | 4-(Cl-Phenoxy) | Harz |

[1]MH$^+$: Molecular peak from LC-MS measurements; other figures: melting point

TABLE 5

Compounds of the formula

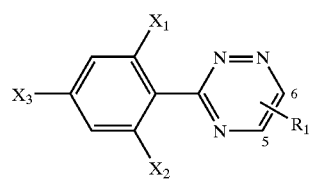

| No. | $X_1$ | $X_2$ | $X_3$ | $R_1$ | Phys. data |
|---|---|---|---|---|---|
| 5.1 | Cl | H | Cl | 5-(4-phenylthiazol-2-yl) | |
| 5.2 | Cl | H | Cl | 6-(benzofuran-5-yl) | |
| 5.3 | Cl | H | Cl | 5-(thiazol-2-yl) | |
| 5.4 | Cl | H | Cl | 6-(benzothiazol-2-yl) | |
| 5.5 | F | F | H | 5-(thiazol-2-yl) | |
| 5.6 | F | F | H | 6-(4-phenylthiazol-2-yl) | |
| 5.7 | Cl | H | Cl | 6-(4-phenylthiazol-2-yl) | |
| 5.8 | F | F | H | 5-(indol-3-yl) | |
| 5.9 | Cl | H | Cl | 5-(indol-3-yl) | |
| 5.10 | Cl | H | Cl | 6-(indol-3-yl) | |
| 5.11 | F | F | H | 6-(5-Br-thiophen-2-yl) | 196–197 |

TABLE 5-continued

Compounds of the formula

| No. | $X_1$ | $X_2$ | $X_3$ | $R_1$ | Phys. data |
|---|---|---|---|---|---|
| 5.12 | F | F | H | 6-(5-phenylthiophen-2-yl) | |
| 5.13 | F | F | H | 6-(furan-2-yl) | 131–132 |
| 5.14 | F | F | H | 6-(naphth-2-yl) | 160–162 |

TABLE A (Ia)

| No. | $X_1$ | $X_2$ | $X_3$ | A |
|---|---|---|---|---|
| A.1 | F | F | F | —C≡C— |
| A.2 | F | F | Cl | —C≡C— |
| A.3 | F | F | H | —C≡C— |
| A.4 | F | Cl | F | —C≡C— |
| A.5 | F | Cl | Cl | —C≡C— |
| A.6 | F | Cl | H | —C≡C— |
| A.7 | Cl | Cl | F | —C≡C— |
| A.8 | Cl | Cl | Cl | —C≡C— |
| A.9 | Cl | Cl | H | —C≡C— |
| A.10 | Cl | H | F | —C≡C— |
| A.11 | F | H | H | —C≡C— |
| A.12 | Cl | H | H | —C≡C— |
| A.13 | F | F | F | —HC=CH— |
| A.14 | F | F | Cl | —HC=CH— |
| A.15 | F | F | H | —HC=CH— |
| A.16 | F | Cl | F | —HC=CH— |
| A.17 | F | Cl | Cl | —HC=CH— |
| A.18 | F | Cl | H | —HC=CH— |
| A.19 | Cl | Cl | F | —HC=CH— |
| A.20 | Cl | Cl | Cl | —HC=CH— |
| A.21 | Cl | Cl | H | —HC=CH— |
| A.22 | Cl | H | F | —HC=CH— |
| A.23 | F | H | H | —HC=CH— |
| A.24 | Cl | H | H | —HC=CH— |
| A.25 | F | F | F | O |
| A.26 | F | F | Cl | O |
| A.27 | F | F | H | O |
| A.28 | F | Cl | F | O |
| A.29 | F | Cl | Cl | O |
| A.30 | F | Cl | H | O |
| A.31 | Cl | Cl | F | O |
| A.32 | Cl | Cl | Cl | O |
| A.33 | Cl | Cl | H | O |
| A.34 | Cl | H | F | O |
| A.35 | F | H | H | O |
| A.36 | Cl | H | H | O |
| A.37 | F | F | F | NH |
| A.38 | F | F | Cl | NH |
| A.39 | F | F | H | NH |
| A.40 | F | Cl | F | NH |
| A.41 | F | Cl | Cl | NH |
| A.42 | F | Cl | H | NH |
| A.43 | Cl | Cl | F | NH |
| A.44 | Cl | Cl | Cl | NH |
| A.45 | Cl | Cl | H | NH |

TABLE A-continued (Ia)

| No. | $X_1$ | $X_2$ | $X_3$ | A |
|---|---|---|---|---|
| A.46 | Cl | H | F | NH |
| A.47 | F | H | H | NH |
| A.48 | Cl | H | H | NH |
| A.49 | F | F | F | N(CH$_3$) |
| A.50 | F | F | Cl | N(CH$_3$) |
| A.51 | F | F | H | N(CH$_3$) |
| A.52 | F | Cl | F | N(CH$_3$) |
| A.53 | F | Cl | Cl | N(CH$_3$) |
| A.54 | F | Cl | H | N(CH$_3$) |
| A.55 | Cl | Cl | F | N(CH$_3$) |
| A.56 | Cl | Cl | Cl | N(CH$_3$) |
| A.57 | Cl | Cl | H | N(CH$_3$) |
| A.58 | Cl | H | F | N(CH$_3$) |
| A.59 | F | H | H | N(CH$_3$) |
| A.60 | Cl | H | H | N(CH$_3$) |
| A.61 | F | F | F | *NH(CH$_2$) |
| A.62 | F | F | Cl | *NH(CH$_2$) |
| A.63 | F | F | H | *NH(CH$_2$) |
| A.64 | F | Cl | F | *NH(CH$_2$) |
| A.65 | F | Cl | Cl | *NH(CH$_2$) |
| A.66 | F | Cl | H | *NH(CH$_2$) |
| A.67 | Cl | Cl | F | *NH(CH$_2$) |
| A.68 | Cl | Cl | Cl | *NH(CH$_2$) |
| A.69 | Cl | Cl | H | *NH(CH$_2$) |
| A.70 | Cl | H | F | *NH(CH$_2$) |
| A.71 | F | H | H | *NH(CH$_2$) |
| A.72 | Cl | H | H | *NH(CH$_2$) |
| A.73 | F | F | F | S |
| A.74 | F | F | Cl | S |
| A.75 | F | F | H | S |
| A.76 | F | Cl | F | S |
| A.77 | F | Cl | Cl | S |
| A.78 | F | Cl | H | S |
| A.79 | Cl | Cl | F | S |
| A.80 | Cl | Cl | Cl | S |
| A.81 | Cl | Cl | H | S |
| A.82 | Cl | H | F | S |
| A.83 | F | H | H | S |
| A.84 | Cl | H | H | S |
| A.85 | F | F | F | SO |
| A.86 | F | F | Cl | SO |
| A.87 | F | F | H | SO |
| A.88 | F | Cl | F | SO |
| A.89 | F | Cl | Cl | SO |
| A.90 | F | Cl | H | SO |
| A.91 | Cl | Cl | F | SO |
| A.92 | Cl | Cl | Cl | SO |
| A.93 | Cl | Cl | H | SO |
| A.94 | Cl | H | F | SO |
| A.95 | F | H | H | SO |
| A.96 | Cl | H | H | SO |
| A.97 | F | F | F | SO$_2$ |
| A.98 | F | F | Cl | SO$_2$ |
| A.99 | F | F | H | SO$_2$ |
| A.100 | F | Cl | F | SO$_2$ |
| A.101 | F | Cl | Cl | SO$_2$ |
| A.102 | F | Cl | H | SO$_2$ |
| A.103 | Cl | Cl | F | SO$_2$ |
| A.104 | Cl | Cl | Cl | SO$_2$ |
| A.105 | Cl | Cl | H | SO$_2$ |
| A.106 | Cl | H | F | SO$_2$ |
| A.107 | F | H | H | SO$_2$ |
| A.108 | Cl | H | H | SO$_2$ |

*N bonded to triazine ring

Table 6.1: Compounds of the general formula (Ia), in which R is 4-Cl and the combination of substituents $X_1$, $X_2$, $X_3$ and A for a compound in each case corresponds to a line A.1 to A.108 in table A.

Table 6.2: Compounds of the general formula (Ia), in which R is 4-F and the combination of substituents $X_1$, $X_2$, $X_3$ and A for a compound in each case corresponds to a line A.1 to A.108 in table A.

Table 6.3: Compounds of the general formula (Ia), in which R is 4—$CH_3$ and the combination of substituents $X_1$, $X_2$, $X_3$ and A for a compound in each case corresponds to a line A.1 to A.108 in table A.

Table 6.4: Compounds of the general formula (Ia), in which R is 4-$CF_3$ and the combination of substituents $X_1$, $X_2$, $X_3$ and A for a compound in each case corresponds to a line A.1 to A.108 in table A.

Table 6.5: Compounds of the general formula (Ia), in which R is 3-$CF_3$ and the combination of substituents $X_1$, $X_2$, $X_3$ and A for a compound in each case corresponds to a line A.1 to A.108 in table A.

Table 6.6: Compounds of the general formula (Ia), in which R is 4-$OCF_3$ and the combination of substituents $X_1$, $X_2$, $X_3$ and A for a compound in each case corresponds to a line A.1 to A.108 in table A.

Table 6.7: Compounds of the general formula (Ia), in which R is 2-Cl and the combination of substituents $X_1$, $X_2$, $X_3$ and A for a compound in each case corresponds to a line A.1 to A.108 in table A.

Table 6.8: Compounds of the general formula (Ia), in which R is 3-Cl and the combination of substituents $X_1$, $X_2$, $X_3$ and A for a compound in each case corresponds to a line A.1 to A.108 in table A.

Table 6.9: Compounds of the general formula (Ia), in which R is 2-F and the combination of substituents $X_1$, $X_2$, $X_3$ and A for a compound in each case corresponds to a line A.1 to A.108 in table A.

Table 6.10: Compounds of the general formula (Ia), in which R is H and the combination of substituents $X_1$, $X_2$, $X_3$ and A for a compound in each case corresponds to a line A.1 to A.108 in table A.

Table 6.11: Compounds of the general formula (Ia), in which R is 4-$OCH_3$ and the combination of substituents $X_1$, $X_2$, $X_3$ and A for a compound in each case corresponds to a line A.1 to A.108 in table A.

Table 6.12: Compounds of the general formula (Ia), in which R is 2,4-$Cl_2$ and the combination of substituents $X_1$, $X_2$, $X_3$ and A for a compound in each case corresponds to a line A.1 to A.108 in table A.

Table 6.13: Compounds of the general formula (Ia), in which R is 3,5-$C_{12}$ and the combination of substituents $X_1$, $X_2$, $X_3$ and A for a compound in each case corresponds to a line A.1 to A.108 in table A.

Table 6.14: Compounds of the general formula (Ia), in which R is 4-$SCH_3$ and the combination of substituents $X_1$, $X_2$, $X_3$ and A for a compound in each case corresponds to a line A.1 to A.108 in table A.

Table 6.15: Compounds of the general formula (Ia), in which R is 4-$SCF_3$ and the combination of substituents $X_1$, $X_2$, $X_3$ and A for a compound in each case corresponds to a line A.1 to A.108 in table A.

Table 6.16: Compounds of the general formula (Ia), in which R is 3-Cl, 4-F and the combination of substituents $X_1$, $X_2$, $X_3$ and A for a compound in each case corresponds to a line A.1 to A.108 in table A.

Table 6.17: Compounds of the general formula (Ia), in which R is 4-t-But and the combination of substituents $X_1$, $X_2$, $X_3$ and A for a compound in each case corresponds to a line A.1 to A.108 in table A.

Table 6.18: Compounds of the general formula (Ia), in which R is 3,4-$Cl_2$ and the combination of substituents $X_1$, $X_2$, $X_3$ and A for a compound in each case corresponds to a line A.1 to A.108 in table A.

Table 6.19: Compounds of the general formula (Ia), in which R is 4-Br and the combination of substituents $X_1$, $X_2$, $X_3$ and A for a compound in each case corresponds to a line A.1 to A.108 in table A.

Table 6.20: Compounds of the general formula (Ia), in which R is 4-$O(CH_2)_5CH_3$ and the combination of substituents $X_1$, $X_2$, $X_3$ and A for a compound in each case corresponds to a line A.1 to A.108 in table A.

Table 6.21: Compounds of the general formula (Ia), in which R is 4-$O(CH_2)_2CH_3$ and the combination of substituents $X_1$, $X_2$, $X_3$ and A for a compound in each case corresponds to a line A.1 to A.108 in table A.

Table 6.22: Compounds of the general formula (Ia), in which R is 4-$O(CH_2)_3CH_3$ and the combination of substituents $X_1$, $X_2$, $X_3$ and A for a compound in each case corresponds to a line A.1 to A.108 in table A.

Table 6.23: Compounds of the general formula (Ia), in which R is 4-$CH_2CH_3$ and the combination of substituents $X_1$, $X_2$, $X_3$ and A for a compound in each case corresponds to a line A.1 to A.108 in table A.

Table 6.24: Compounds of the general formula (Ia), in which R is 4-$(CH_2)_5CH_3$ and the combination of substituents $X_1$, $X_2$, $X_3$ and A for a compound in each case corresponds to a line A.1 to A.108 in table A.

Table 6.25: Compounds of the general formula (Ia), in which R is 4-[4-fluorophenyl] and the combination of substituents $X_1$, $X_2$, $X_3$ and A for a compound in each case corresponds to a line A.1 to A.108 in table A.

Table 6.25: Compounds of the general formula (Ia), in which R is 4-[4-chlorophenyl] and the combination of substituents $X_1$, $X_2$, $X_3$ and A for a compound in each case corresponds to a line A.1 to A.108 in table A.

Table 6.27: Compounds of the general formula (Ia), in which R is 4-$(CH_2)_2CH_3$ and the combination of substituents $X_1$, $X_2$, $X_3$ and A for a compound in each case corresponds to a line A.1 to A.108 in table A.

Table 6.28: Compounds of the general formula (Ia), in which R is 4-[4-methylphenyl] and the combination of substituents $X_1$, $X_2$, $X_3$ and A for a compound in each case corresponds to a line A.1 to A.108 in table A.

Table 6.29: Compounds of the general formula (Ia), in which R is 4-[4-$OCF_3$-phenyl] and the combination of substituents $X_1$, $X_2$, $X_3$ and A for a compound in each case corresponds to a line A.1 to A.108 in table A.

Table 6.30: Compounds of the general formula (Ia), in which R is 4-[4-$OCF_3$-phenoxy] and the combination of substituents $X_1$, $X_2$, $X_3$ and A for a compound in each case corresponds to a line A.1 to A.108 in table A.

Table 6.31: Compounds of the general formula (Ia), in which R is 4-[4-$CF_3$-phenyl] and the combination of substituents $X_1$, $X_2$, $X_3$ and A for a compound in each case corresponds to a line A.1 to A.108 in table A.

Table 6.32: Compounds of the general formula (Ia), in which R is 4-[4-$CF_3$-phenoxy] and the combination of substituents $X_1$, $X_2$, $X_3$ and A for a compound in each case corresponds to a line A.1 to A.108 in table A.

Table 6.33: Compounds of the general formula (Ia), in which R is 4-[2-Cl-4-$CF_3$-phenoxy] and the combination of substituents $X_1$, $X_2$, $X_3$ and A for a compound in each case corresponds to a line A.1 to A.108 in table A.

Table 6.34: Compounds of the general formula (Ia), in which R is 4-[4-chlorophenoxy] and the combination of substituents $X_1$, $X_2$, $X_3$ and A for a compound in each case corresponds to a line A.1 to A.108 in table A.

TABLE 6.35

Compounds of the formula

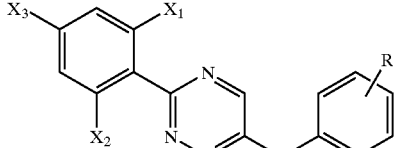

| X₁ | X₂ | X₃ | R | A | m.p. (° C.) |
|---|---|---|---|---|---|
| F | F | H | 4-Cl | CH=CH | 135–140 |
| F | F | H | 3-Cl | CH=CH | 86–89 |
| F | F | H | 3,4-Cl₂ | CH=CH | 94–97 |
| F | F | H | 4-CF₃ | CH=CH | 112–115 |
| F | F | H | 3-CF₃ | CH=CH | Harz |
| F | F | H | 3-Cl | O | 132–137 |
| F | F | H | 4-Br | O | 147–150 |
| F | F | H | 4-OCF₃ | O | resin |
| F | F | H | 4-[4-CF₃-phenoxy] | O | 169–170 |
| F | F | H | 4-[2-Cl-4-CF₃-phenoxy] | O | resin |
| F | F | H | 4-Cl | *NHCH₂ | 200–205 |
| F | F | H | 4-tert-butyl | O | 142–146 |

*N bonded to triazine ring

TABLE 7

Compounds of the formula

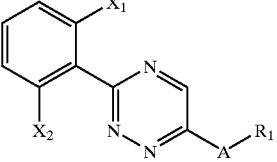

| No. | X₁ | X₂ | R₁ | A | Phys. data |
|---|---|---|---|---|---|
| 7.1 | F | F | benzothiazol-2-yl | — | solid |
| 7.2 | F | F | 5-Cl-benzothiazol-2-yl | — | |
| 7.3 | F | F | 5-CF₃-benzothiazol-2-yl | — | |
| 7.4 | F | F | 5-OCF₃-benzothiazol-2-yl | — | |
| 7.5 | F | F | 5-F-benzothiazol-2-yl | — | |
| 7.6 | F | F | benzothiazol-2-yl | —C≡C— | |
| 7.7 | F | F | 5-Cl-benzothiazol-2-yl | —C≡C— | |
| 7.8 | F | F | 5-CF₃-benzothiazol-2-yl | —C≡C— | |
| 7.9 | F | F | 5-OCF₃-benzothiazol-2-yl | —C≡C— | |
| 7.10 | F | F | 5-F-benzothiazol-2-yl | —C≡C— | |
| 7.11 | F | F | 5-Bromo-thien-2-yl | — | 195–197 |

TABLE 8

Compounds of the formula

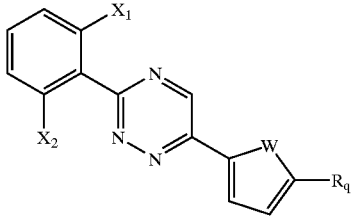

| No. | X₁ | X₂ | W | R_q | Phys. data |
|---|---|---|---|---|---|
| 8.1 | F | F | O | 4-F—Ph | |
| 8.2 | F | F | O | 4-Cl—Ph | |
| 8.3 | F | F | O | 3-CF₃—Ph | |
| 8.4 | F | F | O | 4-CF₃—Ph | |
| 8.5 | F | F | O | 4-OCF₃—Ph | |
| 8.6 | F | F | O | 4-t-Butyl-Ph | |
| 8.7 | F | F | O | 2,4-Cl₂—Ph | |
| 8.8 | F | F | O | 3,5-Cl₂—Ph | |
| 8.9 | F | F | O | 2-CF₃—Ph | |
| 8.10 | F | F | O | 4-OCH₃—Ph | |
| 8.11 | F | F | O | 4-SCH₃—Ph | |
| 8.12 | F | F | O | 3-OCH₃—Ph | |
| 8.13 | F | F | O | 3-Cl—Ph | |
| 8.14 | F | F | O | 3,4-Cl₂—Ph | |
| 8.15 | F | F | O | 3-Cl-4-F—Ph | |
| 8.16 | F | F | O | 4-SCF₃—PH | |
| 8.17 | F | F | O | 4-SOCF₃—Ph | |
| 8.18 | F | F | O | 4-SO₂CF₃—Ph | |
| 8.19 | F | F | S | 4-F—Ph | |
| 8.20 | F | F | S | 4-Cl—Ph | |
| 8.21 | F | F | S | 3-CF₃—Ph | |
| 8.22 | F | F | S | 4-CF₃—Ph | 214–216 |
| 8.23 | F | F | S | 4-OCF₃—Ph | 197–198 |
| 8.24 | F | F | S | 4-t-Butyl-Ph | |
| 8.25 | F | F | S | 2,4-Cl₂—Ph | |
| 8.26 | F | F | S | 3,5-Cl₂—Ph | |
| 8.27 | F | F | S | 2-CF₃—Ph | |
| 8.28 | F | F | S | 4-OCH₃—Ph | |
| 8.29 | F | F | S | 4-SCH₃—Ph | |
| 8.30 | F | F | S | 3-OCH₃—Ph | |
| 8.31 | F | F | S | 3-Cl—Ph | |
| 8.32 | F | F | S | 3,4-Cl₂—Ph | |
| 8.33 | F | F | S | 3-Cl-4-F—Ph | |
| 8.34 | F | F | S | 4-SCF₃—PH | |
| 8.35 | F | F | S | 4-SOCF₃—Ph | |
| 8.36 | F | F | S | 4-SO₂CF₃—Ph | |
| 8.37 | F | F | NH | 4-F—Ph | |
| 8.38 | F | F | NH | 4-Cl—Ph | |
| 8.39 | F | F | NH | 3-CF₃—Ph | |
| 8.40 | F | F | NH | 4-CF₃—Ph | |
| 8.41 | F | F | NH | 4-OCF₃—Ph | |
| 8.42 | F | F | NH | 4-t-Butyl-Ph | |
| 8.43 | F | F | NH | 2,4-Cl₂—Ph | |
| 8.44 | F | F | NH | 3,5-Cl₂—Ph | |
| 8.45 | F | F | NH | 2-CF₃—Ph | |
| 8.46 | F | F | NH | 4-OCH₃—Ph | |
| 8.47 | F | F | NH | 4-SCH₃—Ph | |
| 8.48 | F | F | NH | 3-OCH₃—Ph | |
| 8.49 | F | F | NH | 3-Cl—Ph | |
| 8.50 | F | F | NH | 3,4-Cl₂—Ph | |
| 8.51 | F | F | NH | 3-Cl-4-F—Ph | |
| 8.52 | F | F | NH | 4-SCF₃—Ph | |
| 8.53 | F | F | NH | 4-SOCF₃—Ph | |
| 8.54 | F | F | NH | 4-SO₂CF₃—Ph | |

2. Formulation Examples

| 2.1. Emulsifiable concentrates | a) | b) | c) |
|---|---|---|---|
| a compound of Tables 1 to 6 | 25% | 40% | 50% |
| calcium dodecylbenzenesulfonate | 5% | 8% | 6% |
| castor oil polyethylene glycol ether | 5% | — | — |

2. Formulation Examples

-continued

| | | | |
|---|---|---|---|
| (36 mol of ethylene oxide) | | | |
| tributylphenol polyethylene glycol ether | — | 12% | 4% |
| (30 mol of ethylene oxide) | | | |
| cyclohexanone | — | 15% | 20% |
| xylene mixture | 65% | 25% | 20% |

Emulsions of any desired concentration can be prepared from such concentrates by dilution with water.

2.2. Emulsifiable concentrates

| | a) | b) | c) |
|---|---|---|---|
| a compound of Tables 1 to 6 | 10% | 8% | 60% |
| octylphenol polyethylene glycol ether | 3% | 3% | 2% |
| (4–5 mol of ethylene oxide) | | | |
| calcium dodecylbenzenesulfonate | 3% | 4% | 4% |
| castor oil polyethylene glycol ether | 4% | 5% | 4% |
| (35 mol of ethylene oxide) | | | |
| cyclohexanone | 30% | 40% | 15% |
| xylene mixture | 50% | 40% | 15% |

Emulsions of any desired concentration can be prepared from such concentrates by dilution with water.

2.3. Suspension concentrate

| | |
|---|---|
| a compound of Tables 1 to 6 | 40% |
| ethylene glycol | 10% |
| nonylphenol polyethylene glycol ether | 6% |
| (15 mol of ethylene oxide) | |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

2.4. Powder mixtures dispersible in water

| | a) | b) | c) |
|---|---|---|---|
| a compound of Tables 1 to 6 | 25% | 50% | 75% |
| sodium lignosulfonate | 5% | 5% | — |
| oleic acid | 3% | — | 5% |
| sodium diisobutylnaphthalenesulfonate | — | 6% | 10% |
| octylphenol polyethylene glycol ether | — | 2% | — |
| (7–8 mol of ethylene oxide) | | | |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of any desired concentration.

2.5. Dusts

| | a) | b) |
|---|---|---|
| a compound of Tables 1 to 6 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient and grinding the mixture.

2.6. Granules

| | a) | b) |
|---|---|---|
| a compound of Tables 1 to 6 | 5% | 10% |
| kaolin | 94% | — |
| highly dispersed silicic acid | 1% | — |
| attapulgite | — | 90% |

The active ingredient is dissolved in methylene chloride and the solution is sprayed onto the carrier, and the solvent is subsequently evaporated in vacuo. Such granules can be mixed with animal feed.

2.7. Granules

| | |
|---|---|
| a compound of Tables 1 to 6 | 10% |
| sodium lignosulfonate | 2% |
| carboxymethylcellulose | 1% |
| kaolin | 87% |

2. Formulation Examples

-continued

The active ingredient is mixed and ground with the adjuvants, and the mixture is moistened with water. The mixture is extruded and then dried in a stream of air.

2.8. Granules

| | |
|---|---|
| a compound of Tables 1 to 6 | 3% |
| polyethylene glycol (MW 200) | 3% |
| kaolin | 94% |

(MW = molecular weight)

The finely ground active ingredient is uniformly applied, in a mixer, to the kaolin moistened with polyethylene glycol. Non-dusty coated granules are obtained in this manner.

2.9. Tablets

Constituents (for 1000 tablets):

| | |
|---|---|
| a compound of Tables 1 to 6 | 25.0 g |
| lactose | 100.7 g |
| wheat starch | 7.5 g |
| polyethylene glycol 6000 | 5.0 g |
| talcum | 5.0 g |
| magnesium stearate | 1.8 g |
| demineralised water | q.s. |

All the solid ingredients are first forced through a sieve of 0.6 mm mesh size. Then the active ingredient, the lactose, the talcum and half the starch are mixed together. The other half of the starch is suspended in 40 ml of water and the suspension is added to a boiling solution of the polyethylene glycol in 100 ml of water. The resulting starch paste is added to the main batch and the mixture is granulated, if necessary with the addition of water. The granules are dried overnight at 35°, forced through a sieve of 1.2 mm mesh size, mixed with the magnesium stearate and compressed to form tablets which have a mesh size of about 6 mm and which are concave on both sides.

2.10. Injectable formulations

A. Oily vehicle (slow release)

| | |
|---|---|
| a compound of Tables 1 to 6 | 0.1–1.0 g |
| groundnut oil | ad 100 ml |
| a compound of Tables 1 to 6 | 0.1–1.0 g |
| sesame oil | ad 100 ml |

The active ingredient is dissolved in a portion of the oil with stirring and optionally with gentle heating, and after cooling the solution is made up to the desired volume and sterile-filtered through a suitable 0.22 mm membrane filter.

B. Water-miscible solvent (medium rate of release)

| | |
|---|---|
| a compound of Tables 1 to 6 | 0.1–1.0 g |
| 4-hydroxymethyl-1,3-dioxolane (glycerol formal) | 40 g |
| 1,2-propanediol | ad 100 ml |
| a compound of Tables 1 to 6 | 0.1–1.0 g |
| glycerol dimethyl ketal | 40 g |
| 1,2-propanediol | ad 100 ml |

The active ingredient is dissolved in a portion of the solvent with stirring, and the solution is made up to the desired volume and sterile-filtered through a suitable 0.22 mm membrane filter.

C. Aqueous solubilisate (rapid release)

| | |
|---|---|
| a compound of Tables 1 to 6 | 0.1–1.0 g |
| polyethoxylated castor oil (40 ethylene oxide units) | 10 g |
| 1,2-propanediol | 20 g |
| benzyl alcohol | 1 g |
| aqua ad inject. | ad 100 ml |
| a compound of Tables 1 to 6 | 0.1–1.0 g |

-continued

| 2.10. Injectable formulations | |
|---|---|
| polyethoxylated sorbitan monooleate (20 ethylene oxide units) | 8 g |
| 4-hydroxymethyl-1,3-dioxolane (glycerol formal) | 20 g |
| benzyl alcohol | 1 g |
| aqua ad inject. | ad 100 ml |

Preparation: The active ingredient is dissolved in the solvents and the surfactant, and the solution is made up to the desired volume with water. Sterile-filtration is then carried out through a suitable membrane filter of 0.22 mm pore diameter.

The aqueous systems can be used in a preferred manner also for oral and/or intraruminal administration.

| 2.11. Pour on | | |
|---|---|---|
| A. | a compound of Tables 1 to 6 | 10% |
| | epoxidised soybean oil | 5% |
| | oleyl alcohol | 85% |
| B. | a compound of Tables 1 to 6 | 20% |
| | pyrrolidin-2-one | 15% |
| | isopropyl myristate | 65% |

It is also possible to add to the described compositions further biologically active substances or additives that have neutral behaviour towards the compounds of formula (I) and have no adverse effect on the host animal to be treated, and also mineral salts or vitamins.

3. BIOLOGICAL EXAMPLES
A. Insecticidal Action
3.1. Action Against *Aphis craccivora*

Pea seedlings are infested with *Aphis craccivora*, subsequently sprayed with a spray mixture comprising 100 ppm of active ingredient and then incubated at 20° C. 3 and 6 days later the percentage reduction in population (% activity) is determined by comparing the number of dead aphids on the treated plants with that on untreated plants. Compounds of Tables 1 to 6 exhibit good activity in this test.

3.2. Action against *Diabrotica balteata*

Maize seedlings are sprayed with an aqueous emulsion spray mixture comprising 100 ppm of active ingredient and, after the spray-coating has dried, are populated with 10 *Diabrotica balteata* larvae in the second stage and then placed in a plastics container. 6 days later, the percentage reduction in population (% activity) is determined by comparing the number of dead larvae on the treated plants with that on untreated plants.

Compounds of Tables 1 to 6 exhibit good activity in this test. For example, especially compounds 3.9, 4.13, 4.15 and 4.20 bring about a more than 80% reduction in the pest population.

3.3. Action Against *Heliothis virescens*

Young soybean plants are sprayed with an aqueous emulsion spray mixture comprising 100 ppm of active ingredient and, after the spray-coating has dried, are populated with 10 caterpillars of *Heliothis virescens* in the first stage and then placed in a plastics container. 6 days later, the percentage reduction in population and in feeding damage (% activity) are determined by comparing the number of dead caterpillars and the feeding damage on the treated plants with that on untreated plants.

Compounds of Tables 1 to 6 exhibit good activity in this test. For example, especially compounds 3.12, 3.13, 3.15, 3.20, 3.21, 3.107 to 3.109 and 3.112 bring about a more than 80% reduction in the pest population.

3.4. Action Against *Spodoptera littoralis*

Young soybean plants are sprayed with an aqueous emulsion spray mixture comprising 100 ppm of active ingredient and, after the spray-coating has dried, are populated with 10 caterpillars of Spodoptera littoralis in the third stage and then placed in a plastics container. 3 days later, the percentage reduction in population and the percentage reduction in feeding damage (% activity) are determined by comparing the number of dead caterpillars and the feeding damage on the treated plants with that on untreated plants.

Compounds of Tables 1 to 6 exhibit good activity in this test. For example, especially compounds 1.50, 1.361, 1.374, 1.380, 1.390, 1.606, 3.9, 3.12 to 3.16, 3.20 to 3.22, 3.31, 3.43, 3.108, 3.109, 3.112, 4.05, 4.13, 4.14, 8.22 and 8.23 bring about a more than 80% reduction in the pest population.

3.5. Action Against *Nilaparvata lugens*

Rice plants are treated with an aqueous emulsion spray mixture comprising 400 ppm of active ingredient. After the spray-coating has dried, the rice plants are populated with cicada larvae in the 2nd and 3rd stages. The evaluation is carried out 21 days later. The percentage reduction in population (% activity) is determined by comparing the number of surviving cicadas on the treated plants with that on untreated plants.

Compounds of Tables 1 to 6 exhibit good activity in this test.

3.6. Action Against *Crocidolomia binotalis*

Young cabbage plants are sprayed with an aqueous emulsion spray mixture comprising 400 ppm of active ingredient. After the spray-coating has dried, the cabbage plants are populated with 10 *Crocidolomia binotalis* caterpillars in the third stage and placed in a plastics container. The evaluation is carried out 3 days later. The percentage reduction in population and the percentage reduction in feeding damage (% activity) are determined by comparing the number of dead caterpillars and the feeding damage on the treated plants with that on untreated plants.

Compounds of Tables 1 to 6 exhibit good activity in this test.

3.7. Action Against *Anthonomus grandis*

Young cotton plants are sprayed with an aqueous emulsion spray mixture comprising 400 ppm of active ingredient. After the spray-coating has dried, the cotton plants are populated with 10 *Anthonomus grandis* adults and placed in a plastics container. The evaluation is carried out 3 days later. The percentage reduction in population and the percentage reduction in feeding damage (% activity) are determined by comparing the number of dead weevils and the feeding damage on the treated plants with that on untreated plants.

Compounds of Tables 1 to 6 exhibit good activity in this test.

3.8. Action Against *Aonidiella aurantii*

Potato tubers are populated with crawlers of *Aonidiella aurantii*. After about 2 weeks the potatoes are immersed in an aqueous emulsion or suspension spray mixture comprising 400 ppm of active ingredient. When the tubers have dried they are incubated in a plastics container. For evaluation, 10 to 12 weeks later the survival rate of the crawlers of the first subsequent generation of the treated population is compared with that of untreated controls.

Compounds of Tables 1 to 6 exhibit good activity in this test.

3.9. Action Against *Bemisia tabaci*

Dwarf bean plants are placed in gauze cages and populated with adults of *Bemisia tabaci*. After oviposition has taken place, all adults are removed. 10 days later the plants and the nymphs located thereon are sprayed with an aqueous emulsion spray mixture comprising 400 ppm of active ingredient. After a further 14 days, the percentage of eggs that have hatched is evaluated in comparison with untreated controls.

Compounds of Tables 1 to 6 exhibit good activity in this test.

B. Acaricidal Action 3.10. Action Against *Tetranychus urticae*

Young bean plants are populated with a mixed population of *Tetranychus urticae* and sprayed 1 day later with an aqueous emulsion spray mixture comprising 100 ppm of active ingredient, incubated for 6 days at 25° C. and then evaluated. The percentage reduction in population (% activity) is determined by comparing the number of dead eggs, larvae and adults on the treated plants with that on untreated plants.

Compounds of Tables 1 to 6 exhibit good activity in this test. For example, especially compounds 3.13, 3.14, 3.16, 3.19 to 3.22, 4.13, 4.30 and 4.33 bring about a more than 80% reduction in the pest population.

3.11. Action Against *Panonychus ulmi* (OP and carb. resistant)

Apple seedlings are populated with adult females of *Panonychus ulmi*. After seven days the infested plants are sprayed to drip point with an aqueous emulsion spray mixture comprising 400 ppm of the test compound and are cultivated in a greenhouse. The evaluation is carried out after 14 days. The percentage reduction in population (% activity) is determined by comparing the number of dead spider mites on the treated plants with that on untreated plants.

Compounds of Tables 1 to 6 exhibit good activity in this test.

C. Ectoparasiticidal Action 3.12. Control of Adult Fleas in Cats by Means of Pour-on Application In order to determine the effectiveness of the test compounds against fully grown fleas, four groups each of two cats are used. Each cat is infested with 100 cat fleas [*Ctenocephalides felis* (Bouche)] and treated with 20 mg of active ingredient per kg body weight. The treatment is effected by applying the formulation to a locally limited area on the back of the cat's neck. One group is infested with fleas but is treated only with a placebo, that is to say a formulation without active ingredient, and serves as control. Another group is treated with nitenpyram as comparison substance; the two remaining groups are treated with the test compounds. Evaluation is made in each case by combing surviving fleas out of the animal's coat, counting them and comparing the number counted with the number of fleas in the control group and in the group treated with nitenpyram. The procedure in detail is as follows: each cat is infested with 100 fleas immediately after treatment on day 0. On day +1, each animal is combed and the number of surviving fleas is determined; the surviving fleas are then replaced on the same cat and after 24 hours the combing and evaluation are repeated. The fleas still surviving after those 24 hours are not returned to the cat. The described procedure is then repeated on days +3, +7, +9, +14, +21, +28, +35, +42 and +49 and in this way the effectiveness and duration of action are determined. On every day on which surviving fleas are combed out, a blood sample of about 2.7 ml is taken from each cat—with the exception of the control group—and the content of active ingredient is measured. The effectiveness is determined in accordance with the following formula:

$$\% \text{ effectiveness} = \frac{\substack{\text{number of living fleas} \\ \text{per control animal}} \text{ minus } \substack{\text{number of living fleas} \\ \text{per test animal}}}{\text{number of living fleas per control animal}} * 100$$

It is shown that the compounds of formula (I) according to the invention achieve excellent long-term action in comparison with nitenpyram.

In dogs the test proceeds in an entirely analogous manner. Similar effects are also observed when the substances are administered not in the form of a pour-on but in the form of an injection solution.

3.13. Control of Adult Fleas in Cats by Means of Subcutaneous Injection

In order to determine the effectiveness of the test compounds against fully grown fleas, four groups each of two cats aged from 1.5 to 4 years are used. Each cat is infested with 100 cat fleas [*Ctenocephalides felis* (Bouche)] and treated with 20 mg of active ingredient per kg body weight. The treatment is effected by subcutaneous injection of a solution of the active ingredient behind the left shoulder blade. One group is infested with fleas but is treated only with a placebo, that is to say a formulation without active ingredient, and serves as control. Another group is treated with nitenpyram as comparison substance; the two remaining groups are treated with the test compounds. The evaluation is in each case carried out analogously to the preceding Example.

It is shown that after subcutaneous injection the compounds of formula (I) according to the invention achieve excellent long-term action in comparison with nitenpyram.

The analogous test with dogs gives comparable results.

What is claimed is:

1. A compound of formula

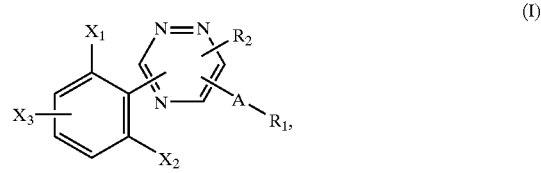

(I)

wherein

R₁ is unsubstituted or mono- to penta-substituted phenyl, unsubstituted or mono- to penta-substituted naphthyl or an unsubstituted or mono- to penta-substituted heteroaryl group comprising pyridyl, pyrimidyl, s-triazinyl, 1,3,4-triazinyl, thienyl, furanyl, pyrryl, pyrazolyl, imidazolyl, thiazolyl, triazolyl, oxazolyl, thiadiazolyl, oxadiazolyl, benzothienyl, benzofuranyl, benzothiazolyl, indolyl or indazolyl, the substituents being selected from the group consisting of OH, halogen, CN, NO₂, C₁–C₆alkyl, C₃–C₈cycloalkyl, optionally substituted C₃–C₈cycloalkenyl, C₁–C₆alkyl-C₃–C₈cycloalkyl, C₃–C₈cycloalkyl-C₁–C₆alkyl, C₁–C₆haloalkyl, C₃–C₈halocycloalkyl, C₁–C₆alkoxy, C₃–C₈cycloalkoxy, C₁–C₆haloalkoxy, C₃–C₈halocycloalkoxy, C₁–C₆alkylthio, C₃–C₈cycloalkylthio, C₁–C₆haloalkylthio, C₃–C₈halocycloalkylthio, C₁–C₆alkylsulfinyl, C₃–C₈cycloalkylsulfonyl, C₁–C₆haloalkylsulfonyl, C₃–C₈halocycloalkylsulfonyl, C₁–C₆alkylsulfonyl, C₃–C₈cycloalkylsulfonyl, C₁–C₆haloalkylsulfonyl, C₃–C₈halocycloalkylsulfonyl, optionally substituted $C_2$–$C_8$alkenyl, optionally substituted $C_2$–$C_8$alkynyl, $C_1$–$C_6$alkylcarbonyl, $C_1$–$C_6$alkyl-C(=NOR$_6$), —P(=O)(O$C_1$–$C_6$alkyl)$_2$, R$_7$, unsubstituted or mono- to penta-substituted phenyl, an unsubstituted or mono- to penta-substituted heteroaryl group comprising pyridyl, pyrimidyl, s-triazinyl, thienyl, furanyl, pyrryl, pyrazolyl, imidazolyl, thiazoyl, oxazolyl, thiadiazolyl, oxadiazolyl, benzothienyl, benzofuranyl, benzothiazolyl, indolyl or indazolyl; wherein the substituents of the said phenyl and heteroaryl radicals are selected from the group consisting of OH, halogen, CN, NO$_2$, $C_1$–$C_6$alkyl, optionally substituted $C_2$–$C_8$alkenyl, optionally substituted $C_2$–$C_8$alkynyl, $C_3$–$C_8$cycloalkyl, optionally substituted $C_3$–$C_8$cycloalkenyl, $C_1$–$C_6$haloalkyl, $C_3$–$C_8$halocycloalkyl, $C_1$–$C_6$alkoxy, $C_3$–$C_8$cycloalkoxy, $C_1$–$C_6$haloalkoxy, $C_3$–$C_8$halocycloalkoxy, $C_1$–$C_6$alkylthio, $C_3$–$C_8$cycloalkylthio, $C_1$–$C_6$haloalkylthio, $C_3$–$C_8$halocycloalkylthio, $C_1$–$C_6$alkylsulfinyl, $C_3$–$C_8$cycloalkylsulfonyl, $C_1$–$C_6$haloalkylsulfonyl, $C_3$–$C_8$halocycloalkylsulfonyl, $C_1$–$C_6$alkylsulfonyl, $C_3$–$C_8$cycloalkylsulfonyl, $C_1$–$C_6$haloalkylsulfonyl, $C_3$–$C_8$halocycloalkylsulfonyl, $C_2$–$C_8$alkenyl, which is unsubstituted or substituted, $C_2$–$C_8$alkynyl, which is unsubstituted or substituted, $C_1$–$C_6$alkylcarbonyl, —CH(=NOR$_6$), —C($C_1$–$C_6$alkyl)(NOR$_6$), $C_1$–$C_6$alkyl-C(NOR$_6$), —CHO, —C(=O)—$C_1$–$C_6$alkyl and R$_7$;

unsubstituted or mono- to penta-substituted phenoxy;

unsubstituted or mono- to penta-substituted phenylthio;

unsubstituted or mono- to penta-substituted phenylamino; and unsubstituted or mono- to penta-substituted phenyl-($C_1$–$C_6$alkyl)-amino;

the substituents of the phenoxy, phenylthio, phenylamino and phenyl-($C_1$–$C_6$alkyl)-amino groups being selected from the group consisting of halogen, CN, NO$_2$, $C_1$–$C_6$alkyl, $C_3$–$C_8$cycloalkyl, $C_1$–$C_6$haloalkyl, $C_3$–$C_8$halocycloalkyl, $C_1$–$C_6$alkoxy, $C_1$–$C_6$haloalkoxy, $C_3$–$C_8$cycloalkoxy, $C_1$–$C_6$alkylthio, $C_1$–$C_6$alkylsulfinyl, $C_1$–$C_6$haloalkylsulfinyl, $C_1$–$C_6$alkylsulfonyl, $C_1$–$C_6$haloalkylsulfonyl, $C_3$–$C_8$cycloalkylthio, $C_1$–$C_6$haloalkylthio and $C_3$–$C_8$halocycloalkylthio;

$R_2$ is H, OH, halogen, CN, NO$_2$, optionally substituted $C_1$–$C_6$alkyl, $C_1$–$C_6$alkoxy, $C_1$–$C_6$alkoxy-$C_1$–$C_6$alkyl, $C_1$–$C_6$alkylthio, $C_1$–$C_6$alkylthio-$C_1$–$C_6$alkyl, $C_3$–$C_8$cycloalkyl, $C_1$–$C_6$haloalkyl, $C_3$–$C_8$halocycloalkyl, —NH—$C_1$–$C_6$-alkyl, SH or CH$_2$-NO$_2$;

A is a single bond, $C_1$–$C_{12}$alkylene, O, O($C_1$–$C_{12}$alkylene), S(O)$_n$, S(O)$_n$($C_1$–$C_{12}$alkylene), $C_2$–$C_8$alkenylene, $C_2$–$C_8$alkynylene; NR$_3$ or NR$_3$ ($C_1$–$C_{12}$alkylene);

$R_3$ is H, $C_1$–$C_6$alkyl, $C_3$–$C_8$cycloalkyl, $C_1$–$C_6$haloalkyl, $C_2$–$C_8$alkenyl, $C_2$–$C_8$alkynyl, aryl-$C_1$–$C_6$alkyl, (CH$_2$)$_p$C(O)R$_4$ or $C_1$–$C_6$alkoxy-$C_2$–$C_6$alkyl;

$R_4$ is H, $C_1$–$C_6$alkyl, $C_3$–$C_8$cycloalkyl, $C_1$–$C_6$haloalkyl, $C_1$–$C_6$alkoxy, N(R$_5$)$_2$ or $C_1$–$C_6$alkoxy$C_2$–$C_6$alkyl;

$R_5$ is H, $C_1$–$C_6$alkyl, $C_3$–$C_8$cycloalkyl, $C_1$–$C_6$haloalkyl or aryl-$C_1$–$C_6$alkyl;

$R_6$ is H, $C_1$–$C_6$alkyl, $C_3$–$C_8$cycloalkyl or —C(=O)—R$_5$;

$R_7$ is

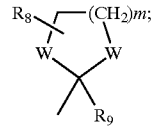

$R_8$ and $R_9$ are each independently of the other H or $C_1$–$C_6$alkyl;

$X_1$ is $R_{10}$;

$X_2$ and $X_3$ are each independently of the other H or $R_{10}$;

$R_{10}$ is halogen, CN, NO$_2$, $C_1$–$C_6$alkyl, $C_3$–$C_8$cycloalkyl, $C_1$–$C_6$haloalkyl, $C_3$–$C_8$halocycloalkyl, $C_1$–$C_6$alkoxy, $C_3$–$C_8$cycloalkoxy, $C_1$–$C_6$haloalkoxy, $C_3$–$C_8$halocycloalkoxy, $C_1$–$C_6$alkylthio, $C_3$–$C_8$cycloalkylthio, $C_1$–$C_6$haloalkylthio or $C_3$–$C_8$halocycloalkylthio;

m is 1, 2, 3 or 4;

n is 0, 1 or 2; and

W is O or S;

and the physiologically tolerable and agrochemically acceptable additional compounds thereof, and where appropriate to E/Z isomers, to mixtures of E/Z isomers and to tautomers, in each case in free form or in salt form, with the proviso that the radical A—R$_1$ and the phenyl group substituted by $X_1$, $X_2$ and $X_3$ are not in the vicinal position relative to one another on the triazine ring, with the further proviso, that $X_1$ is not CH$_3$, Cl or F, when $X_2$ and $X_3$ are H, A is a single bond, R$_1$ is phenyl, 2-fluorophenyl, p-fluorophenyl or 3-chlorophenyl and R$_2$ is H, Cl or NHC$_2$—H$_5$;

and with the exception of 3,6-di-(2-chlorophenyl)-5-hydroxy-1,2,4-triazine and with the exception of 3-(2-methylphenyl)-6-(4-methylphenyl)-5-trifluoromethyl-1,2,4-triazine.

2. A compound according to claim 1 of formula (I) in the free form.

3. A compound according to claim 1 of formula (I), wherein

A is a single bond, $C_1$–$C_4$alkylene, O, OCH$_2$, $C_2$–$C_4$alkenylene, $C_2$–$C_4$alkynylene or NR$_3$.

4. A compound according to claim 1 of formula (I), wherein $X_1$ is halogen, $C_1$–$C_4$alkyl, $C_3$–$C_6$cycloalkyl, $C_1$–$C_4$haloalkyl, $C_1$–$C_4$alkoxy, $C_1$–$C_4$haloalkoxy, $C_1$–$C_4$alkylthio or $C_1$–$C_4$haloalkylthio.

5. A composition for the control of insects, which comprises as active ingredient one or more compounds of formula (I) as described in claim 1 and one or more adjuvants.

6. A method of controlling insects, which comprises applying an insecticidally effective amount of one or more compounds of formula (I) as described in claim 1 to the insects or the locus thereof.

* * * * *